United States Patent
Sagehashi et al.

(10) Patent No.: US 9,235,122 B2
(45) Date of Patent: Jan. 12, 2016

(54) MONOMER, POLYMER, RESIST COMPOSITION, AND PATTERNING PROCESS

(71) Applicant: SHIN-ETSU CHEMICAL CO., LTD., Tokyo (JP)

(72) Inventors: Masayoshi Sagehashi, Joetsu (JP); Koji Hasegawa, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 31 days.

(21) Appl. No.: 14/108,549

(22) Filed: Dec. 17, 2013

(65) Prior Publication Data

US 2014/0199631 A1    Jul. 17, 2014

(30) Foreign Application Priority Data

Jan. 15, 2013   (JP) .................... 2013-004273

(51) Int. Cl.
*G03F 7/004*   (2006.01)
*C07D 309/12*   (2006.01)
(Continued)

(52) U.S. Cl.
CPC .............. *G03F 7/0392* (2013.01); *C07C 69/54* (2013.01); *C07D 309/12* (2013.01); *G03F 7/038* (2013.01); *C07C 2102/42* (2013.01); *C07C 2103/68* (2013.01)

(58) Field of Classification Search
CPC ..................................................... G03F 7/0392
See application file for complete search history.

(56) References Cited

U.S. PATENT DOCUMENTS 6,312,867 B1   11/2001 Kinsho et al.
7,537,880 B2   5/2009 Harada et al.
(Continued)

FOREIGN PATENT DOCUMENTS

JP   2000-336121 A   12/2000
JP   2007-25634 A   2/2007
(Continued)

OTHER PUBLICATIONS

Nakamura et al., "Contact Hole Formation by Multiple Exposure Technique in Ultra-low k1 Lithography", Proceedings of SPIE, 2004, p. 255-263, SPIE vol. 5377.
(Continued)

*Primary Examiner* — Anca Eoff
*Assistant Examiner* — Alyssa L Cepluch
(74) *Attorney, Agent, or Firm* — Westerman, Hattori, Daniels & Adrian, LLP

(57) ABSTRACT

A polymer for resist use is obtainable from a monomer having formula (1) wherein $R^1$ is H, $CH_3$ or $CF_3$ and $R^2$ is H or an acid labile group. A resist composition comprising the polymer displays a high sensitivity and a high dissolution contrast during both alkaline development and organic solvent development.

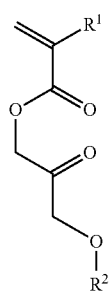

(1)

14 Claims, 1 Drawing Sheet

(51) Int. Cl.
*C07C 69/54* (2006.01)
*G03F 7/039* (2006.01)
*G03F 7/038* (2006.01)

(56) References Cited

U.S. PATENT DOCUMENTS

| | | | |
|---|---|---|---|
| 7,642,034 B2 | 1/2010 | Hatakeyama et al. | |
| 7,670,750 B2 | 3/2010 | Harada et al. | |
| 7,998,655 B2 | 8/2011 | Tsubaki | |
| 8,034,547 B2 | 10/2011 | Tsubaki et al. | |
| 8,088,557 B2 | 1/2012 | Tsubaki | |
| 8,114,571 B2 | 2/2012 | Ohashi et al. | |
| 8,227,183 B2 | 7/2012 | Tsubaki et al. | |
| 8,241,840 B2 | 8/2012 | Tsubaki et al. | |
| 8,323,872 B2 | 12/2012 | Hatakeyama et al. | |
| 8,440,386 B2 | 5/2013 | Hatakeyama et al. | |
| 2009/0269696 A1* | 10/2009 | Ohsawa et al. | 430/270.1 |
| 2011/0250539 A1 | 10/2011 | Sagehashi et al. | |
| 2011/0262864 A1* | 10/2011 | Hirano et al. | 430/285.1 |

FOREIGN PATENT DOCUMENTS

| | | |
|---|---|---|
| JP | 2007-316448 A | 12/2007 |
| JP | 2008-3569 A | 1/2008 |
| JP | 2008-81716 A | 4/2008 |
| JP | 2008-111089 A | 5/2008 |
| JP | 2008-111103 A | 5/2008 |
| JP | 2008-281974 A | 11/2008 |
| JP | 2008-281975 A | 11/2008 |
| JP | 2008-309879 A | 12/2008 |
| JP | 2009-269953 A | 11/2009 |
| JP | 4554665 B2 | 9/2010 |
| JP | 4590431 B2 | 12/2010 |
| JP | 2011-221513 A | 11/2011 |
| JP | 2011-231312 A | 11/2011 |
| JP | 2014-025085 A | 2/2014 |
| WO | WO2013125733 A1 * | 8/2013 |

OTHER PUBLICATIONS

Nakao et al., "0.12um Hole Pattern Formation by KrF Lithography for Giga Bit DRAM", IEDM 96, 1996, p. 61-64.

Truffert et al., "Ultimate contact hole resolution using immersion lithography with line/space imaging", Proceedings of SPIE, 2009, p. 72740N-1-72740N-12, SPIE vol. 7274.

Ferroni et al., "A Three-Step Preparation of Dihydroxyacetone Phosphate Dimethyl Acetal", J. Org. Chem., 1999, p. 4943-4945, vol. 64, No. 13.

Arimitsu et al., "Sensitivity Enhancement of Chemical-Amplification-Type Photoimaging Materials by Acetoacetic Acid Derivatives", Journal of Photopolymer Science and Technology, 1995, p. 43-44, vol. 8, No. 1.

Kudo et al., "Enhancement of the Sensitivity of Chemical-Amplification-Type Photoimaging Materials by β-Tosyloxyketone Acetals", Journal of Photopolymer Science and Technology, 1995, p. 45-46, vol. 8, No. 1.

Arimitsu et al., "Effect of Phenolic Hydroxyl Residues on the Improvement of Acid-Proliferation-Type Photoimaging Materials", Journal of Photopolymer Science and Technology, 1996, p. 29-30, vol. 9, No. 1.

Notice of Reasons for Refusal dated Jun. 9, 2015, issued in corresponding Japanese Patent Application No. 2013-004273 (4 pages).

* cited by examiner

MONOMER, POLYMER, RESIST COMPOSITION, AND PATTERNING PROCESS

CROSS-REFERENCE TO RELATED APPLICATION

This non-provisional application claims priority under 35 U.S.C. §119(a) on Patent Application No. 2013-004273 filed in Japan on Jan. 15, 2013, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the resist composition. The monomer is useful for the preparation of a polymer that finds use as a base resin in a resist composition which is subject to a pattern forming process involving exposure of resist film, deprotection reaction with the aid of acid and heat, and development in an organic solvent to form a negative tone pattern in which the unexposed region is dissolved and the exposed region is not dissolved.

BACKGROUND ART

In the recent drive for higher integration and operating speeds in LSI devices, the pattern rule is made drastically finer. The photolithography which is currently on widespread use in the art is approaching the essential limit of resolution determined by the wavelength of a light source. As the light source used in the lithography for resist pattern formation, g-line (436 nm) or i-line (365 nm) from a mercury lamp was widely used in 1980's. Reducing the wavelength of exposure light was believed effective as the means for further reducing the feature size. For the mass production process of 64 MB dynamic random access memories (DRAM, processing feature size 0.25 µm or less) in 1990's and later ones, the exposure light source of i-line (365 nm) was replaced by a KrF excimer laser having a shorter wavelength of 248 nm. However, for the fabrication of DRAM with a degree of integration of 256 MB and 1 GB or more requiring a finer patterning technology (processing feature size 0.2 µm or less), a shorter wavelength light source was required. Over a decade, photolithography using ArF excimer laser light (193 nm) has been under active investigation. It was expected at the initial that the ArF lithography would be applied to the fabrication of 180-nm node devices. However, the KrF excimer lithography survived to the mass-scale fabrication of 130-nm node devices. So, the full application of ArF lithography started from the 90-nm node. The ArF lithography combined with a lens having an increased numerical aperture (NA) of 0.9 is considered to comply with 65-nm node devices. For the next 45-nm node devices which required an advancement to reduce the wavelength of exposure light, the $F_2$ lithography of 157 nm wavelength became a candidate. However, for the reasons that the projection lens uses a large amount of expensive $CaF_2$ single crystal, the scanner thus becomes expensive, hard pellicles are introduced due to the extremely low durability of soft pellicles, the optical system must be accordingly altered, and the etch resistance of resist is low; the development of $F_2$ lithography was abandoned and instead, the ArF immersion lithography was introduced.

In the ArF immersion lithography, the space between the projection lens and the wafer is filled with water having a refractive index of 1.44. The partial fill system is compliant with high-speed scanning and when combined with a lens having a NA of 1.3, enables mass production of 45-nm node devices.

One candidate for the 32-nm node lithography is lithography using extreme ultraviolet (EUV) radiation with wavelength 13.5 nm. The EUV lithography has many accumulative problems to be overcome, including increased laser output, increased sensitivity, increased resolution and minimized line edge or width roughness (LER, LWR) of resist film, defect-free MoSi laminate mask, reduced aberration of reflection mirror, and the like.

Another candidate for the 32-nm node lithography is high refractive index liquid immersion lithography. The development of this technology was abandoned because LUAG, a high refractive index lens candidate had a low transmittance and the refractive index of liquid did not reach the goal of 1.8.

The process that now draws attention under the above-discussed circumstances is a double patterning process involving a first set of exposure and development to form a first pattern and a second set of exposure and development to form a pattern between the first pattern features. A number of double patterning processes are proposed. One exemplary process involves a first set of exposure and development to form a photoresist pattern having lines and spaces at intervals of 1:3, processing the underlying layer of hard mask by dry etching, applying another layer of hard mask thereon, a second set of exposure and development of a photoresist film to form a line pattern in the spaces of the first exposure, and processing the hard mask by dry etching, thereby forming a line-and-space pattern at a half pitch of the first pattern. An alternative process involves a first set of exposure and development to form a photoresist pattern having spaces and lines at intervals of 1:3, processing the underlying layer of hard mask by dry etching, applying a photoresist layer thereon, a second set of exposure and development to form a second space pattern on the remaining hard mask portion, and processing the hard mask by dry etching. In either process, the hard mask is processed by two dry etchings.

As compared with the line pattern, the hole pattern is difficult to reduce the feature size. In order for the prior art method to form fine holes, an attempt is made to form fine holes by under-exposure of a positive resist film combined with a hole pattern mask. This, however, results in the exposure margin being extremely narrowed. It is then proposed to form holes of greater size, followed by thermal flow or RELACS® method to shrink the holes as developed. However, there is a problem that control accuracy becomes lower as the pattern size after development and the size after shrinkage differ greater and the quantity of shrinkage is greater. With the hole shrinking method, the hole size can be shrunk, but the pitch cannot be narrowed.

It is then proposed in Non-Patent Document 1 that a pattern of X-direction lines is formed in a positive resist film using dipole illumination, the resist pattern is cured, another resist material is coated thereon, and a pattern of Y-direction lines is formed in the other resist film using dipole illumination, leaving a grid line pattern, spaces of which provide a hole pattern. Although a hole pattern can be formed at a wide margin by combining X and Y lines and using dipole illumination featuring a high contrast, it is difficult to etch vertically staged line patterns at a high dimensional accuracy. It is proposed in Non-Patent Document 2 to form a hole pattern by exposure of a negative resist film through a Levenson phase shift mask of X-direction lines combined with a Levenson phase shift mask of Y-direction lines. However, the crosslinking negative resist film has the drawback that the resolving power is low as compared with the positive resist film, because the maximum resolution of ultrafine holes is determined by the bridge margin.

A hole pattern resulting from a combination of two exposures of X- and Y-direction lines and subsequent image reversal into a negative pattern can be formed using a high-contrast line pattern of light. Thus holes having a narrow pitch and fine size can be opened as compared with the prior art.

Non-Patent Document 3 reports three methods for forming hole patterns via image reversal. The three methods are: method (1) involving subjecting a positive resist composition to two double-dipole exposures of X and Y lines to form a dot pattern, depositing a $SiO_2$ film thereon by LPCVD, and effecting $O_2$-RIE for reversal of dots into holes; method (2) involving forming a dot pattern by the same steps as in (1), but using a resist composition designed to turn alkali-soluble and solvent-insoluble upon heating, coating a phenol-base overcoat film thereon, effecting alkaline development for image reversal to form a hole pattern; and method (3) involving double dipole exposure of a positive resist composition and organic solvent development for image reversal to form holes.

The organic solvent development to form a negative pattern is a traditional technique. A resist composition comprising cyclized rubber is developed using an alkene such as xylene as the developer. An early chemically amplified resist composition comprising poly(tert-butoxycarbonyloxy-styrene) is developed with anisole as the developer to form a negative pattern.

Recently a highlight is put on the organic solvent development again. It would be desirable if a very fine hole pattern, which is not achievable with the positive tone, is resolvable through negative tone exposure. To this end, a positive resist composition featuring a high resolution is subjected to organic solvent development to form a negative pattern. An attempt to double a resolution by combining two developments, alkaline development and organic solvent development is under study.

As the ArF resist composition for negative tone development with organic solvent, positive ArF resist compositions of the prior art design may be used. Such pattern forming processes are described in Patent Documents 1 to 3. These patent documents disclose resist compositions for organic solvent development comprising a copolymer of hydroxyadamantane methacrylate, a copolymer of norbornane lactone methacrylate, and a copolymer of methacrylate having acidic groups including carboxyl, sulfo, phenol and thiol groups substituted with two or more acid labile groups, and pattern forming processes using the same.

Further, Patent Document 4 discloses a process for forming a pattern through organic solvent development in which a protective film is applied onto a resist film. Patent Document 5 discloses a topcoatless process for forming a pattern through organic solvent development in which an additive is added to a resist composition so that the additive may segregate at the resist film surface after spin coating to provide the surface with improved water repellency.

In positive development wherein a carboxyl group is generated by deprotection reaction and a dissolution rate is increased by neutralization reaction with aqueous alkaline developer, the dissolution rate of exposed region is at least 1,000 times higher than the dissolution rate of unexposed region, indicating a high dissolution contrast. By contrast, in negative development via organic solvent development, the dissolution rate of unexposed region due to solvation is slow and therefore, the dissolution rate differs by a factor of less than 100 between unexposed and exposed regions. A new resist material must be sought for before the dissolution contrast of negative development via organic solvent development can be enhanced.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP 4590431 (U.S. Pat. No. 7,998,655)
Patent Document 5: JP-A 2008-309879 (U.S. Pat. No. 8,088, 557)
Non-Patent Document 1: Proc. SPIE Vol. 5377, p. 255 (2004)
Non-Patent Document 2: IEEE IEDM Tech. Digest 61 (1996)
Non-Patent Document 3: Proc. SPIE Vol. 7274, p. 72740N (2009)

DISCLOSURE OF INVENTION

The organic solvent development is low in dissolution contrast, as compared with the positive resist system adapted to be dissolved in alkaline developer when deprotection reaction takes place to produce acidic carboxyl or phenol groups. Specifically, in the case of alkaline developer, the alkali dissolution rate differs more than 1,000 times between unexposed and exposed regions, whereas the difference in the case of organic solvent development is at most 100 times, and only about 10 times for certain materials. No sufficient margin is available. In the case of aqueous alkaline development, the dissolution rate is improved by neutralization reaction with carboxyl groups. In the case of organic solvent development with no accompanying reaction, the dissolution rate is low because dissolution is solely due to solvation. It is necessary not only to improve the dissolution rate of the unexposed region, but also to reduce the dissolution rate of the exposed region that is a remaining portion of resist film. If the dissolution rate of the exposed region is high, the thickness of the remaining film is so reduced that the underlying substrate may not be processed by etching through the pattern as developed. Further it is important to enhance the gradient or gamma ($\gamma$) at the dose corresponding to dissolution/non-dissolution conversion. A low $\gamma$ value is prone to form an inversely tapered profile and allows for pattern collapse in the case of a line pattern. To obtain a perpendicular pattern, the resist must have a dissolution contrast having a $\gamma$ value as high as possible.

An object of the invention is to provide a photoresist composition which displays a high sensitivity and a high dissolution contrast during both alkaline development and organic solvent development. Specifically, an object of the invention is to provide a monomer, a polymer prepared from the monomer and suited for use in photoresist compositions, a resist composition comprising the polymer as a base resin, and a pattern forming process using the resist composition.

The inventors have found that a monomer having the general formula (1) defined below can be readily synthesized, and that a resist composition comprising a polymer resulting from the monomer is not only useful in forming positive patterns with minimal roughness in conventional alkaline developer, but also is improved in dissolution contrast during organic solvent development and forms a hole pattern via positive/negative reversal which is improved in sensitivity, resolution, and dimensional uniformity.

A first embodiment of the invention provides a monomer having the general formula (1).

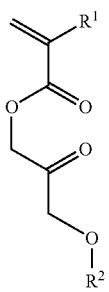

(1)

Herein $R^1$ is hydrogen, methyl or trifluoromethyl and $R^2$ is hydrogen or an acid labile group.

A second embodiment of the invention provides a monomer having the general formula (2).

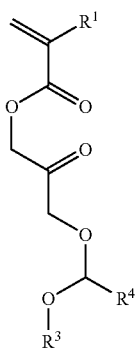

(2)

Herein $R^1$ is hydrogen, methyl or trifluoromethyl, $R^3$ is a straight, branched or cyclic, monovalent hydrocarbon group of 1 to 20 carbon atoms in which a constituent —CH$_2$— may be substituted by —O— or —C(=O)—, $R^4$ is hydrogen or a straight, branched or cyclic, monovalent hydrocarbon group of 1 to 20 carbon atoms, $R^3$ and $R^4$ may bond together to form a 5 or 6-membered ring with the carbon and oxygen atoms to which they are attached.

A third embodiment of the invention provides a polymer comprising recurring units having the general formula (3a) or (3b).

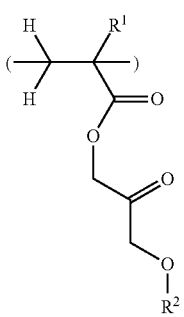

(3a)

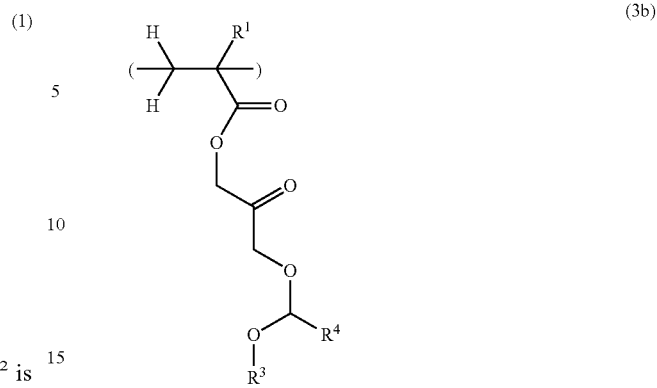

(3b)

Herein $R^1$ is hydrogen, methyl or trifluoromethyl, $R^1$ is hydrogen or an acid labile group, $R^3$ is a straight, branched or cyclic, monovalent hydrocarbon group of 1 to 20 carbon atoms in which a constituent —CH$_2$— may be substituted by —O— or —C(=O)—, $R^4$ is hydrogen or a straight, branched or cyclic, monovalent hydrocarbon group of 1 to 20 carbon atoms, $R^3$ and $R^4$ may bond together to form a 5 or 6-membered ring with the carbon and oxygen atoms to which they are attached.

In a preferred embodiment, the polymer further comprises recurring units of at least one type selected from recurring units having the general formulae (4A) to (4E).

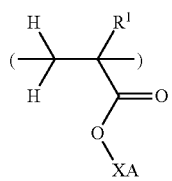

(4A)

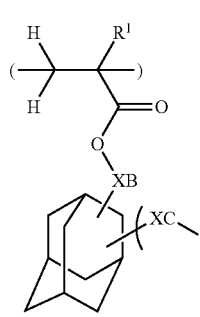

(4B)

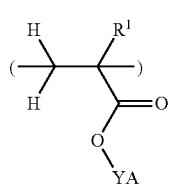

(4C)

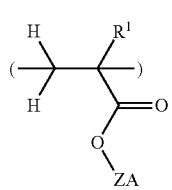

(4D)

-continued

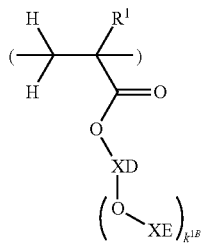

(4E)

Herein R$^1$ is as defined above, XA is an acid labile group, XB and XC are each independently a single bond or a straight or branched, divalent hydrocarbon group of 1 to 4 carbon atoms, XD is a straight, branched or cyclic, di- to pentavalent aliphatic hydrocarbon group of 1 to 16 carbon atoms in which a constituent —CH$_2$— may be substituted by —O— or —C(=O)—, XE is an acid labile group, YA is a substituent group of lactone, sultone or carbonate structure, ZA is hydrogen, a fluoroalkyl group of 1 to 15 carbon atoms or a fluoroalcohol-containing group of 1 to 15 carbon atoms, k$^{1A}$ is an integer of 1 to 3, and k$^{1B}$ is an integer of 1 to 4.

In a preferred embodiment, the polymer may further comprise recurring units of at least one type selected from sulfonium salt units (d1) to (d3) represented by the following general formula.

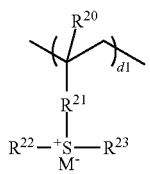

(d1)

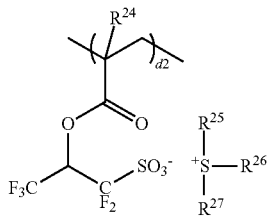

(d2)

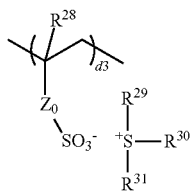

(d3)

Herein R$^{20}$, R$^{24}$, and R$^{28}$ each are hydrogen or methyl; R$^{21}$ is a single bond, phenylene, —O—R$^{33}$—, or —C(=O)—Y—R$^{33}$—, wherein Y is oxygen or NH and R$^{33}$ is a straight, branched or cyclic C$_1$-C$_6$ alkylene group, alkenylene group or phenylene group, which may contain a carbonyl (—CO—), ester (—COO—), ether (—O—), or hydroxyl moiety; R$^{22}$, R$^{23}$, R$^{25}$, R$^{26}$, R$^{27}$, R$^{29}$, R$^{30}$, and R$^{31}$ are each independently a straight, branched or cyclic C$_1$-C$_{12}$ alkyl group which may contain a carbonyl, ester or ether moiety, a C$_6$-C$_{12}$ aryl group, a C$_7$-C$_{20}$ aralkyl group, or a thiophenyl group; Z$_0$ is a single bond, methylene, ethylene, phenylene, fluorinated phenylene, —O—R$^{32}$—, or —C(=O) Z$_1$-R$^{32}$—, wherein Z$_1$ is oxygen or NH, and R$^{32}$ is a straight, branched or cyclic C$_1$-C$_6$ alkylene group, alkenylene group or phenylene group, which may contain a carbonyl, ester, ether or hydroxyl moiety; and M$^-$ is a non-nucleophilic counter ion.

A fourth embodiment is a resist composition comprising a base resin containing the polymer defined above, an acid generator, and an organic solvent; or a resist composition comprising a base resin containing the polymer defined above, and an organic solvent.

A fifth embodiment provides a pattern forming process comprising the steps of applying the resist composition defined above onto a substrate, prebaking to form a resist film, exposing the resist film to high-energy radiation, baking, and developing the exposed resist film in a developer.

In one embodiment, an aqueous alkaline solution is used as the developer in the developing step to form a positive pattern wherein the exposed region of resist film is dissolved away and the unexposed region of resist film is not dissolved.

In another embodiment, an organic solvent is used as the developer in the developing step to form a negative pattern wherein the unexposed region of resist film is dissolved away and the exposed region of resist film is not dissolved. The developer is preferably at least one organic solvent selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Preferably, the step of exposing the resist film to high-energy radiation includes KrF excimer laser lithography of wavelength 248 nm, ArF excimer laser lithography of wavelength 193 nm, EB lithography, or EUV lithography of wavelength 13.5 nm.

Advantageous Effects of Invention

A photoresist film comprising a polymer comprising recurring units derived from the inventive monomer and an acid generator is useful in forming positive patterns by conventional alkaline development. It is also effective in forming images via positive/negative reversal by organic solvent development because the photoresist film is characterized by a high dissolution contrast between the unexposed region of promoted dissolution and the exposed region of inhibited dissolution during organic solvent development. By subjecting this photoresist film to exposure through a mask bearing a lattice-like pattern and organic solvent development, a fine hole pattern can be formed at a high sensitivity and a high precision of dimensional control.

BRIEF DESCRIPTION OF DRAWINGS

1B shows the photoresist film being exposed.

DESCRIPTION OF EMBODIMENTS

Figure 1A:
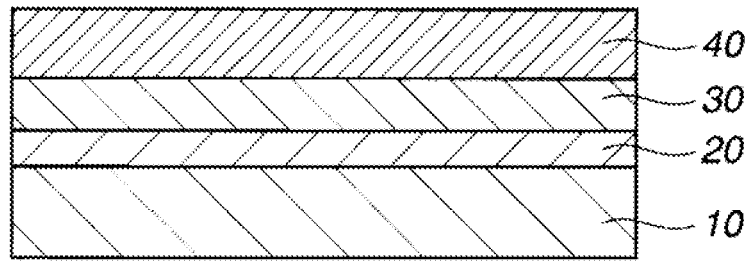
FIG. 1A shows a photoresist film formed on a substrate, FIG.

In the disclosure, the singular forms "a," an and the include plural referents unless the context clearly dictates otherwise. The notation (Cn-Cm) means a group containing from n to m carbon atoms per group.

The abbreviations and acronyms have the following meaning.
EB: electron beam
EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake It is understood that for some structures represented by chemical formulae, there can exist enantiomers and diastereomers because of the presence of asymmetric carbon atoms. In such a case, a single formula collectively represents all such isomers. The isomers may be used alone or in admixture.

Monomer

In the first embodiment, the invention provides a monomer having the general formula (1).

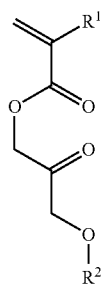

(1)

Herein $R^1$ is hydrogen, methyl or trifluoromethyl and $R^2$ is hydrogen or an acid labile group.

The acid labile group represented by $R^2$ may be selected from protective groups for alcoholic hydroxyl groups. Suitable acid labile groups include groups of the following general formulae (R1-1) and (R1-2), tertiary alkyl groups of 4 to 20 carbon atoms, preferably of 4 to 15 carbon atoms, trialkylsilyl groups in which each alkyl moiety has 1 to 5 carbon atoms, oxoalkyl groups of 4 to 15 carbon atoms, and acyl groups of 1 to 10 carbon atoms.

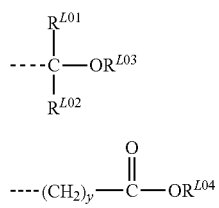

Herein and throughout the specification, the broken line designates a valence bond.

In formula (R1-1), $R^{L01}$ and $R^{L02}$ are each independently hydrogen or a straight, branched or cyclic alkyl group of 1 to 18 carbon atoms, preferably 1 to 10 carbon atoms. Examples include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. Examples of the substituted alkyl groups are as shown below.

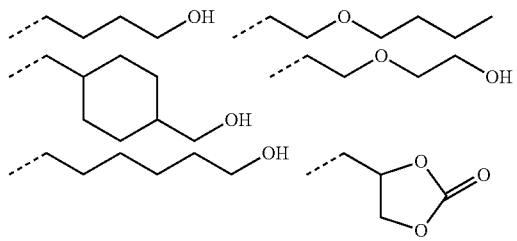

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (R1-2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (R1-1). The subscript y is an integer of 0 to 6.

Suitable groups of $R^2$ and $R^{L04}$ are illustrated below. Exemplary tertiary alkyl groups include tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Examples of the acyl group include formyl, acetyl, ethylcarbonyl, pivaloyl, methoxycarbonyl, ethoxycarbonyl, tert-butoxycarbonyl, trifluoroacetyl, and trichloroacetyl.

Of the protective groups of formula (R1-1), the straight or branched groups are exemplified by the following.

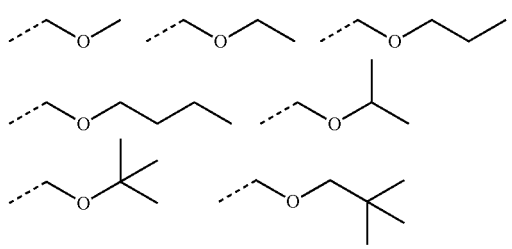

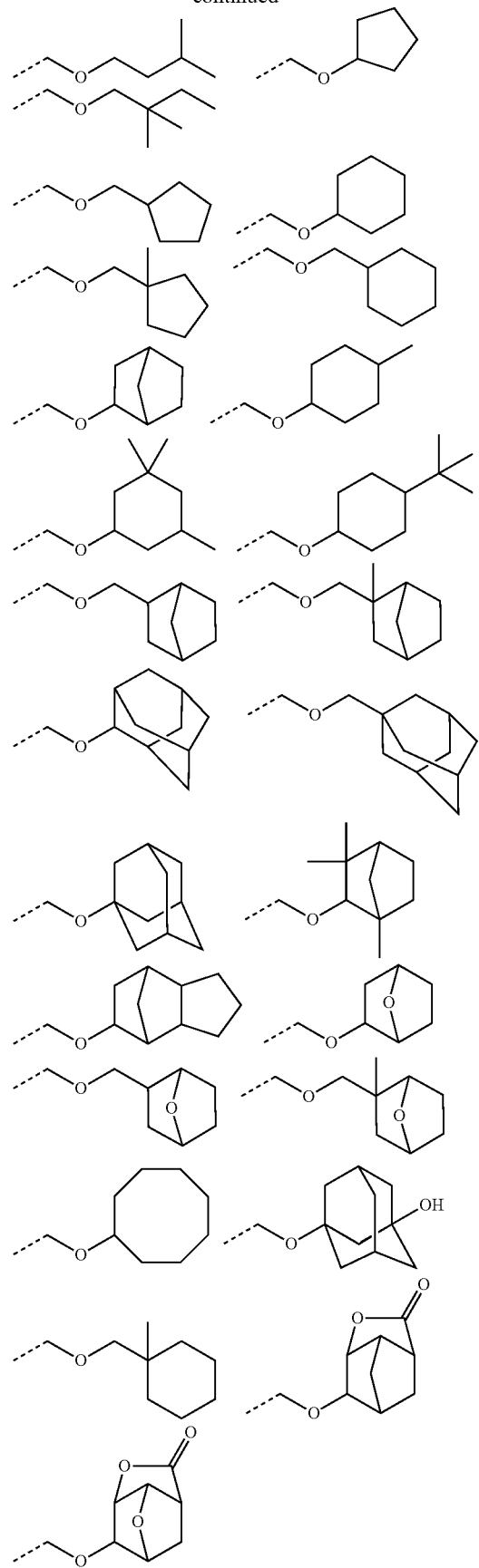
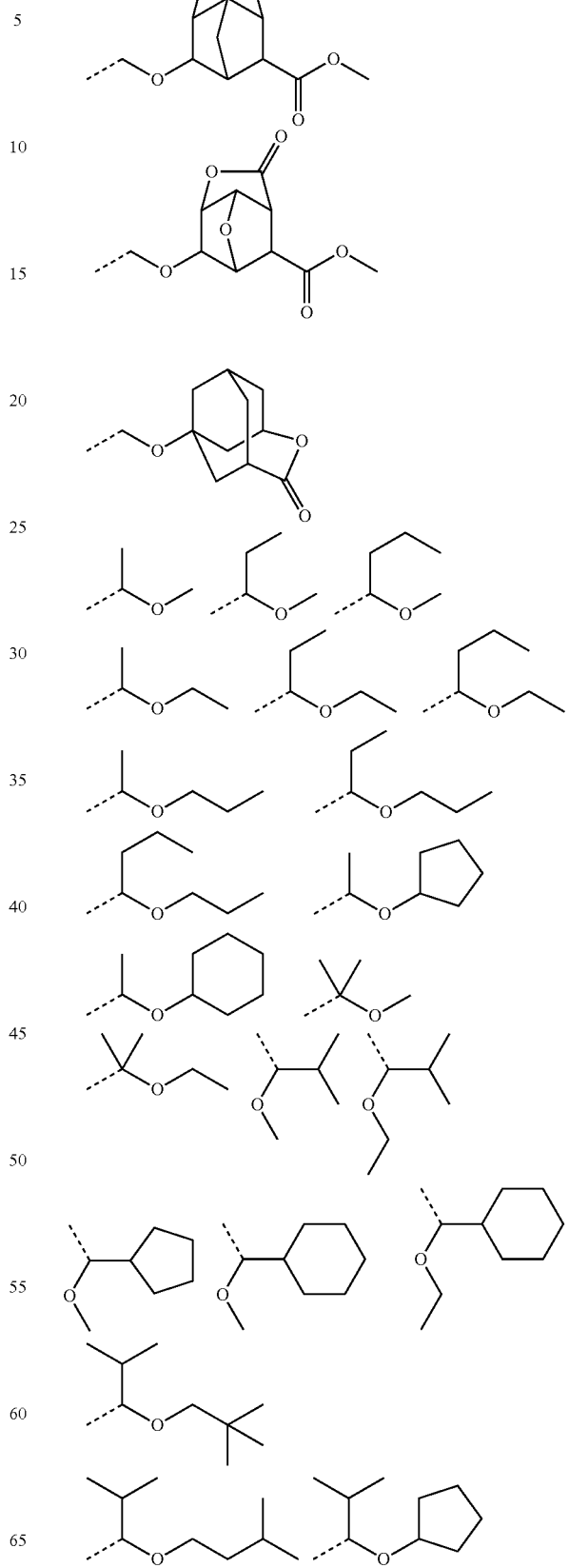

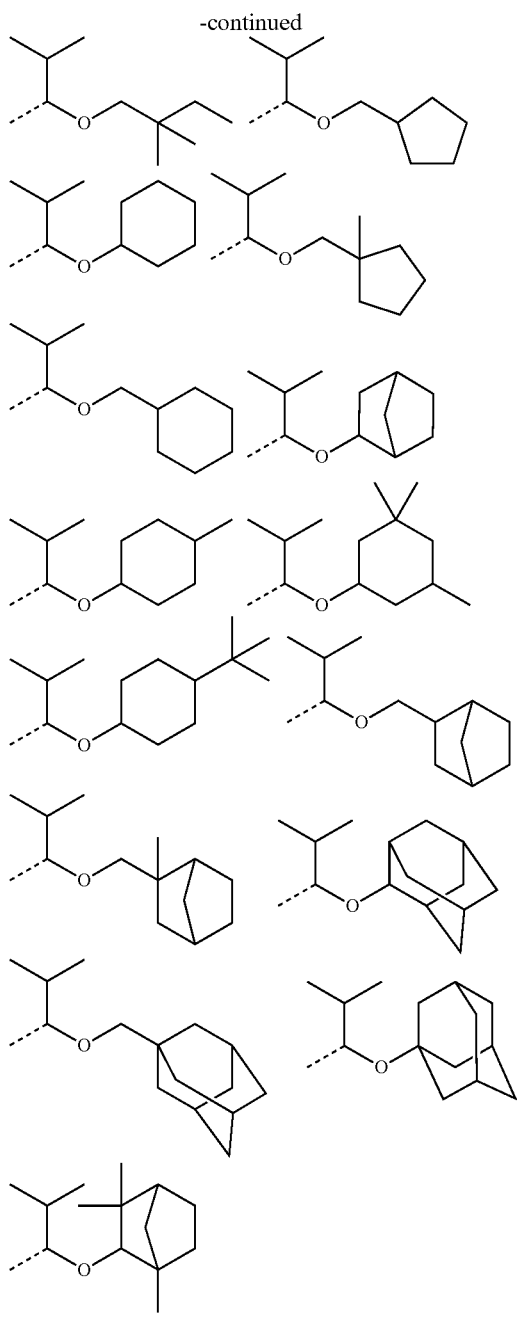

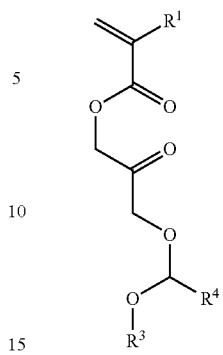
(2)

Herein $R^1$ is hydrogen, methyl or trifluoromethyl. $R^3$ is a straight, branched or cyclic, monovalent hydrocarbon group of 1 to 20 carbon atoms in which a constituent —$CH_2$— may be substituted by —O— or —C(=O)—. $R^4$ is hydrogen or a straight, branched or cyclic, monovalent hydrocarbon group of 1 to 20 carbon atoms. $R^3$ and $R^4$ may bond together to form a 5 or 6-membered ring with the carbon and oxygen atoms to which they are attached.

Typical straight, branched or cyclic, monovalent $C_1$-$C_{20}$ hydrocarbon groups represented by $R^3$ and $R^4$ are alkyl groups including methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[$5.2.1.0^{2,6}$]decanyl, and adamantyl.

Illustrative, non-limiting examples of the monomers having formulae (1) and (2) are given below wherein $R^1$ is as defined above.

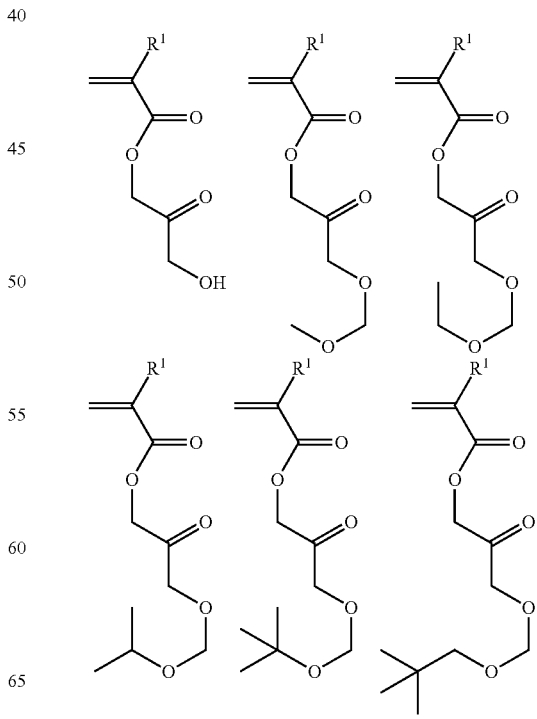

Of the protective groups of formula (R1-1), the cyclic ones are, for example, tetrahydrofuran-2-yl, 2-methyltetrahydrofuran-2-yl, tetrahydropyran-2-yl, and 2-methyltetrahydropyran-2-yl.

Examples of the protective groups of formula (R1-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

A second embodiment of the invention is a monomer having the general formula (2).

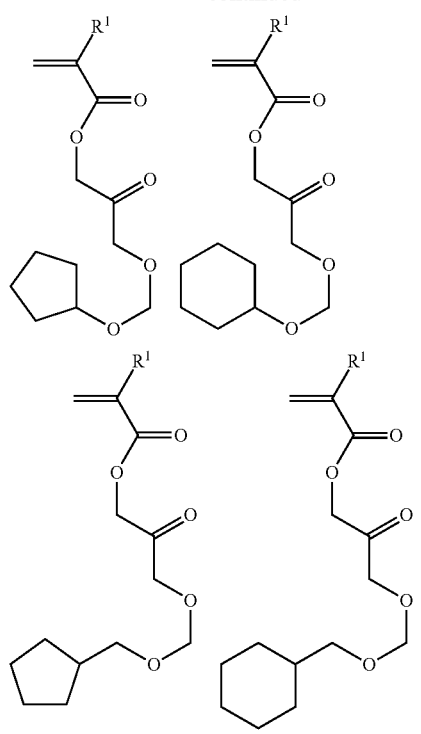
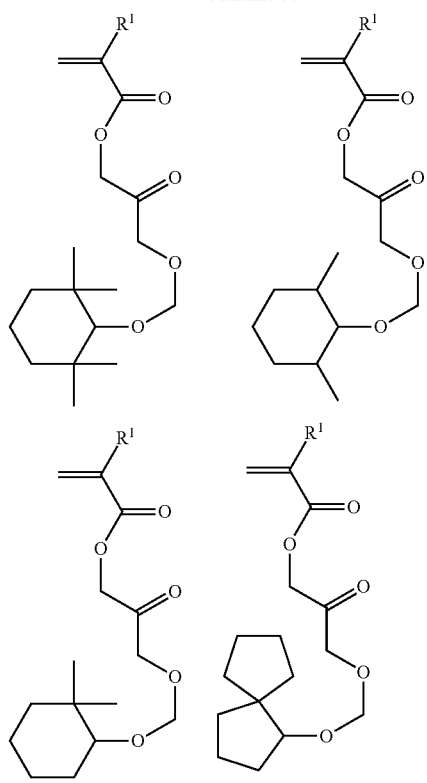
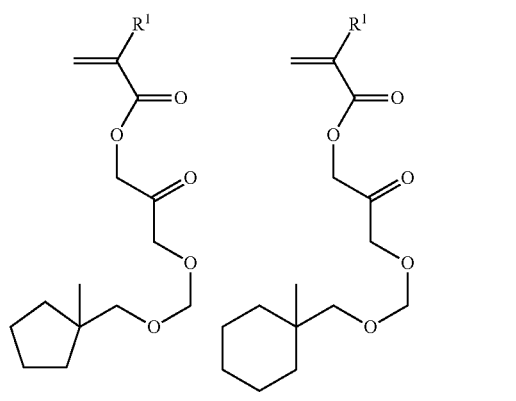
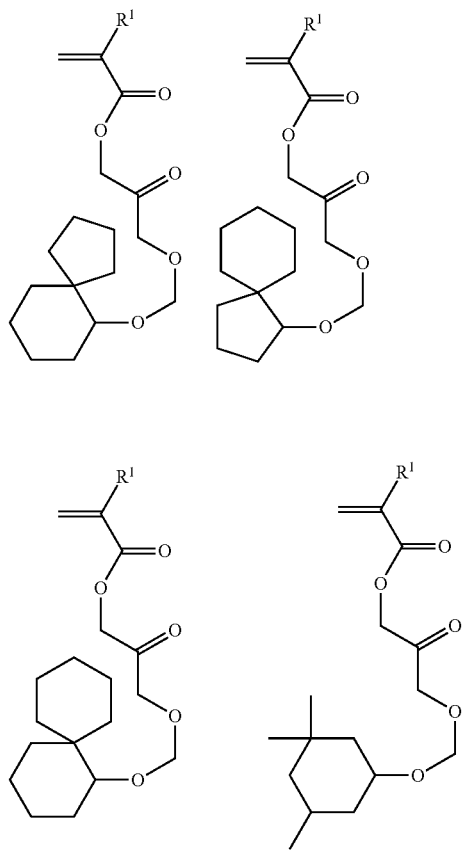

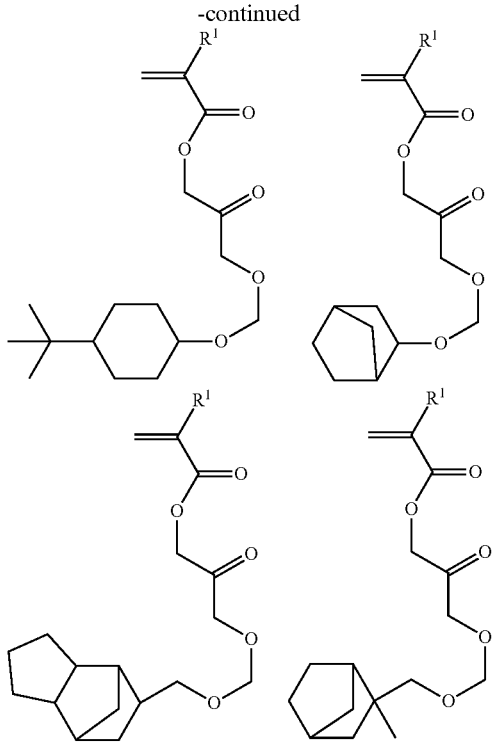
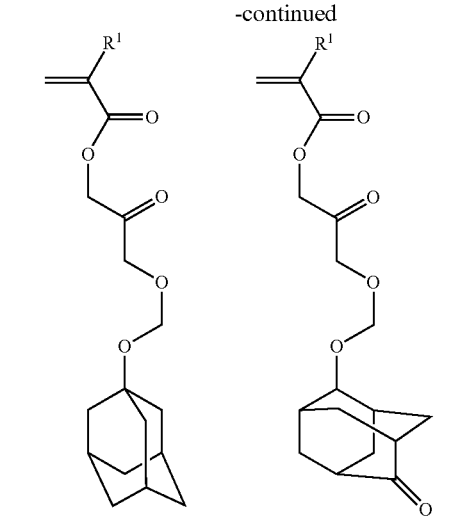
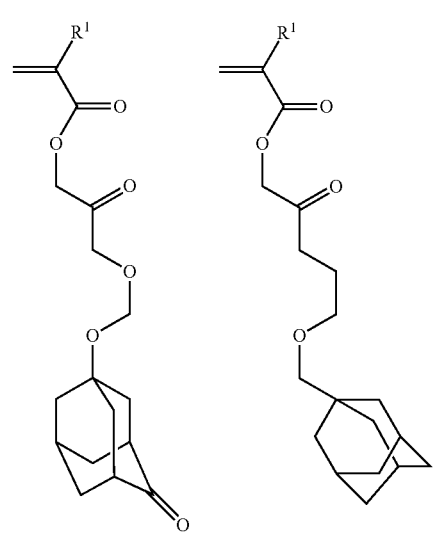
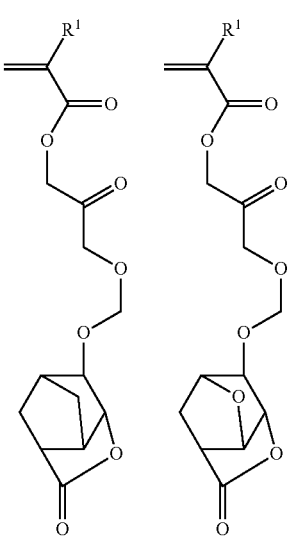

-continued
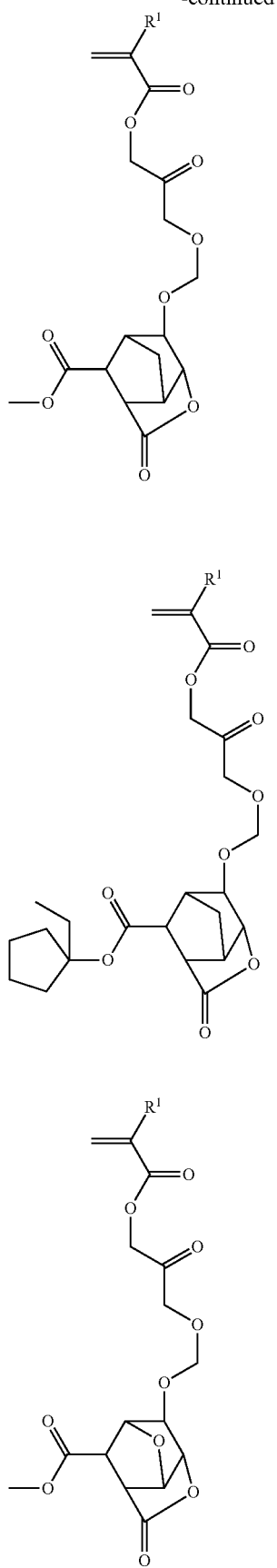
-continued
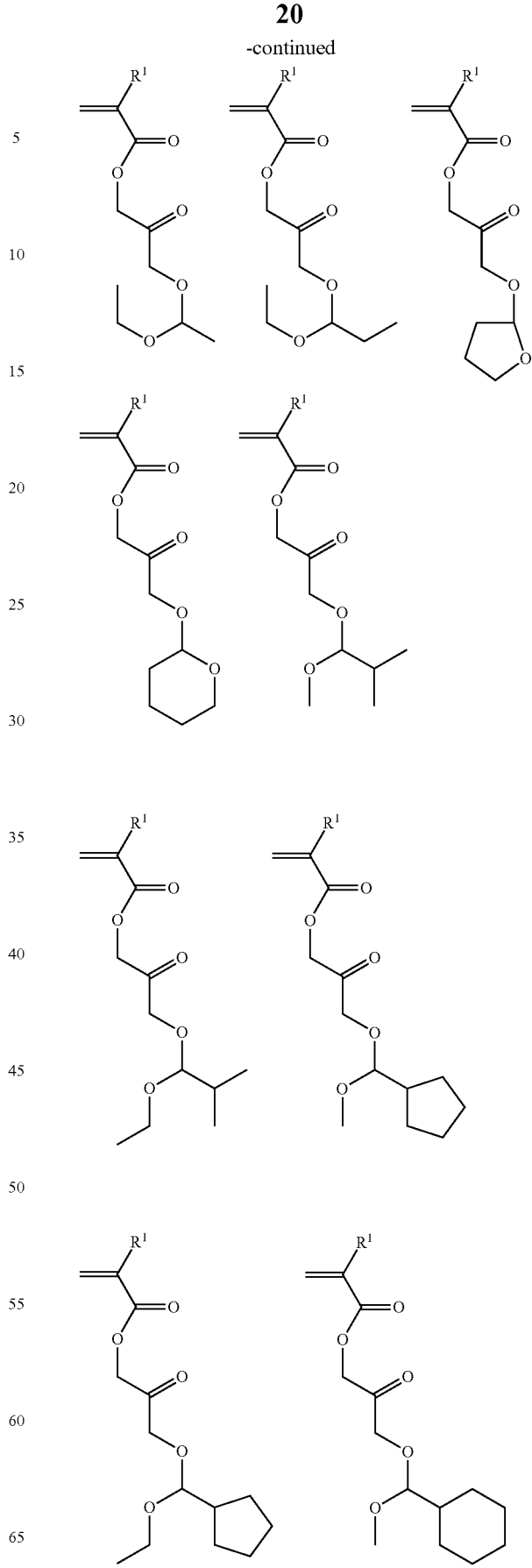

-continued
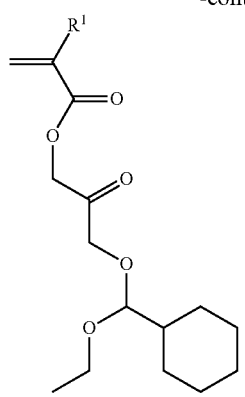
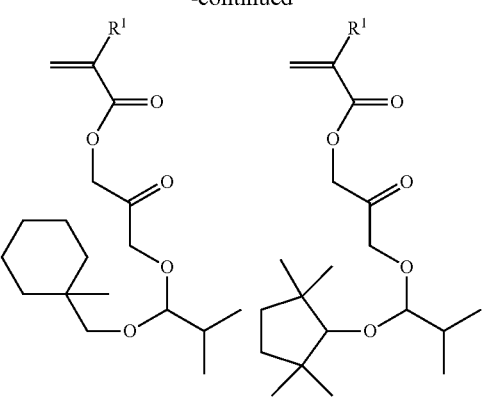
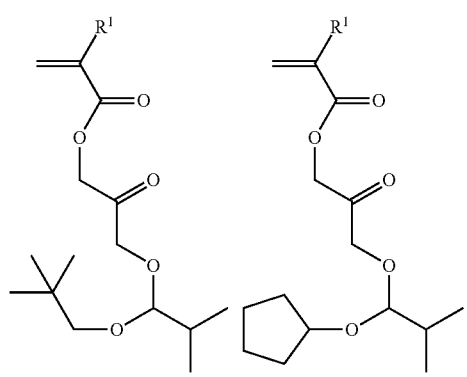
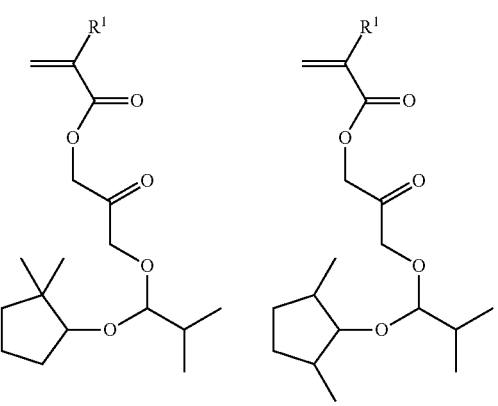
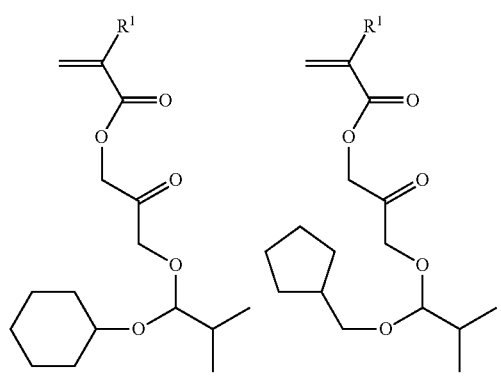
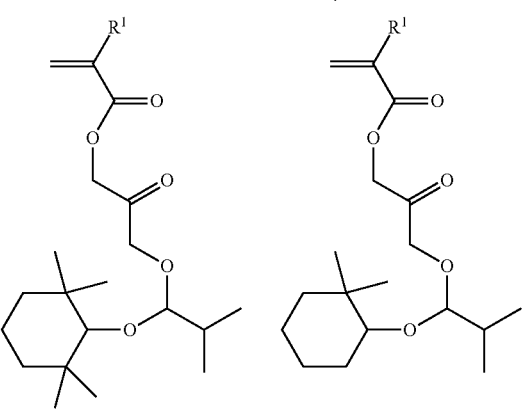
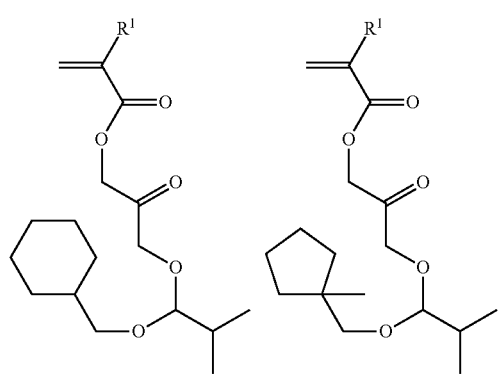
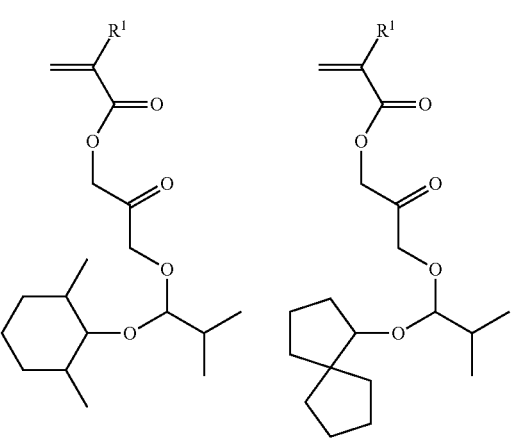

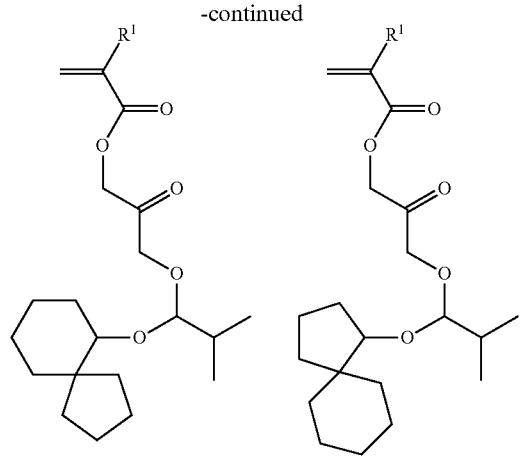
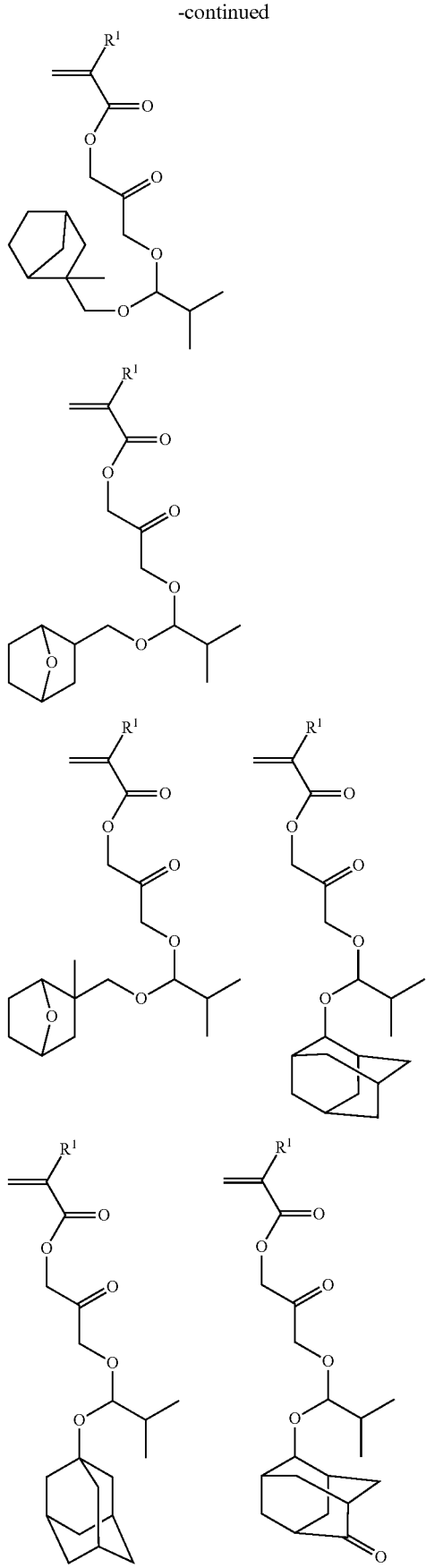

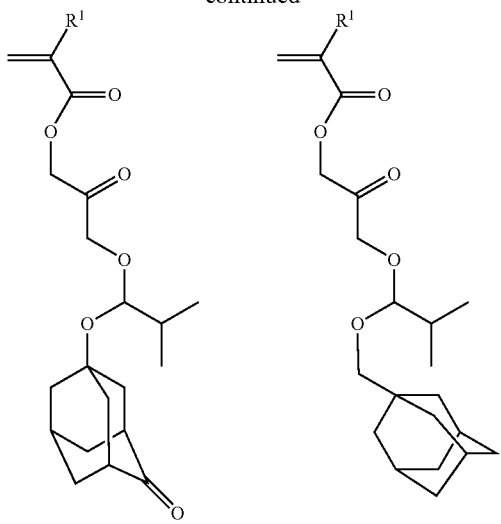
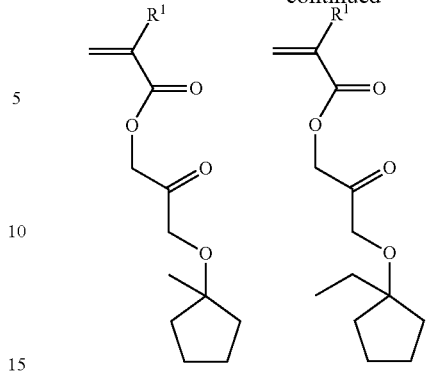

The monomer of formula (1) wherein $R^2$ is other than hydrogen may be prepared, for example, via steps i) to iii) according to the reaction scheme shown below although the synthesis route is not limited thereto. It is noted that the monomer of formula (1) wherein $R^2$ is hydrogen corresponds to compound (8) shown below.

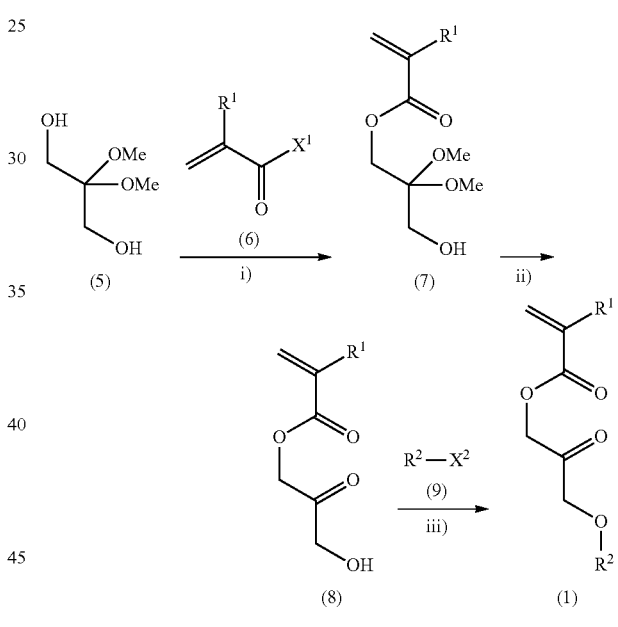

Herein Me is methyl. $R^1$ and $R^2$ are as defined above. $X^1$ is a halogen atom, hydroxyl group or $-OR^5$ wherein $R^5$ is methyl, ethyl or a group of the following formula (10).

$X^2$ is a halogen atom.

Step i) is a reaction of diol compound (5) with esterifying agent (6) to form hydroxy-ester compound (7). One reactant, diol compound (5) may be readily synthesized by the method described in Journal of Organic Chemistry Vol. 64, p. 4943 (1999).

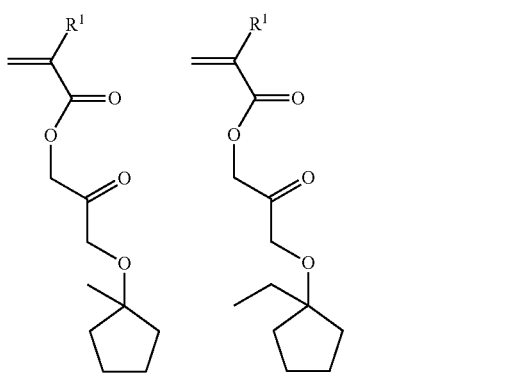

The reaction may readily run by a well-known procedure. The preferred esterifying agent (6) is an acid chloride of formula (6) wherein $X^1$ is chlorine or a carboxylic anhydride of formula (6) wherein $X^1$ is —$OR^5$ and $R^5$ is a group of formula (10). When an acid chloride, typically carboxylic acid chloride such as methacrylic acid chloride is used as the esterifying agent (6), the reaction may be conducted in a solventless system or in a solvent (e.g., methylene chloride, acetonitrile, toluene or hexane) by adding diol compound (5), acid chloride, and a base (e.g., triethylamine, pyridine or 4-dimethylaminopyridine) in sequence or at the same time, and optional cooling or heating. When a carboxylic anhydride such as methacrylic anhydride is used as the esterifying agent (6), the reaction may be conducted in a solventless system or in a solvent (e.g., methylene chloride, acetonitrile, toluene or hexane) by adding diol compound (5), carboxylic anhydride, and a base (e.g., triethylamine, pyridine or 4-dimethylaminopyridine) in sequence or at the same time, and optional cooling or heating.

An appropriate amount of diol compound (5) used is 1 to 10 moles, more preferably 1 to 5 moles per mole of esterifying agent (6). Less than 1 mole of diol compound (5) may result in a substantial drop of percent yield because a noticeable amount of a bis-ester compound may be formed by side reaction to esterify both the hydroxyl groups of diol compound (5). More than 10 moles of diol compound (5) may be uneconomical because of an increase of reactant cost and a lowering of pot yield.

The reaction time is determined as appropriate by monitoring the reaction process by thin-layer chromatography (TLC) or gas chromatography (GC) because it is desirable from the yield aspect to drive the reaction to completion. Usually the reaction time is about 30 minutes to about 40 hours. Hydroxy-ester compound (7) may be recovered from the reaction mixture by ordinary aqueous work-up. If necessary, the compound may be purified by standard techniques like distillation, recrystallization and chromatography.

Step ii) is hydrolysis of dimethylacetal group of hydroxy-ester compound (7) under acidic conditions to form hydroxy-keto-ester compound (8). The reaction may readily run by a well-known procedure. Preferably an acid catalyst is used. Suitable acid catalysts include mineral acids such as hydrochloric acid, sulfuric acid, nitric acid and perchloric acid and organic acids such as p-toluenesulfonic acid and benzenesulfonic acid.

Step iii) is a reaction of hydroxy-keto-ester compound (8) with protecting agent (9) to form the desired monomer (1). The protecting agent (9) has the formula: $R^2$—$X^2$ wherein $R^2$ is as defined above and $X^2$ is a halogen. Exemplary halogen atoms are chlorine, bromine and iodine, with chlorine being most preferred for ease of handling.

The reaction may readily run by a well-known procedure. Where $R^2$ in formula (1) is a group of the following formula (11), that is, the protecting agent (9) has the following formula (12):

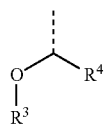

(11)

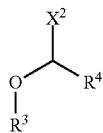

(12)

wherein $R^3$, $R^4$ and $X^2$ are as defined above, preferably the reaction may be conducted in a solventless system or in a solvent by adding hydroxy-keto-ester compound (8), protecting agent (9), and a base (e.g., triethylamine, pyridine, N,N-diisopropylethylamine or 4-dimethylaminopyridine) in sequence or at the same time, and optional cooling or heating.

An appropriate amount of protecting agent (9) used is 0.5 to 10 moles, more preferably 1.0 to 3.0 moles per mole of hydroxy-keto-ester compound (8). Less than 0.5 mole of protecting agent (9) may result in a substantial drop of percent yield because a large fraction of the reactant may be left unreacted. More than 10 moles of protecting agent (9) may be uneconomical because of an increase of reactant cost and a lowering of pot yield.

Suitable solvents used in step iii) include hydrocarbons such as toluene, xylene, hexane, and heptane; chlorinated solvents such as methylene chloride, chloroform and dichloroethane; ethers such as diethyl ether, tetrahydrofuran and dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide, N,N-dimethylacetamide and dimethyl sulfoxide; and water, which may be used alone or in admixture. To the reaction system, a phase transfer catalyst such as tetrabutylammonium hydrogensulfate may be added. An appropriate amount of the phase transfer catalyst, if used, is 0.0001 to 1.0 mole, more preferably 0.001 to 0.5 mole per mole of hydroxy-keto-ester compound (8). Less than 0.0001 mole of the catalyst may fail to achieve an addition effect whereas more than 1.0 mole of the catalyst may be uneconomical because of an increased catalyst cost.

The reaction time is determined as appropriate by monitoring the reaction process by TLC or GC because it is desirable from the yield aspect to drive the reaction to completion. Usually the reaction time is about 30 minutes to about 40 hours. The monomer (1) may be recovered from the reaction mixture by ordinary aqueous work-up. If necessary, the monomer may be purified by standard techniques like distillation, recrystallization and chromatography.

When it is desired to obtain monomer (1) wherein substituent $R^2$ is tertiary alkyl or $R^2$ is a group of formula (11) wherein $R^3$ and $R^4$ bond together to form a 5- or 6-membered ring with the carbon and oxygen atoms to which they are attached, step iii) may follow an alternative route, that is, addition reaction of an olefin corresponding to an alcohol compound $R^2$—OH with the water molecule eliminated therefrom and hydroxy-keto-ester compound (8) in the presence of an acid catalyst. The reaction may be conducted in a solventless system or in a solvent (e.g., toluene, hexane, methylene chloride or dichloromethane) by stirring the olefin and hydroxy-keto-ester compound (8) in the presence of an acid catalyst and optional cooling or heating. Suitable acid catalysts include mineral acids such as hydrochloric acid, sulfuric acid, nitric acid and perchloric acid, organic acids such as p-toluenesulfonic acid, benzenesulfonic acid, methanesulfonic acid and trifluoroacetic acid, and solid acid catalysts such as Amberlyst® (Rohm & Haas Co.).

Polymer

A third embodiment of the invention is a polymer or high-molecular-weight compound comprising recurring units derived from the monomer having formula (1) or (2) defined above.

Specifically, the recurring units derived from the monomer having formula (1) or (2) are units having the general formula (3a) or (3b).

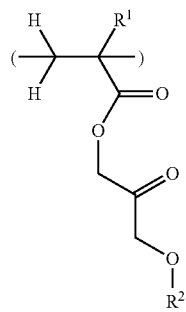
(3a)

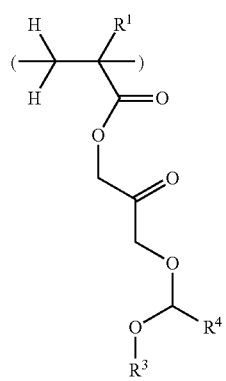
(3b)

Herein $R^1$ is hydrogen, methyl or trifluoromethyl, $R^2$ is hydrogen or an acid labile group, $R^3$ is a straight, branched or cyclic, monovalent hydrocarbon group of 1 to 20 carbon atoms in which a constituent —$CH_2$— may be substituted by —O— or —C(=O)—, $R^4$ is hydrogen or a straight, branched or cyclic, monovalent hydrocarbon group of 1 to 20 carbon atoms, $R^3$ and $R'$ may bond together to form a 5 or 6-membered ring with the carbon and oxygen atoms to which they are attached.

It is believed that in a resist composition comprising the inventive polymer as base resin, reactions take place according to the scheme shown below. In step A), deprotection of $R^2$ group takes place by reaction with an acid generated during exposure to high-energy radiation and bake. In step B), hydroxy-ketone units resulting from deprotection of $R^2$ group join together to form a cyclic acetal structure, whereby crosslinking reaction takes place between different polymer chains, for example. It is believed that either step A) or B) brings about a significant change in the solubility of the base resin in developer. Namely, the resist composition comprising the inventive polymer as base resin is expected to achieve a high dissolution contrast of the base resin before and after exposure, and improvements in resolution and roughness.

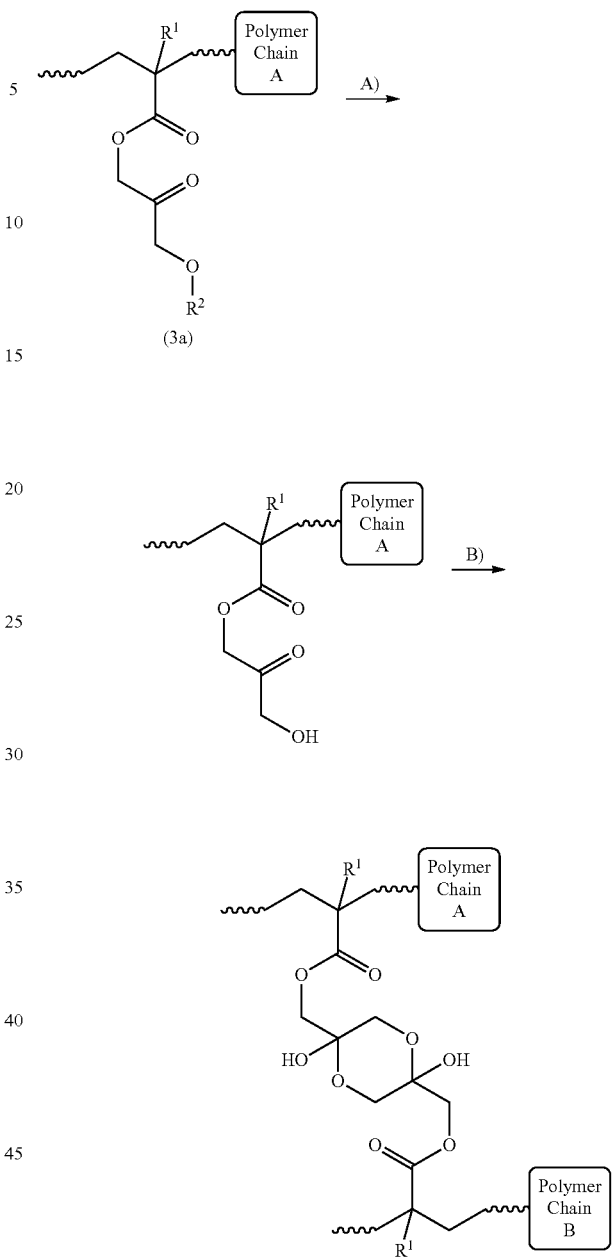

In addition to the units having formula (3a) and/or (3b), the preferred polymer may further comprise recurring units of at least one type selected from recurring units having the general formulae (4A) to (4E).

(4A)

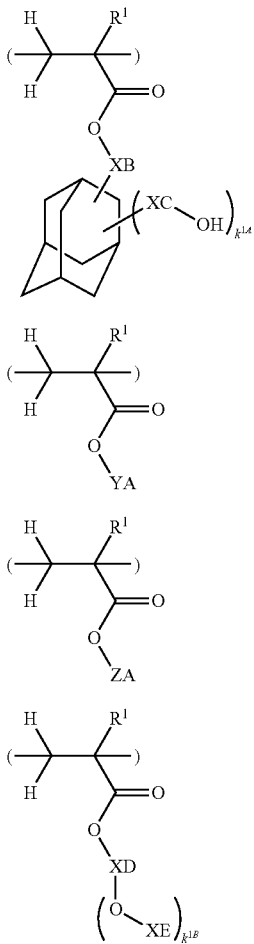

(4B)

(4C)

(4D)

(4E)

Herein $R^1$ is as defined above. XA is an acid labile group. XB and XC are each independently a single bond or a straight or branched, divalent hydrocarbon group of 1 to 4 carbon atoms. XD is a straight, branched or cyclic, di- to pentavalent aliphatic hydrocarbon group of 1 to 16 carbon atoms in which a constituent —CH$_2$— may be substituted by —O— or —C(=O)—. XE is an acid labile group. YA is a substituent group of lactone, sultone or carbonate structure. ZA is hydrogen, a fluoroalkyl group of 1 to 15 carbon atoms or a fluoroalcohol-containing group of 1 to 15 carbon atoms, $k^{1A}$ is an integer of 1 to 3, and $k^{1B}$ is an integer of 1 to 4.

A polymer comprising recurring units of formula (4A) is decomposed under the action of acid to generate carboxylic acid so that it may turn alkali soluble. The acid labile group XA may be selected from a variety of such groups. Examples of the acid labile group are groups of the following general formulae (L1) to (L4), tertiary alkyl groups of 4 to 20 carbon atoms, preferably 4 to 15 carbon atoms, trialkyl-silyl groups in which each alkyl moiety has 1 to 6 carbon atoms, and oxoalkyl groups of 4 to 20 carbon atoms.

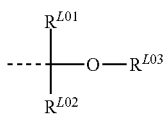

(L1)

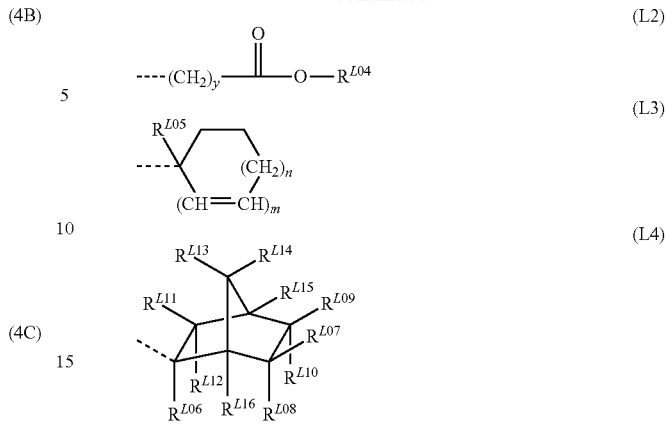

Herein $R^{L01}$ and $R^{L02}$ are each independently hydrogen or a straight, branched or cyclic alkyl group of 1 to 18 carbon atoms, preferably 1 to 10 carbon atoms. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). $R^{L05}$ is an optionally substituted, straight, branched or cyclic $C_1$-$C_{10}$ alkyl group or an optionally substituted $C_6$-$C_{20}$ aryl group. $R^{L06}$ is an optionally substituted, straight, branched or cyclic $C_1$-$C_{10}$ alkyl group or an optionally substituted $C_6$-$C_{20}$ aryl group. $R^{L07}$ to $R^{L16}$ independently represent hydrogen or optionally substituted monovalent hydrocarbon groups of 1 to 15 carbon atoms. Letter y is an integer of 0 to 6, m is equal to 0 or 1, n is equal to 0, 1, 2 or 3, and 2 m+n is equal to 2 or 3. The broken line denotes a valence bond.

In formula (L1), exemplary groups of $R^{L01}$ and $R^{L02}$ include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a heteroatom such as oxygen, examples of which include straight, branched or cyclic alkyl groups, substituted forms of such alkyl groups in which some hydrogen atoms are replaced by hydroxyl, alkoxy, oxo, amino, alkylamino or the like, and similar groups which are separated by ether oxygen. Illustrative examples of the straight, branched or cyclic alkyl groups are as exemplified above for $R^{L01}$ and $R^{L02}$, and examples of the substituted alkyl groups are as shown below.

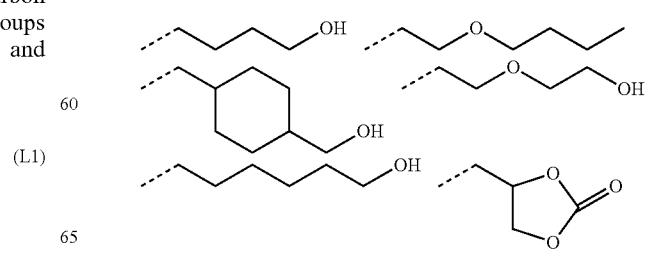

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of ring-forming $R^{L01}$, $R^{L02}$ and $R^{L03}$ is a straight or branched alkylene group of 1 to 18 carbon atoms, preferably 1 to 10 carbon atoms when they form a ring.

In formula (L2), exemplary tertiary alkyl groups of $R^{L04}$ are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl.

In formula (L3), examples of the optionally substituted $C_1$-$C_{10}$ alkyl groups of $R^{L05}$ include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxyl, alkoxycarbonyl, oxo, amino, alkylamino, cyano, mercapto, alkylthio, sulfo or other groups or in which a methylene moiety is replaced by an oxygen or sulfur atom. Examples of optionally substituted $C_6$-$C_{20}$ aryl groups include phenyl, methylphenyl, naphthyl, anthryl, phenanthryl, and pyrenyl.

In formula (L4), examples of optionally substituted, straight, branched or cyclic $C_1$-$C_{10}$ alkyl groups and optionally substituted $C_6$-$C_{20}$ aryl groups of $R^{L06}$ are the same as exemplified for Exemplary $C_1$-$C_{15}$ monovalent hydrocarbon groups of $R^{L07}$ to $R^{L16}$ include straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$ may bond together to form a ring with the carbon atom(s) to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$ form a ring). Each of $R^{L07}$ to $R^{L16}$ represents a $C_1$-$C_{15}$ divalent hydrocarbon group, typically alkylene, when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, or $R^{L13}$ and $R^{L15}$).

Of the acid labile groups of formula (L1), the straight and branched ones are exemplified by the following groups.

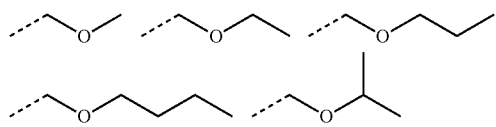

-continued

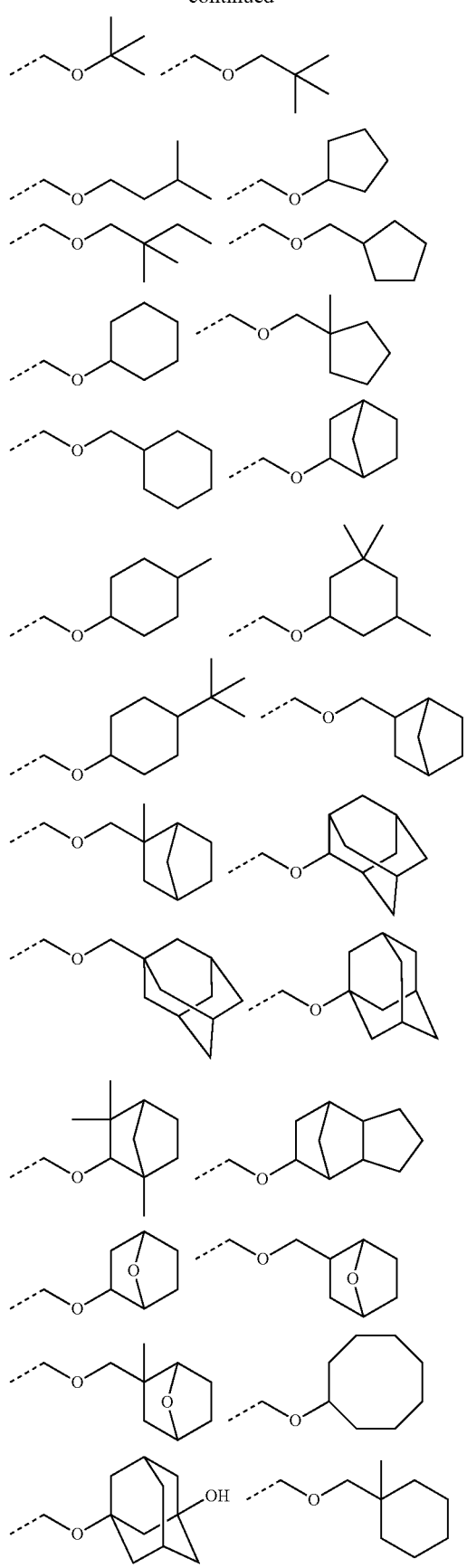

-continued

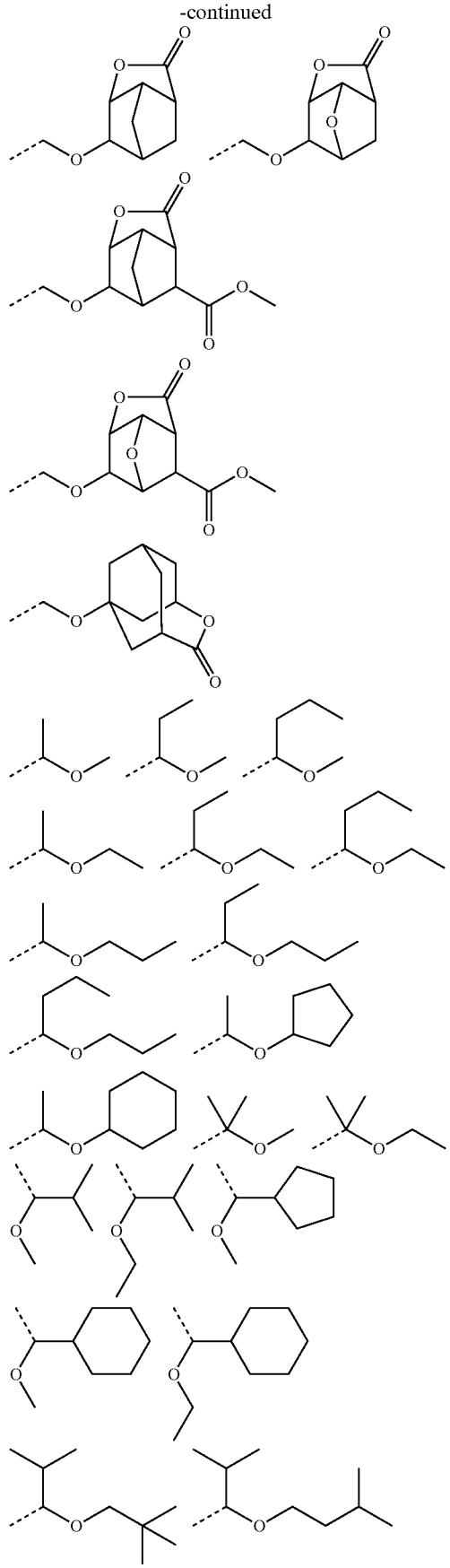

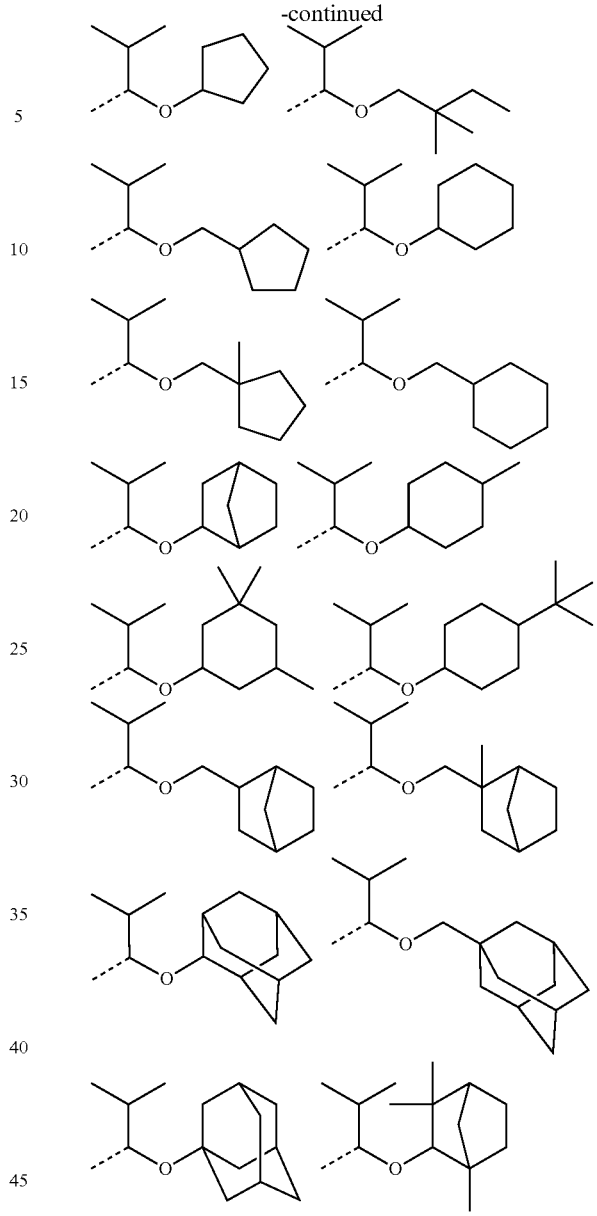

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

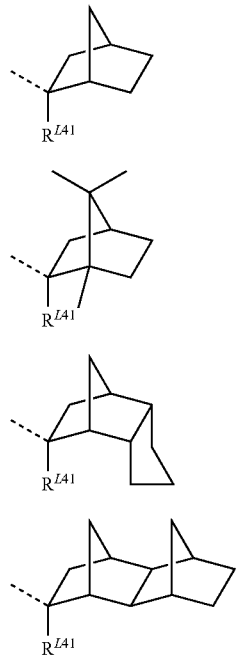

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

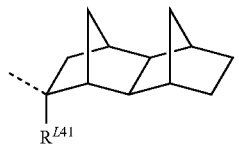

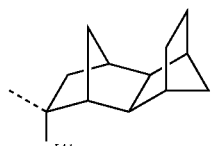

Note that $R^{L41}$ is as defined above.

Similarly, the general formula (L4-4) represents one or a mixture of two or more selected from groups having the following general formulas (L4-4-1) to (L4-4-4).

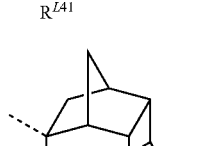

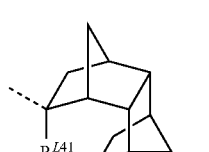

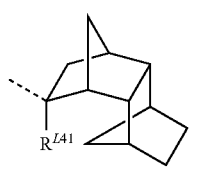

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

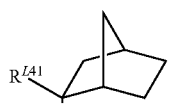

(L4-4-endo)

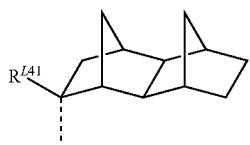

Note that $R^{L41}$ is as defined above.

Illustrative examples of the acid labile group of formula (L4) are given below.

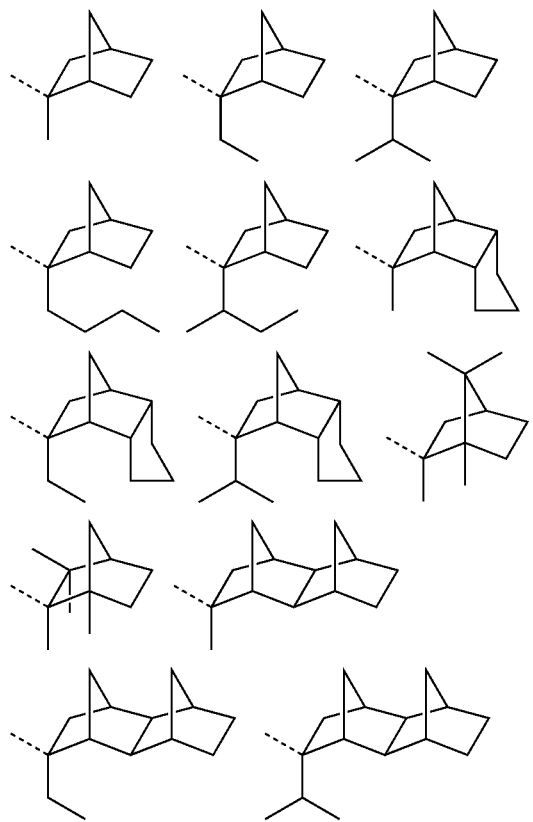

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by XA, are as exemplified for $R^{LO4}$ and the like.

Illustrative examples of the recurring units having formula (4A) are given below, but not limited thereto.

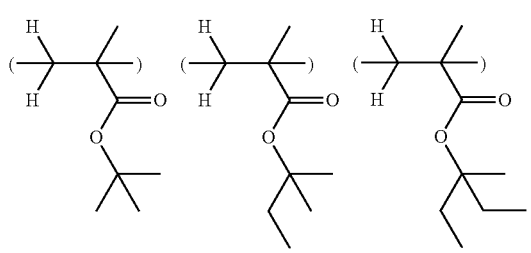

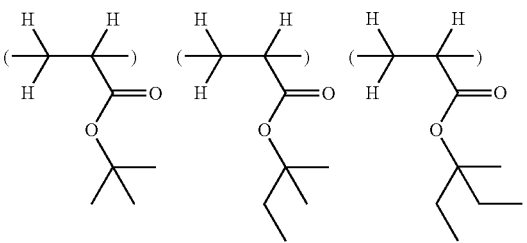

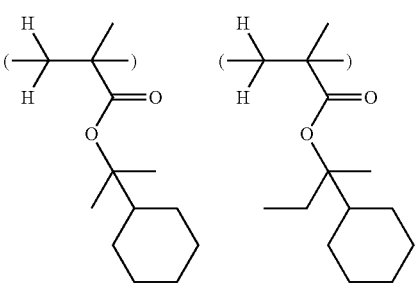

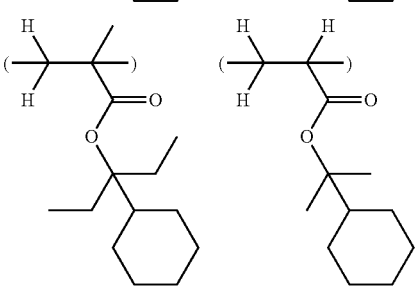

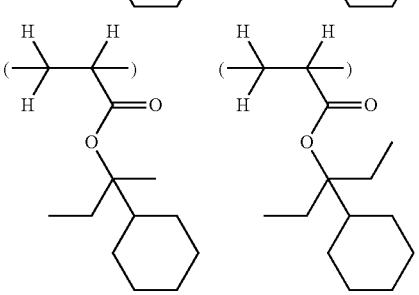

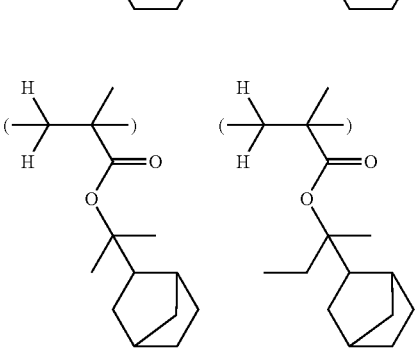

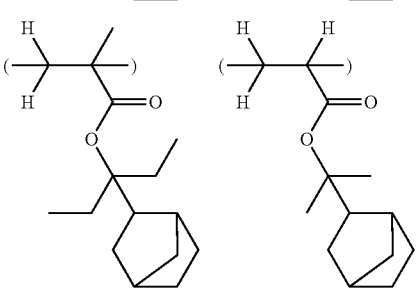

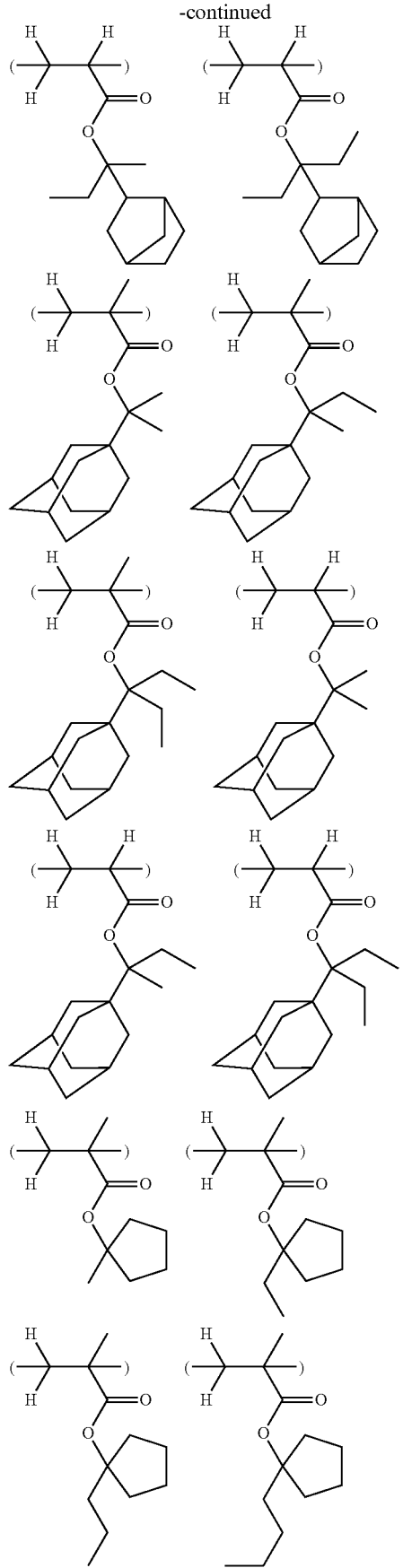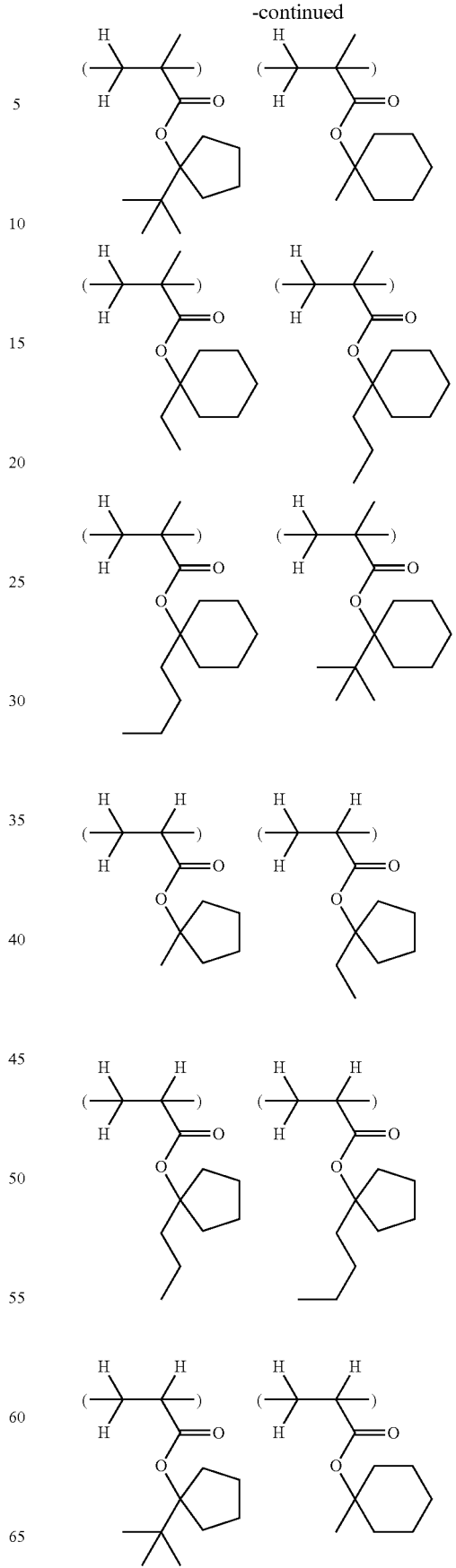

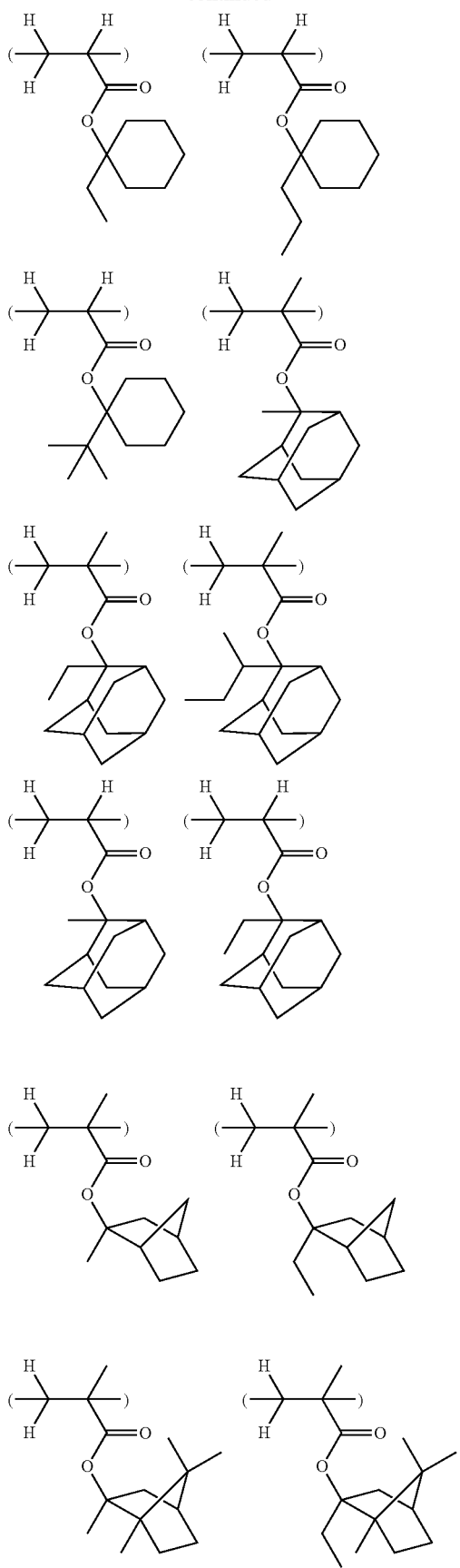
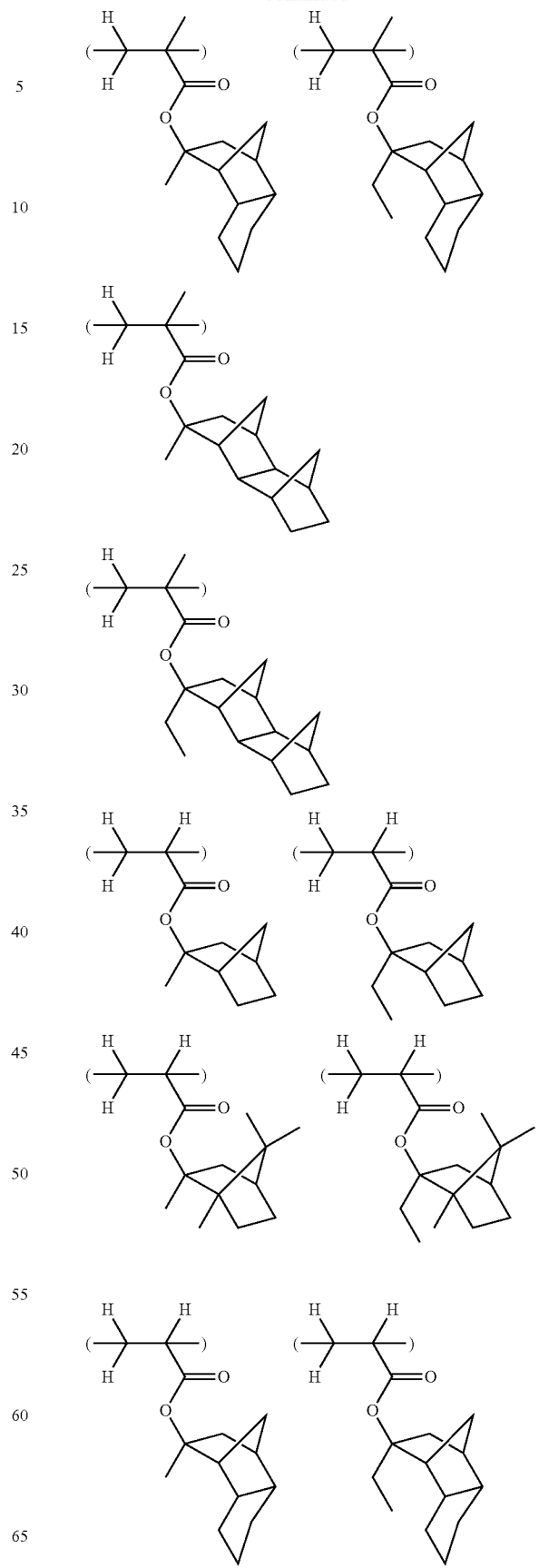

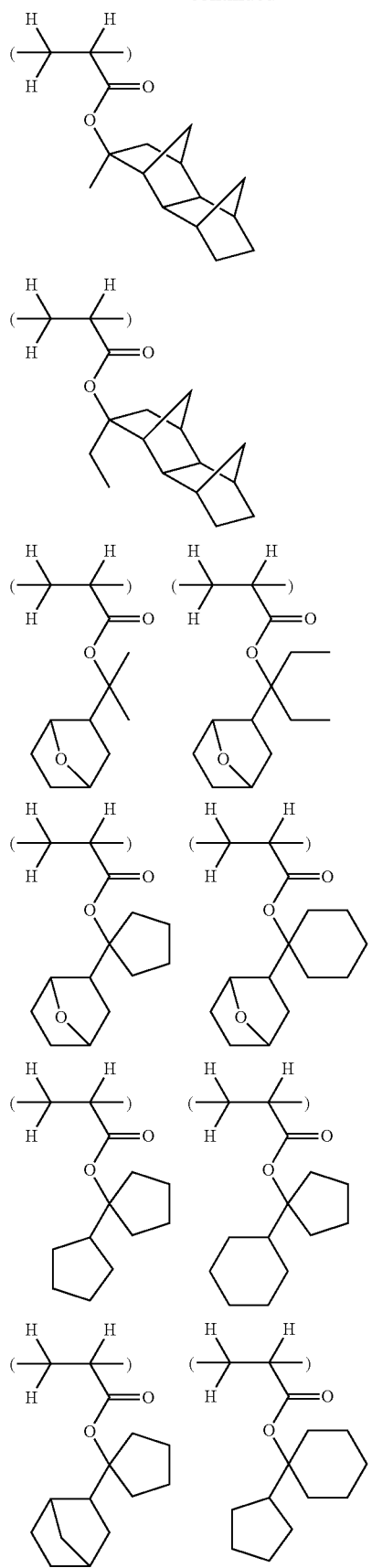
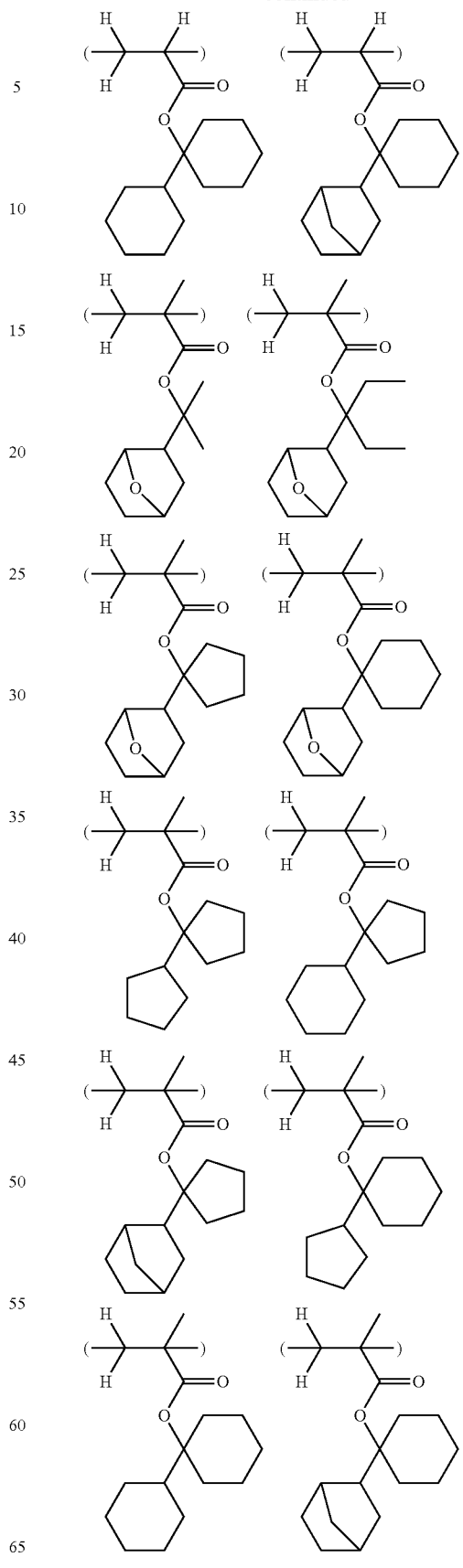

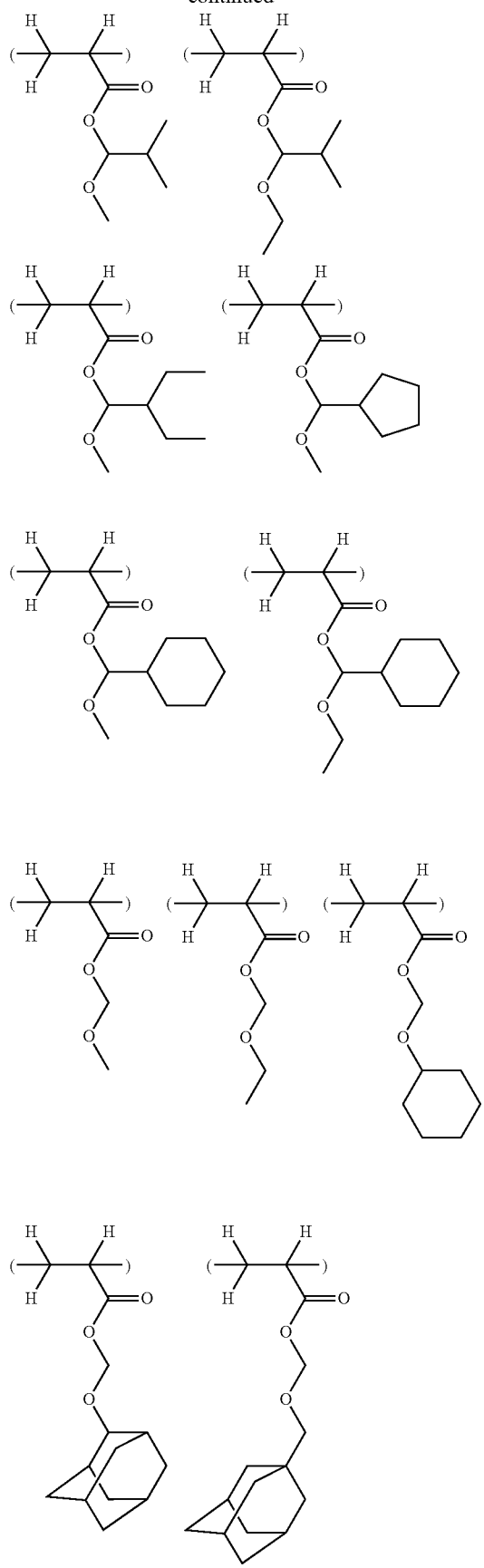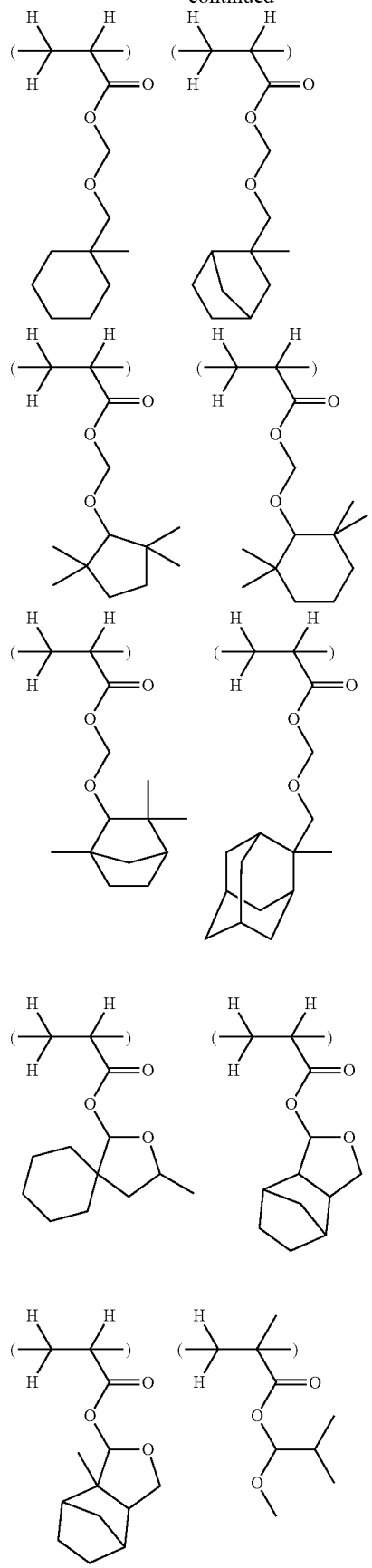

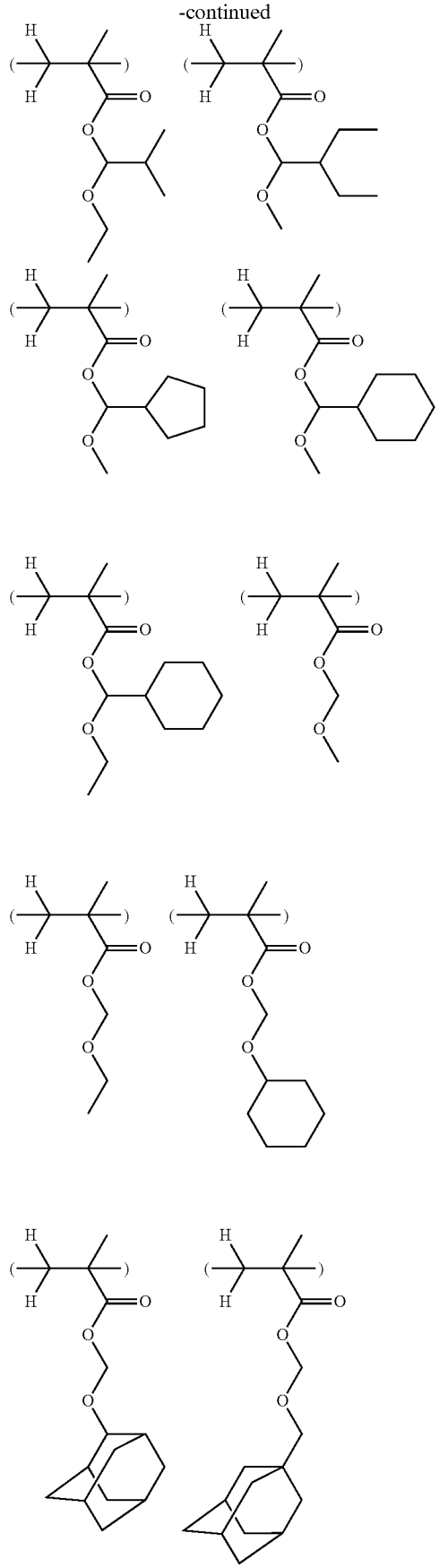
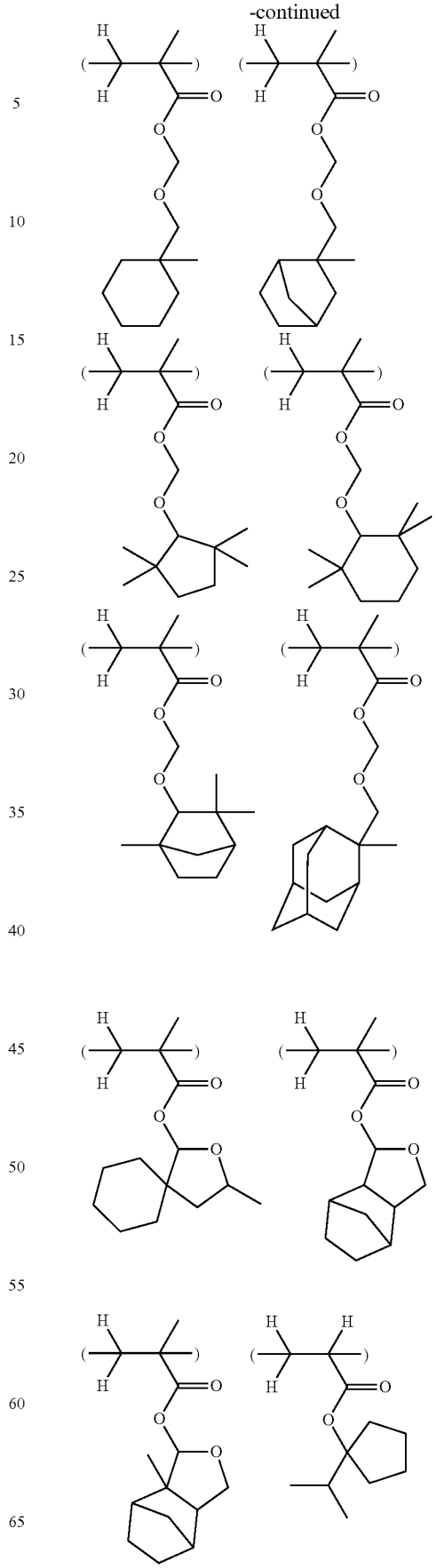

51
-continued
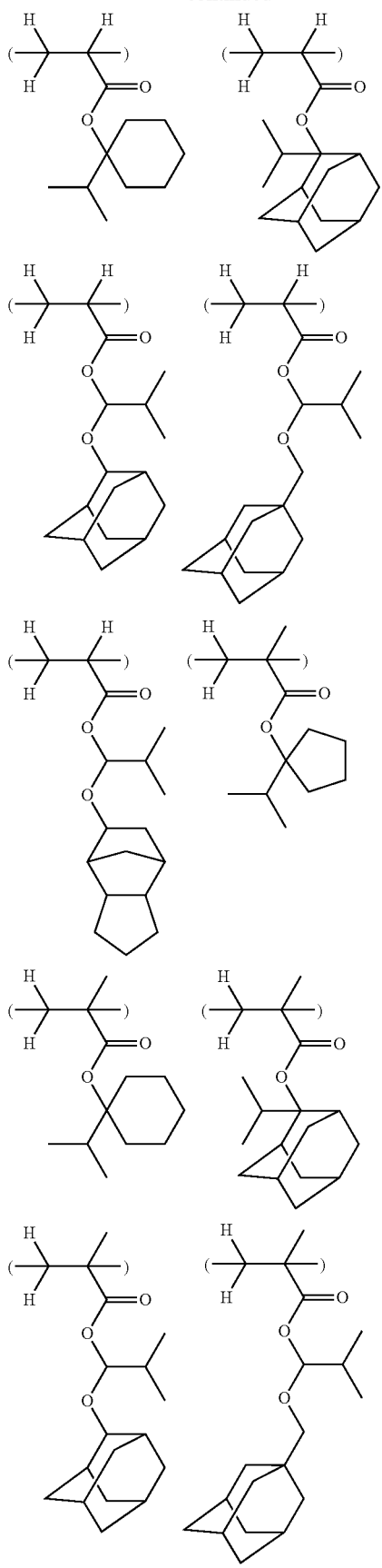
52
-continued
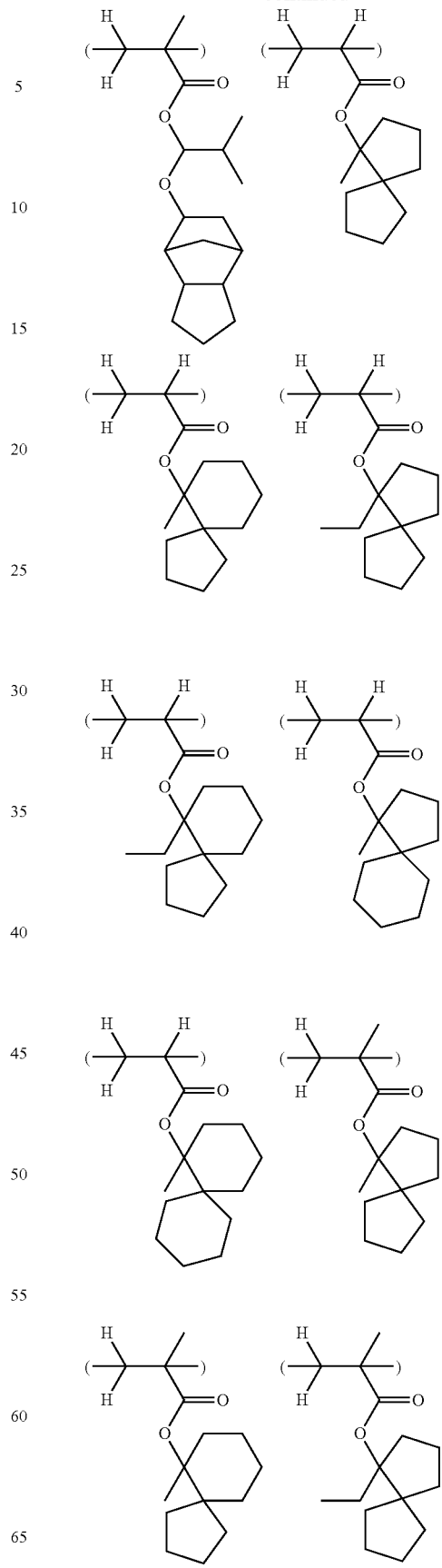

53
-continued
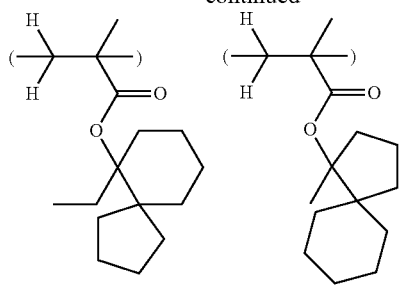
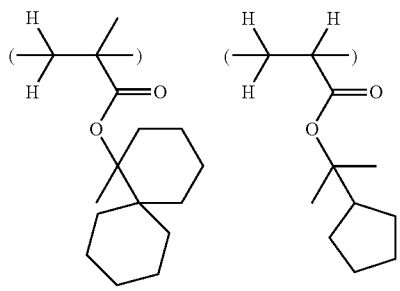
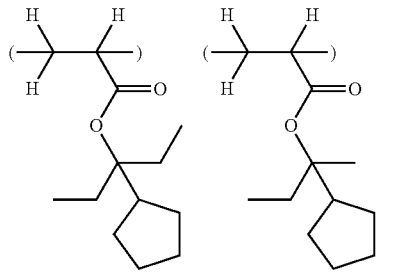
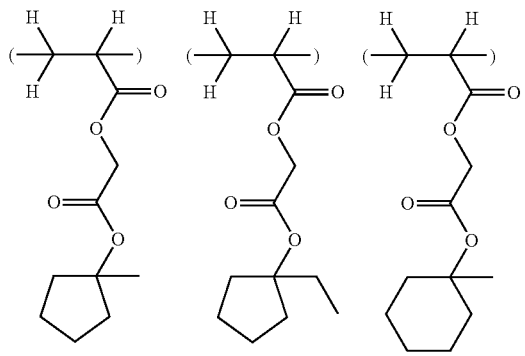
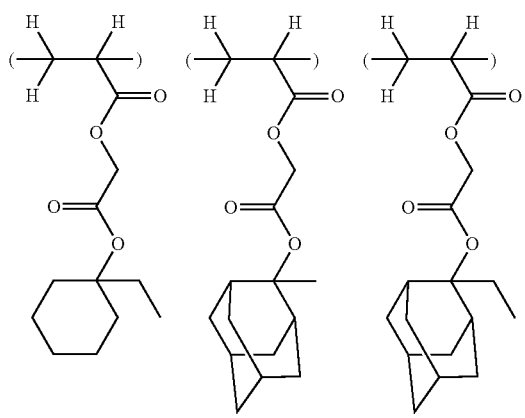
54
-continued
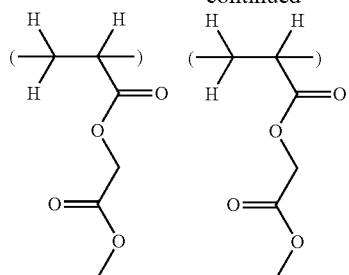
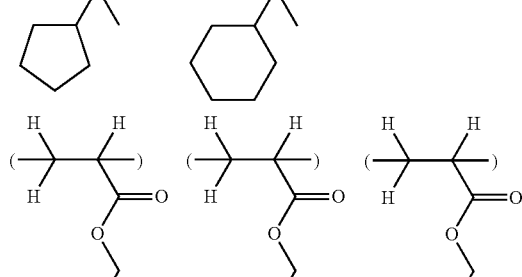
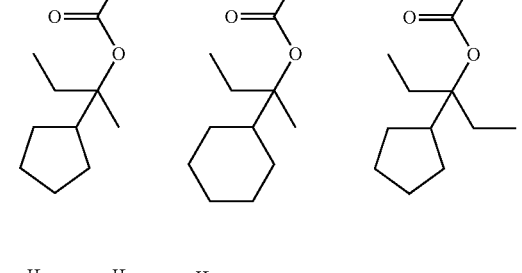
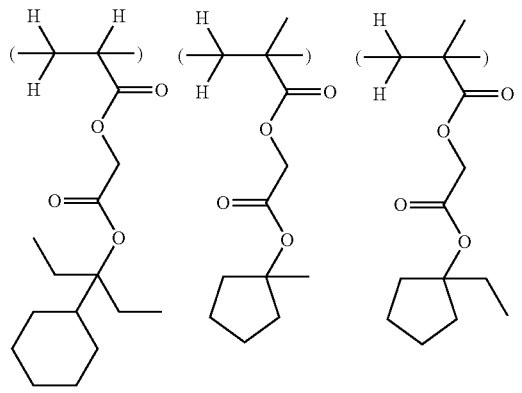
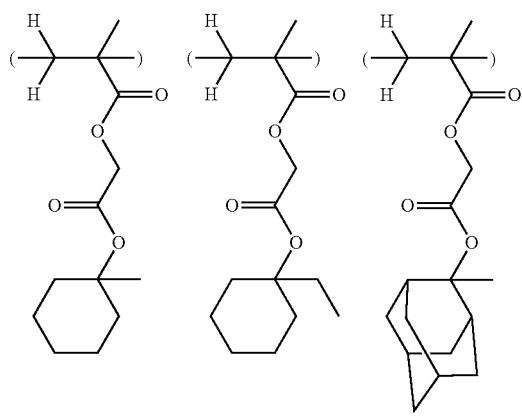

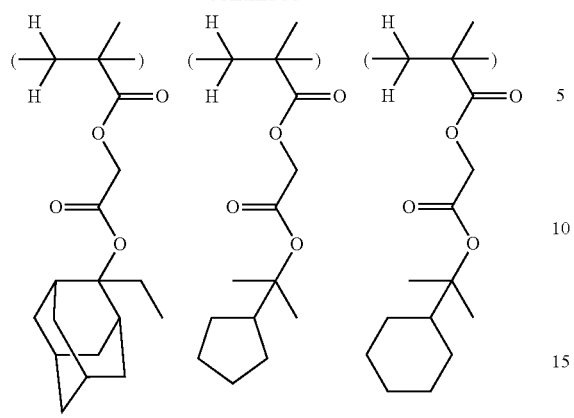
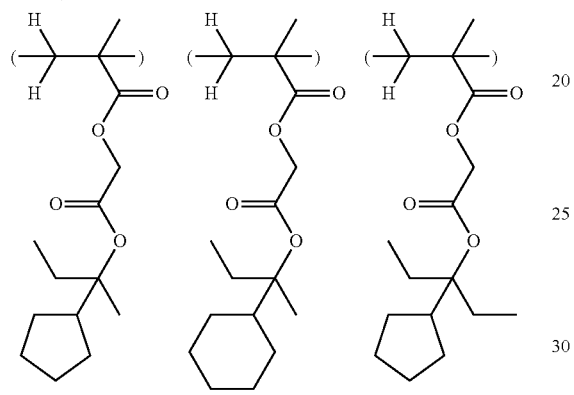
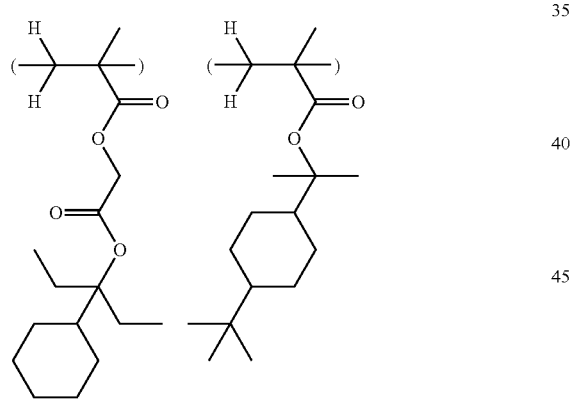
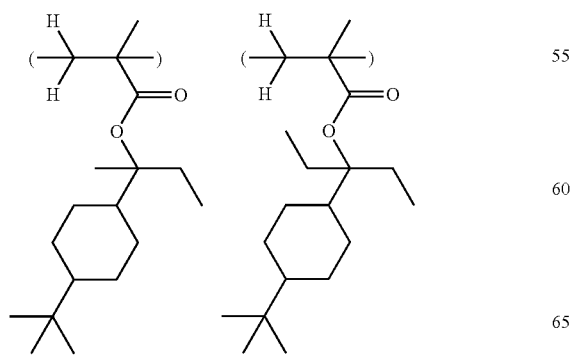
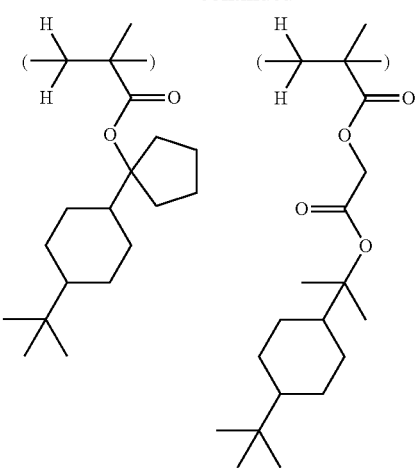
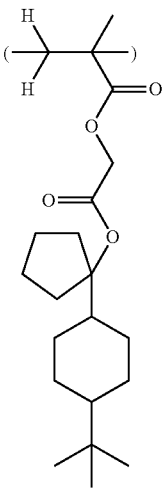
Illustrative examples of the recurring units having formula (4B) are given below, but not limited thereto.
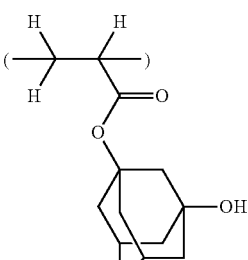
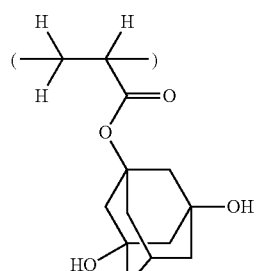
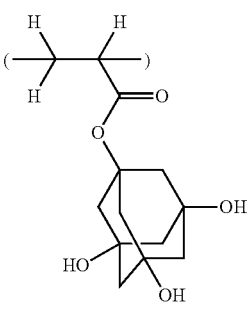

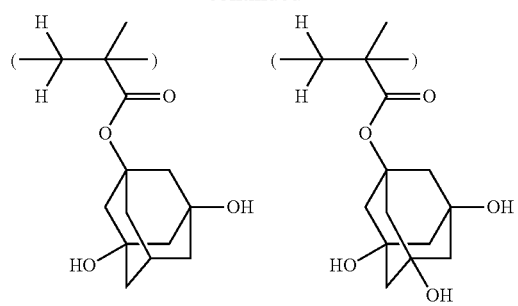
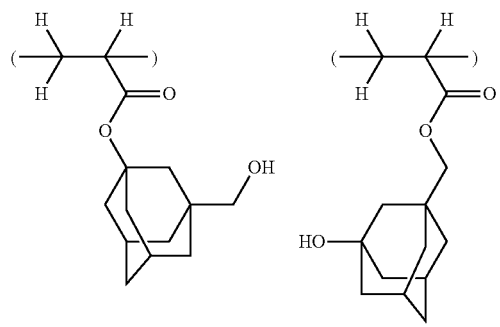
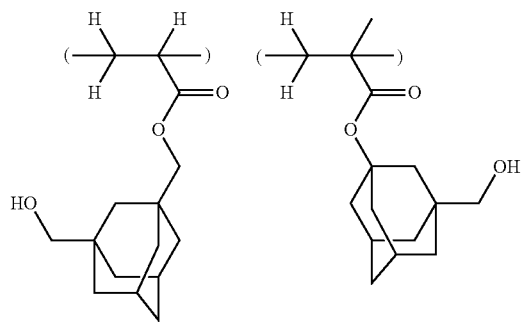
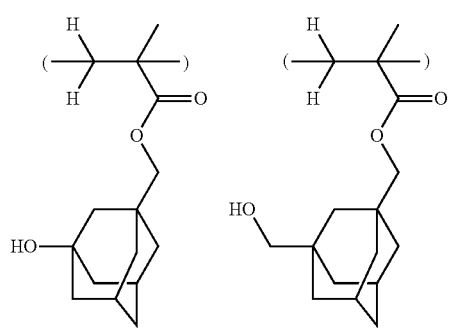
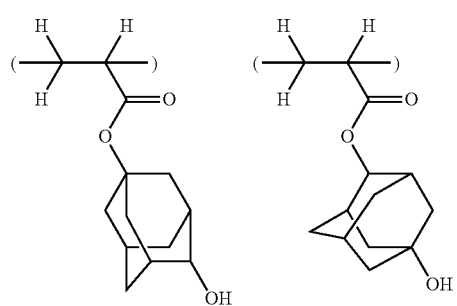
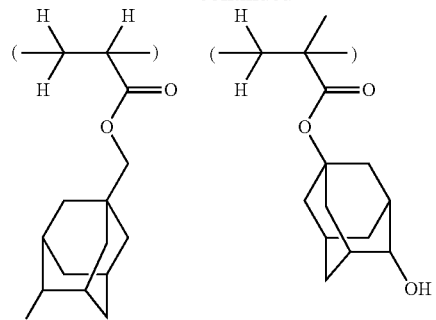
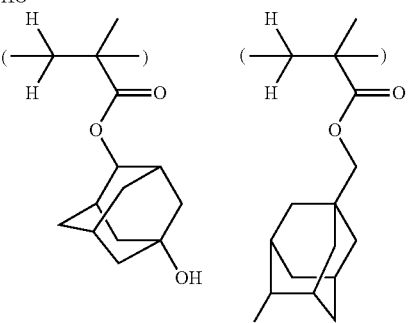
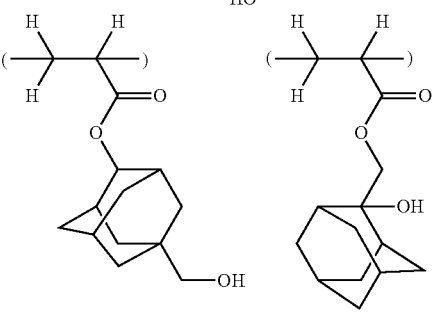
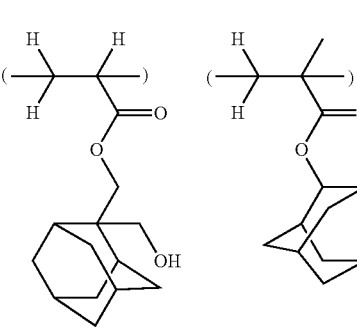
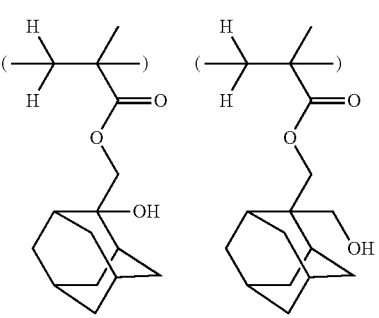

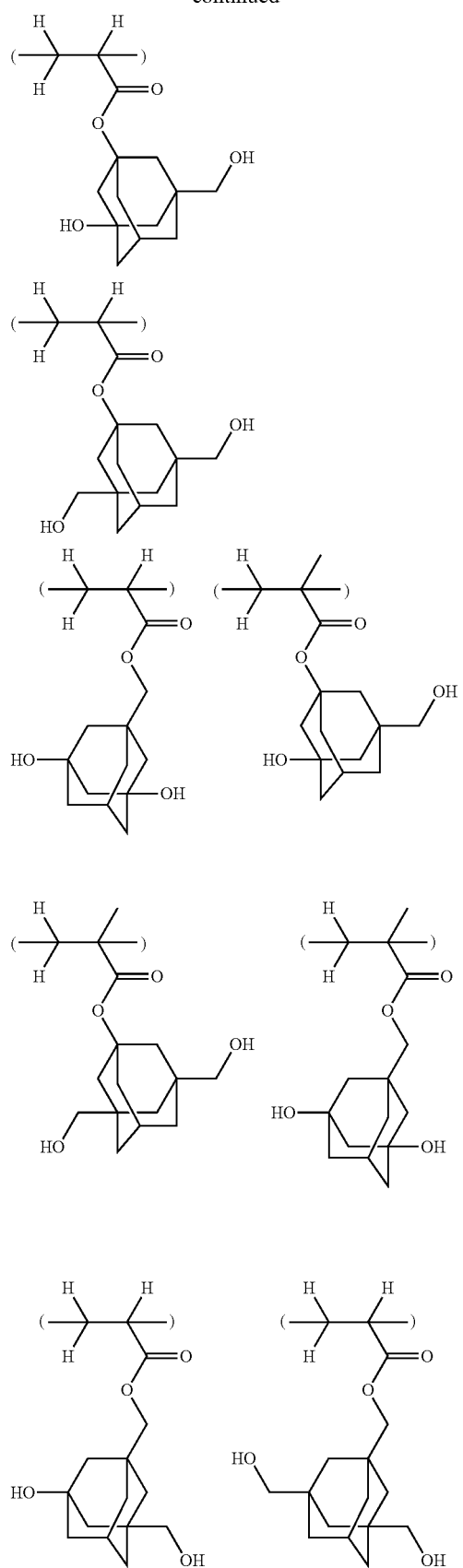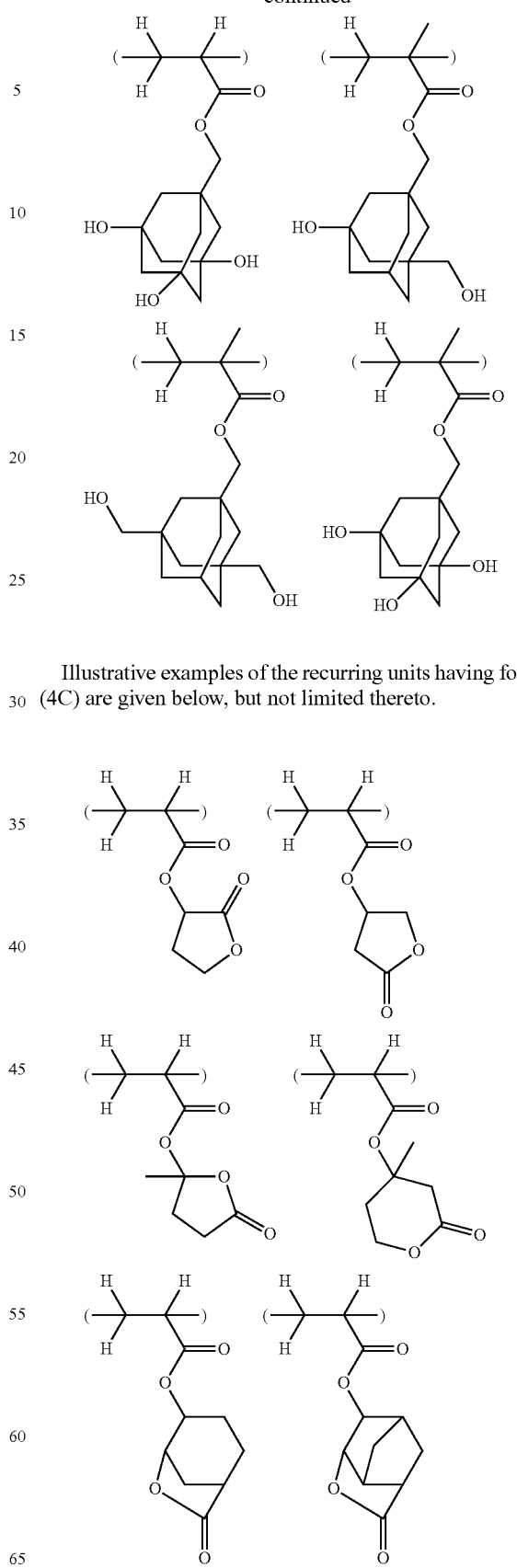
Illustrative examples of the recurring units having formula (4C) are given below, but not limited thereto.

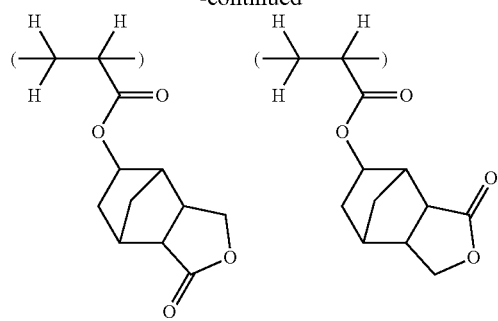
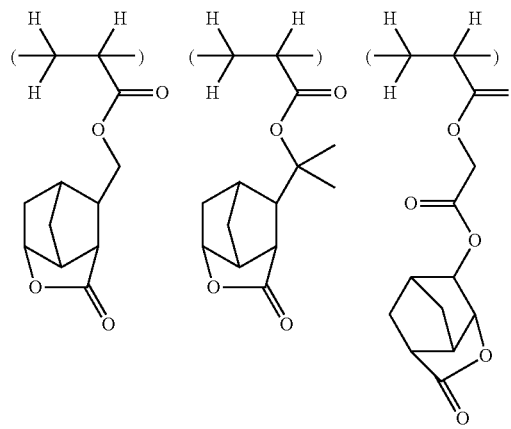
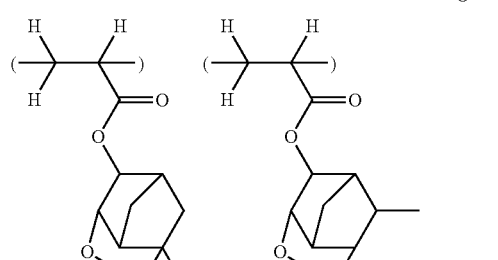
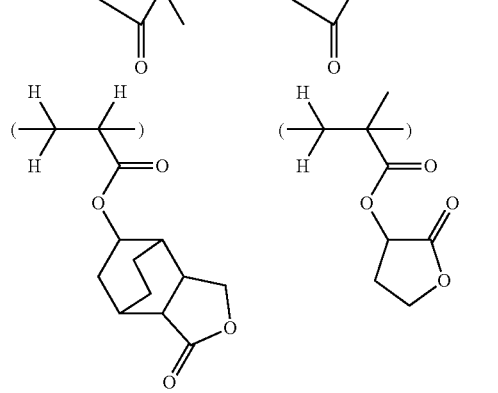
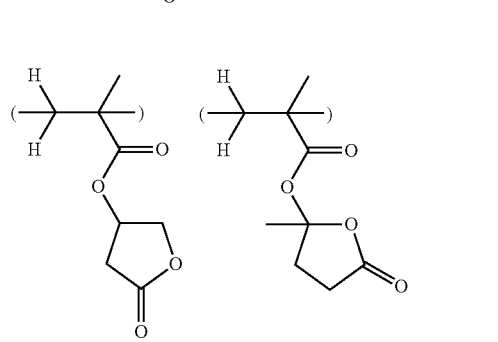
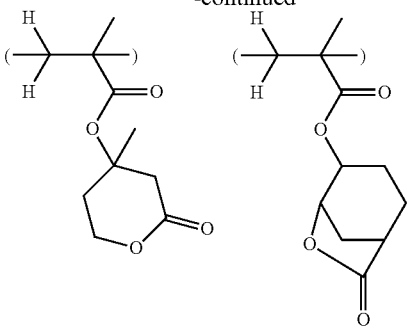
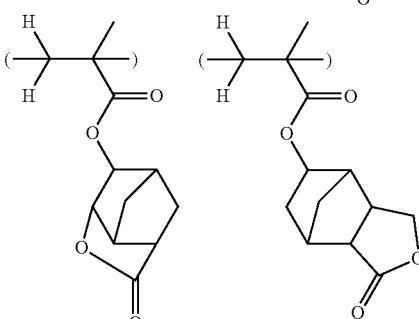
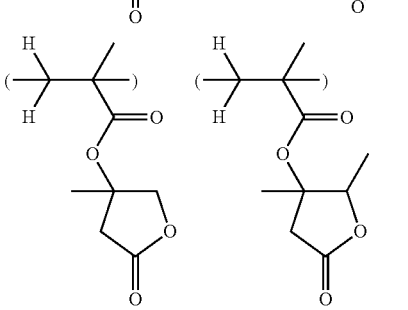
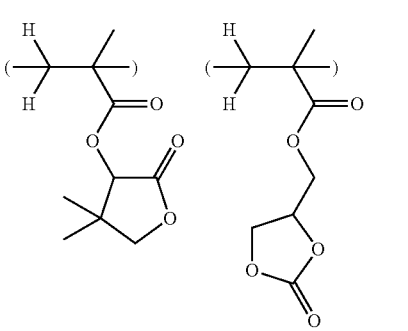
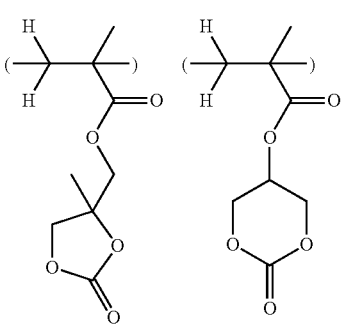

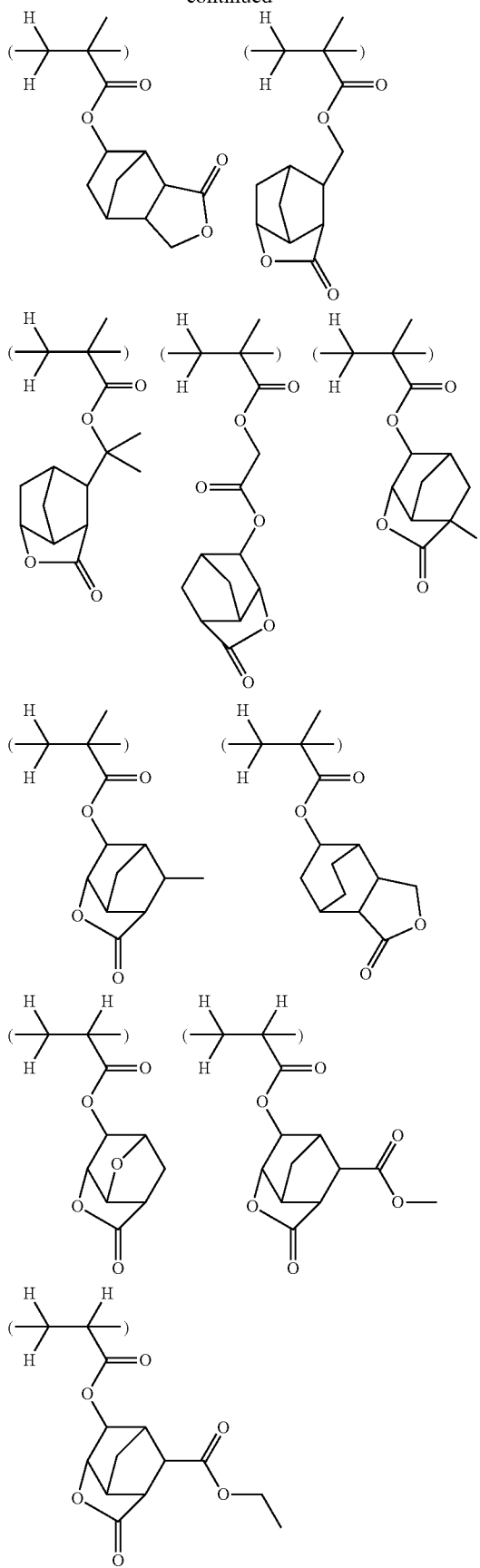
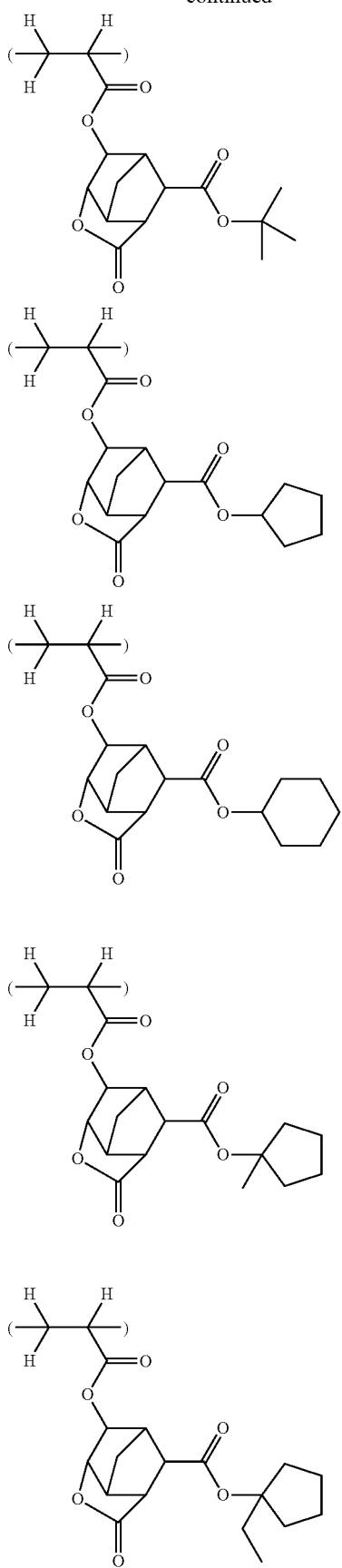

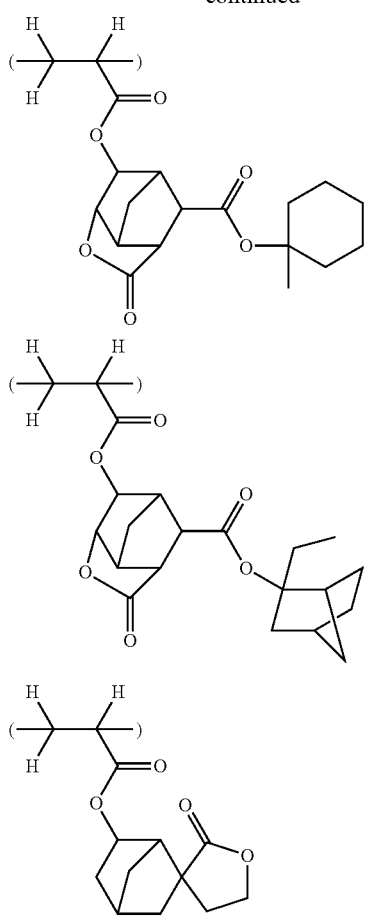
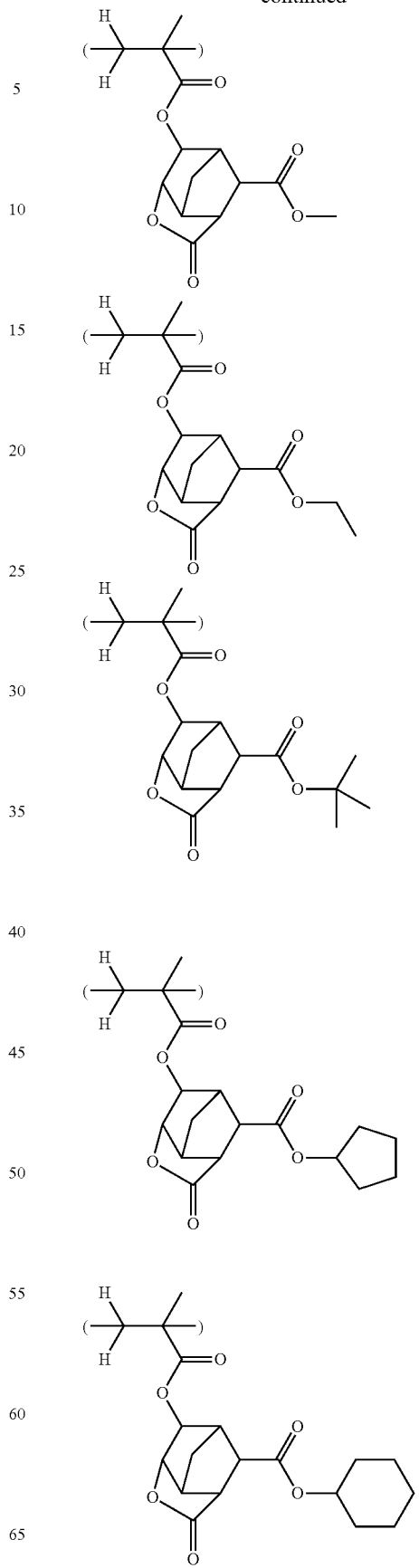

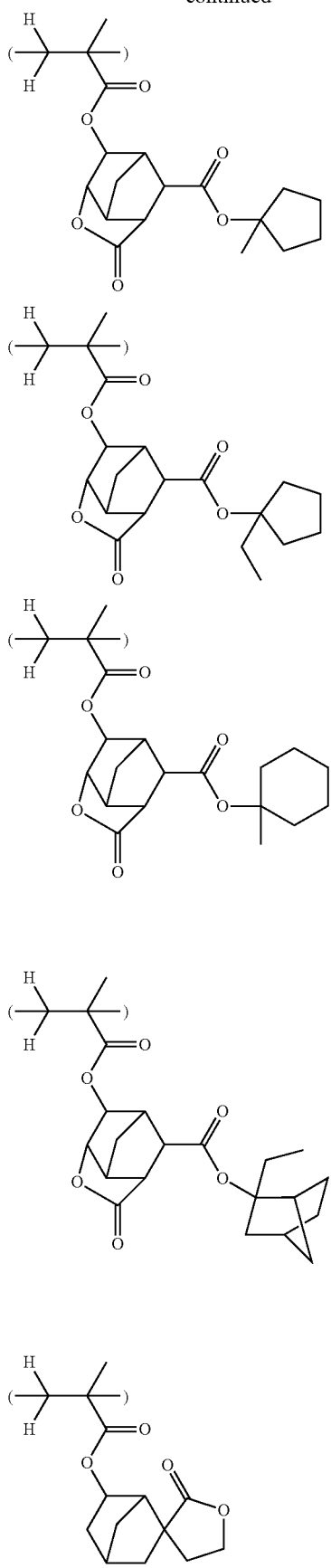
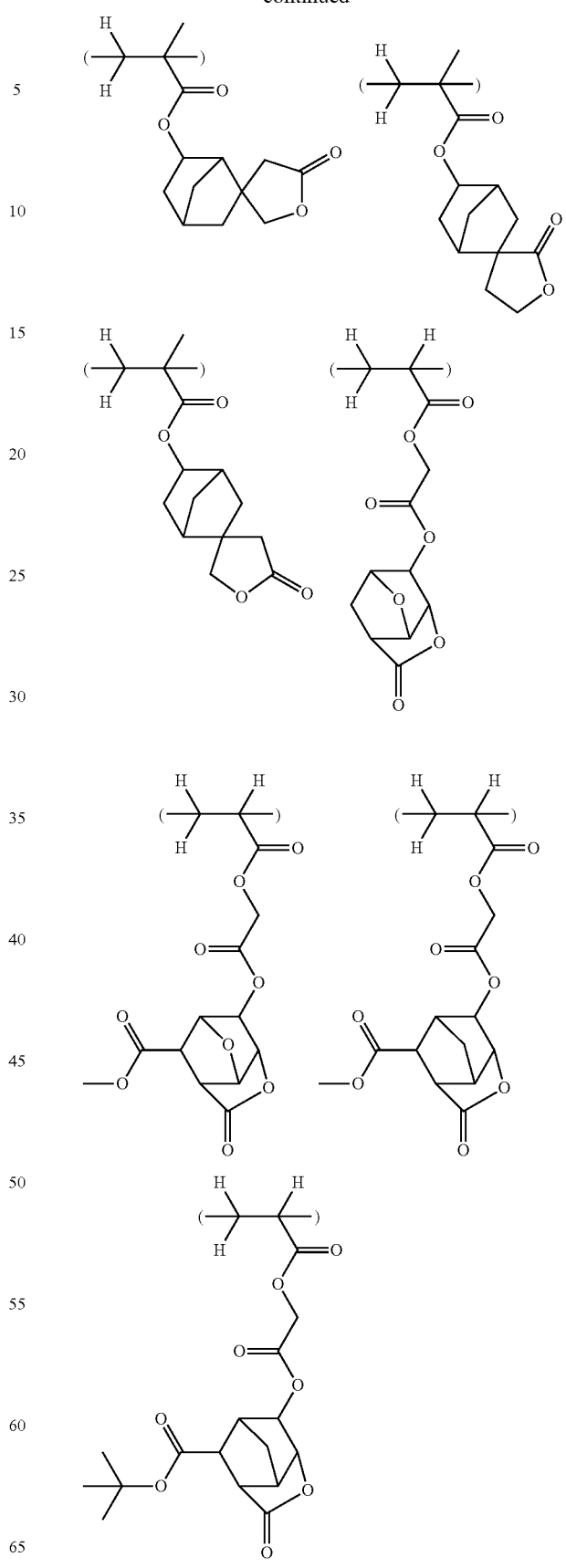

69
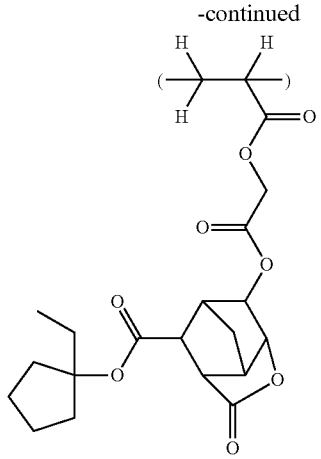
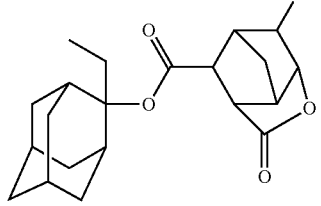
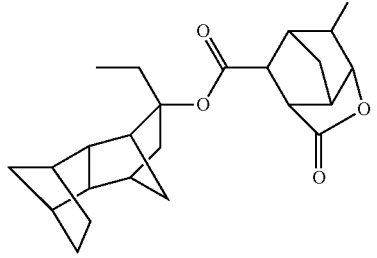
70
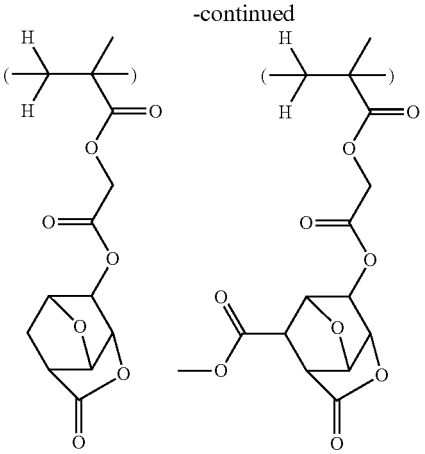
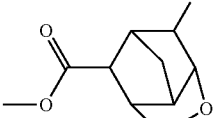
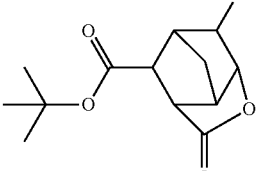
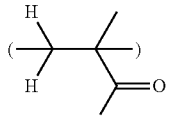
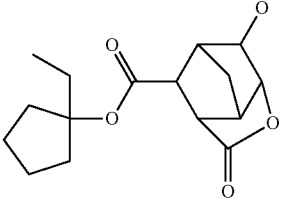

71
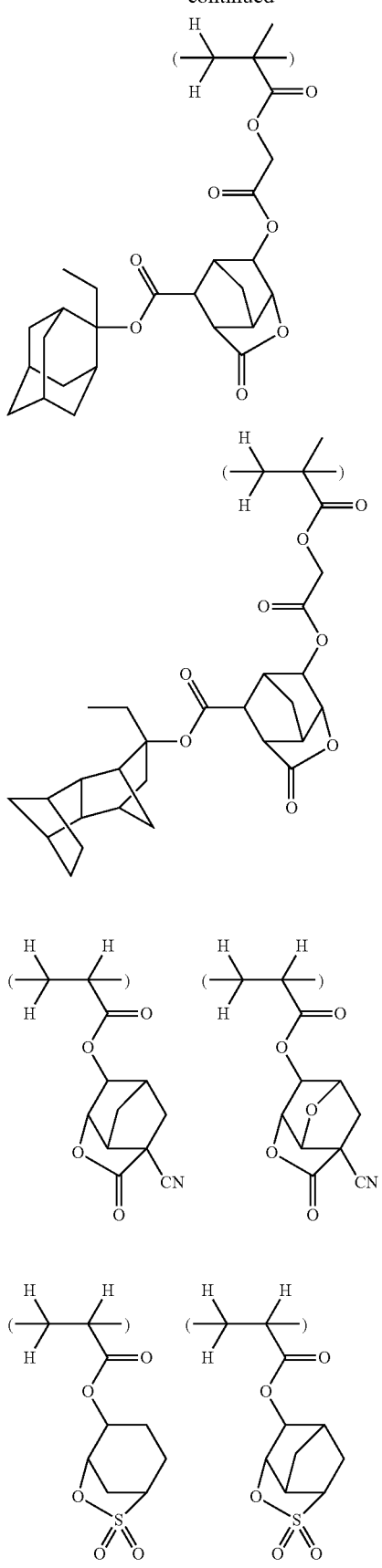
72
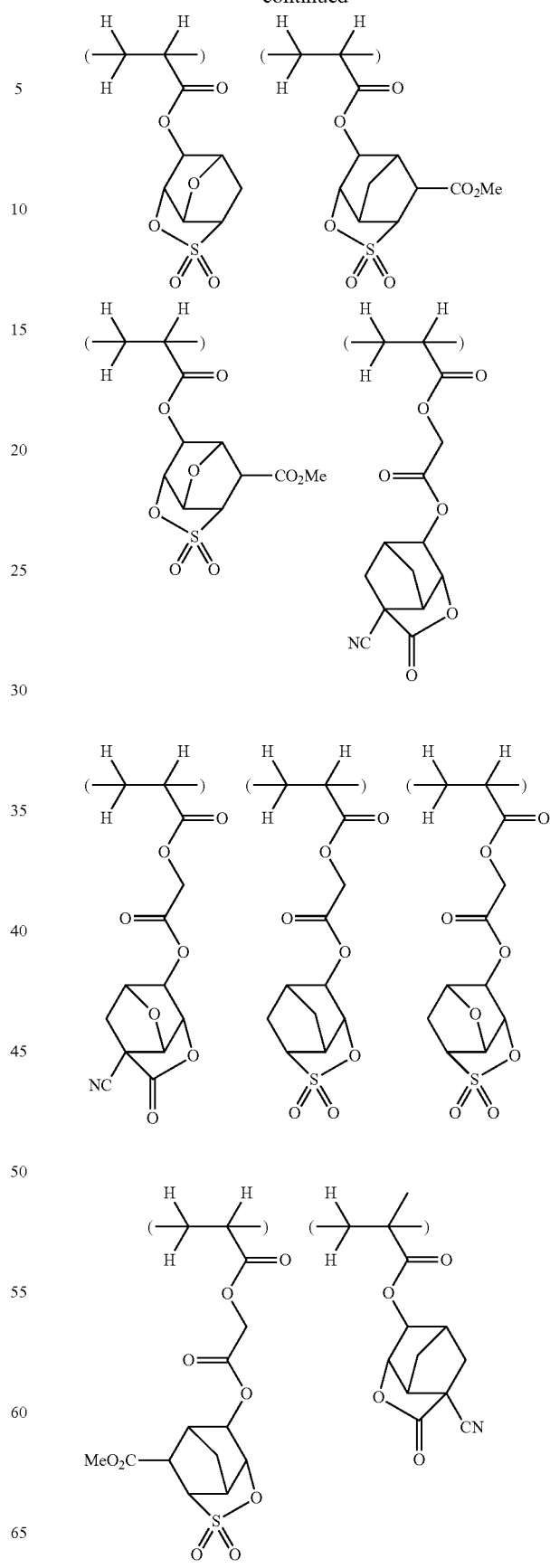

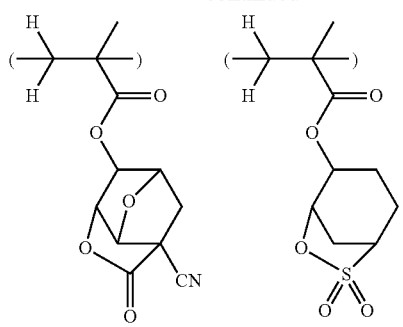
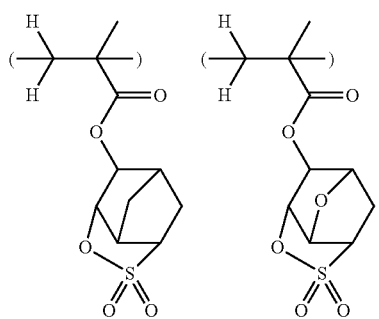
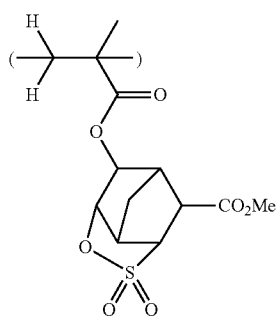
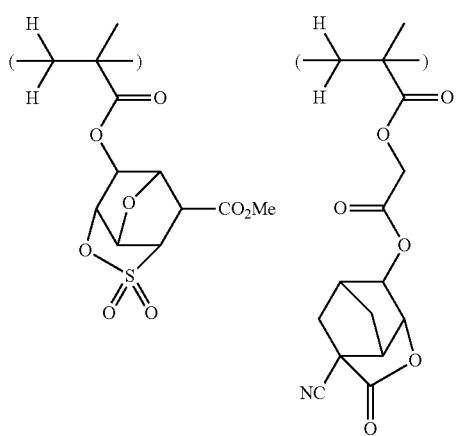
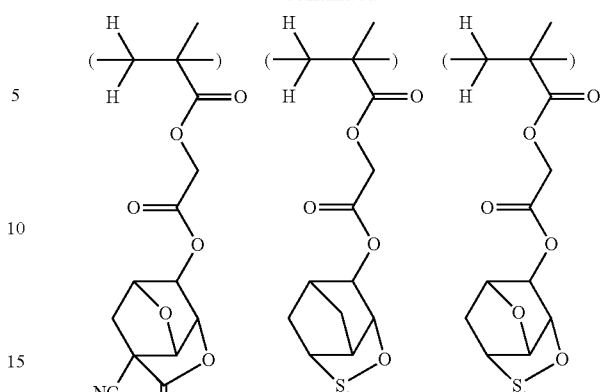
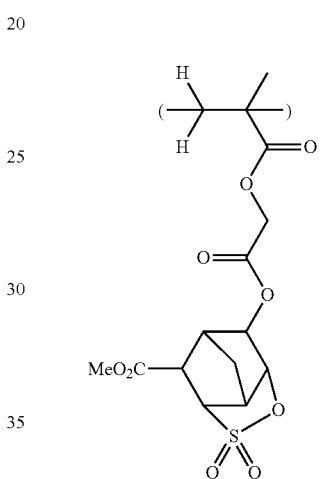
Herein Me stands for methyl.
Illustrative examples of the recurring units having formula (4D) are given below, but not limited thereto.
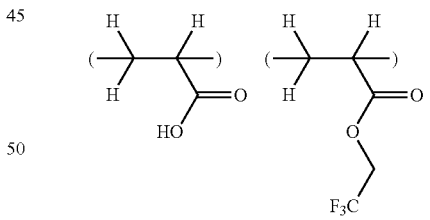
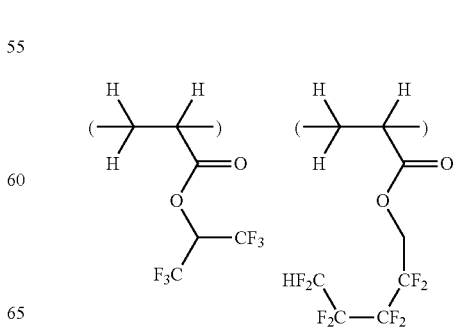

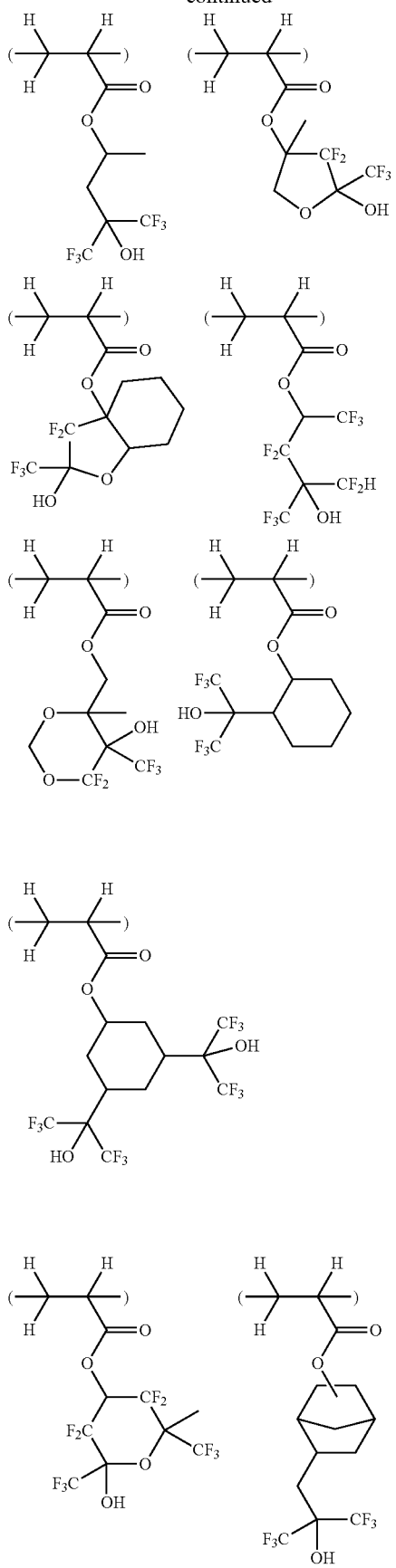
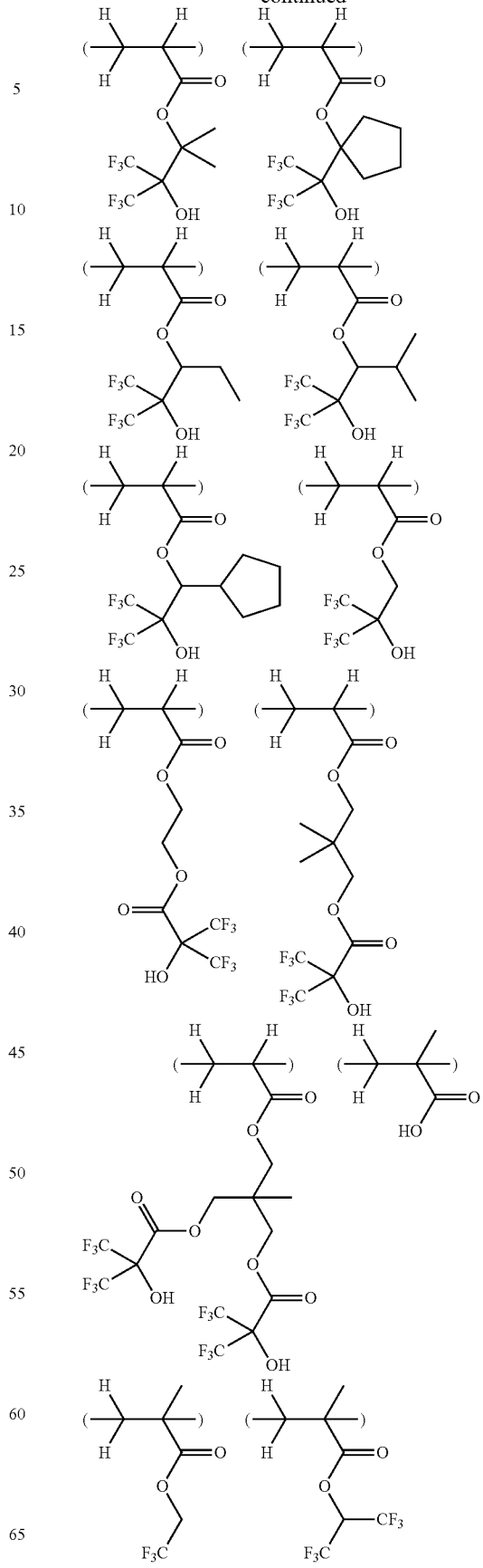

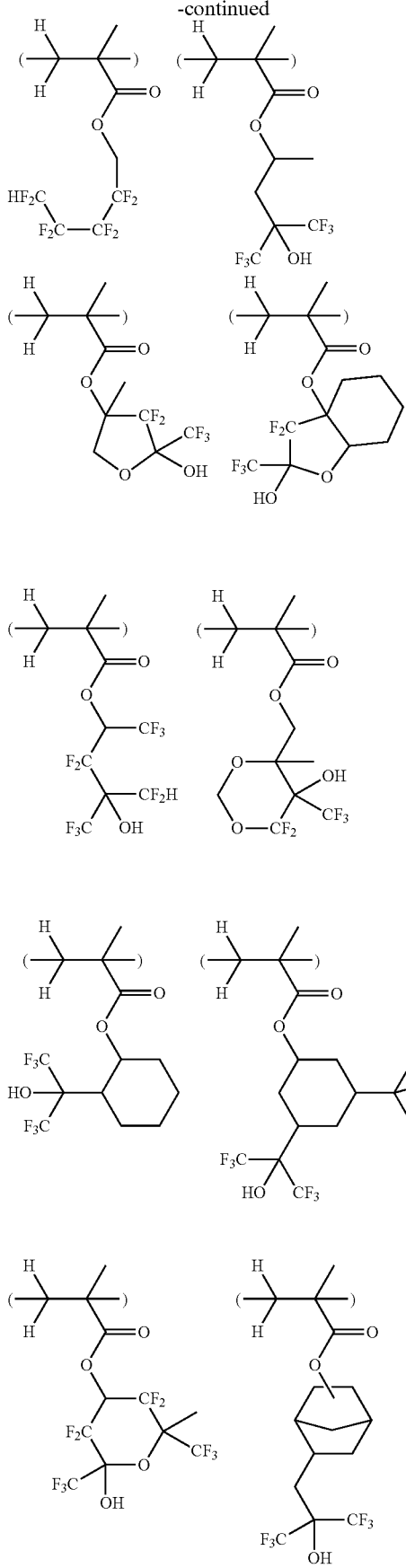

A polymer comprising recurring units of formula (4E) is decomposed under the action of acid to generate a hydroxyl group so that its solubility in various solvents may change. The acid labile group XE may be selected from a variety of such groups. Examples of the acid labile group XE are groups of formulae (L1) to (L4), tertiary alkyl groups of 4 to 20 carbon atoms, trialkylsilyl groups in which each alkyl moiety has 1 to 6 carbon atoms, and oxoalkyl groups of 4 to 20 carbon atoms, like the acid labile group XA mentioned above.
Illustrative examples of the recurring units having formula (4E) are given below, but not limited thereto.
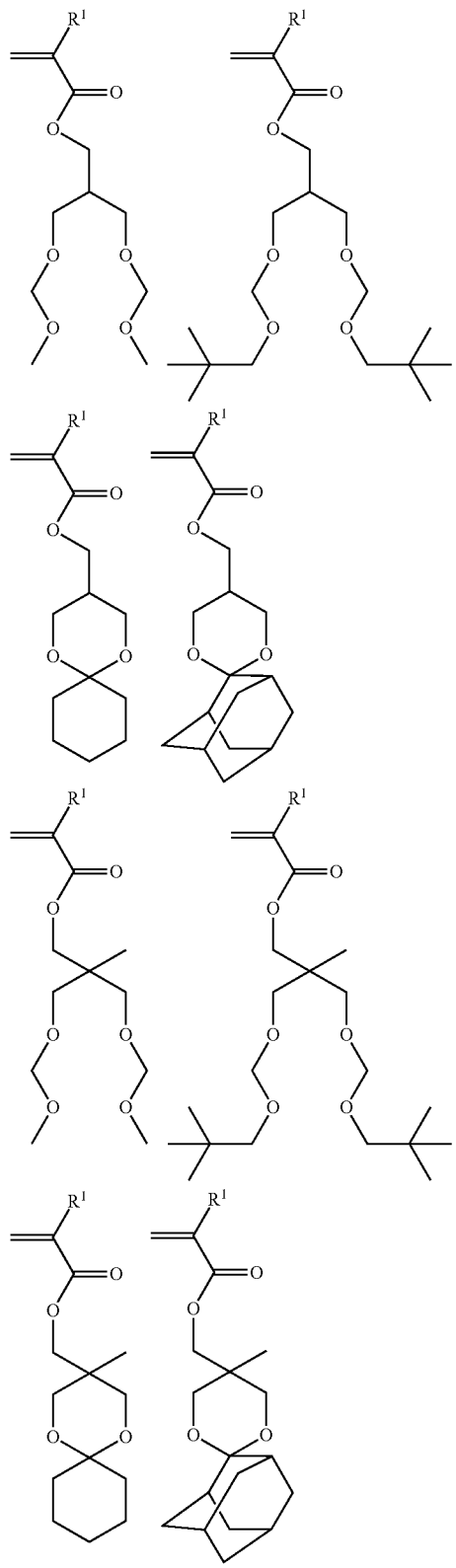
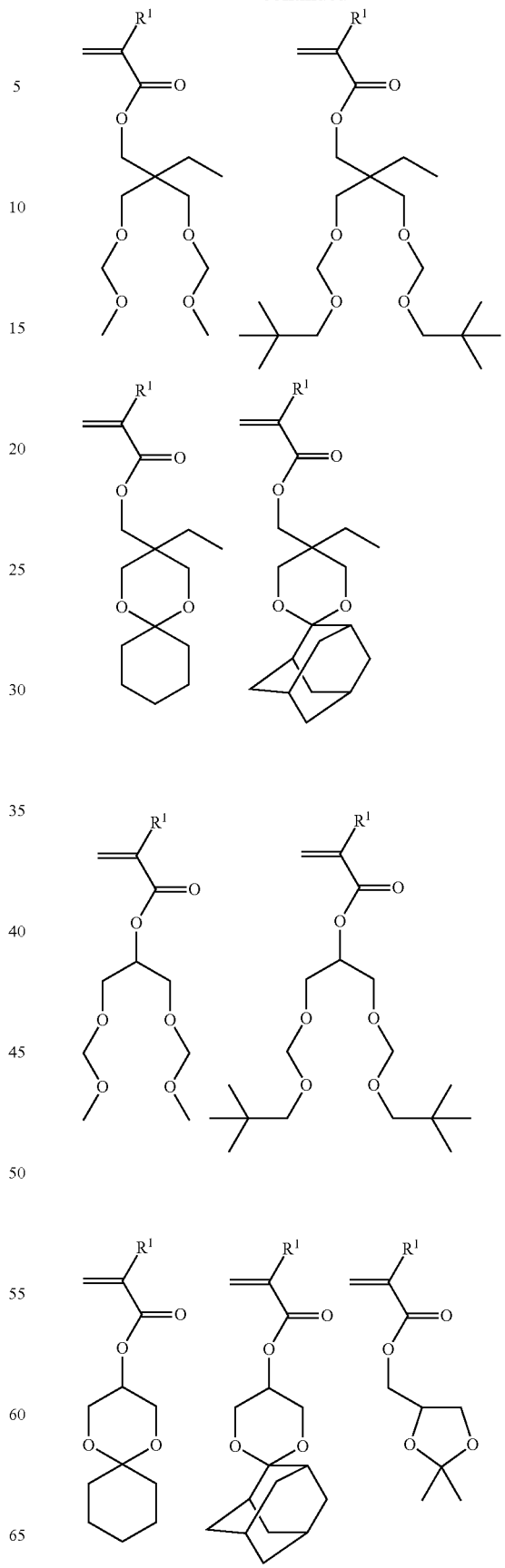

81
-continued
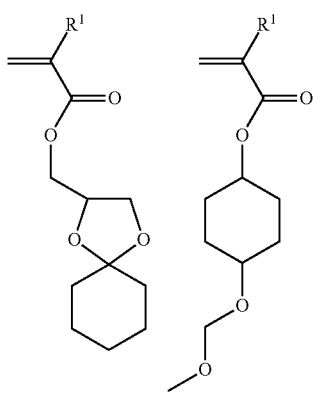
82
-continued
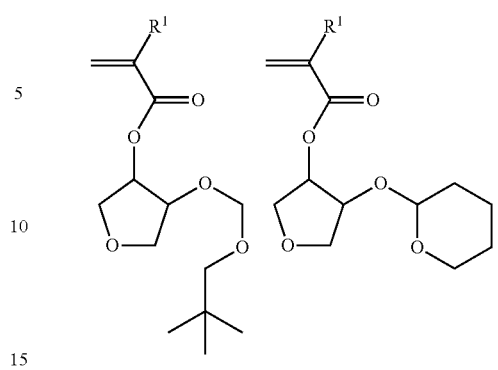
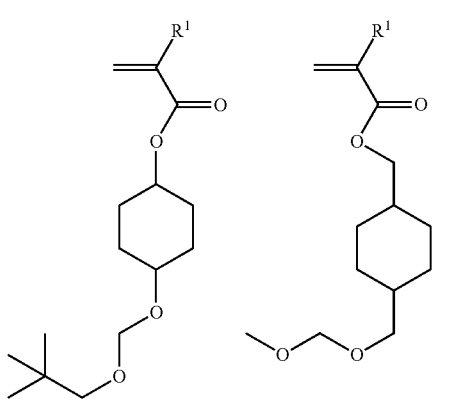
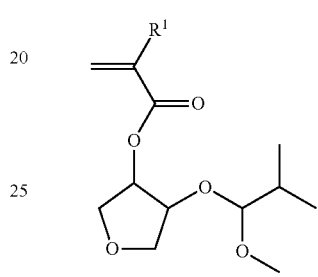
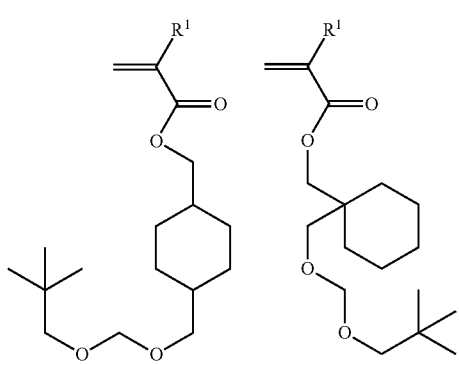
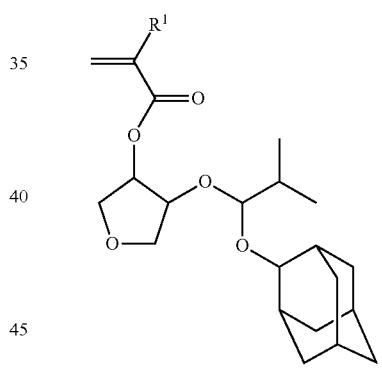
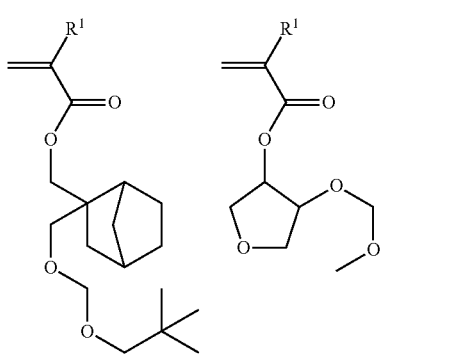
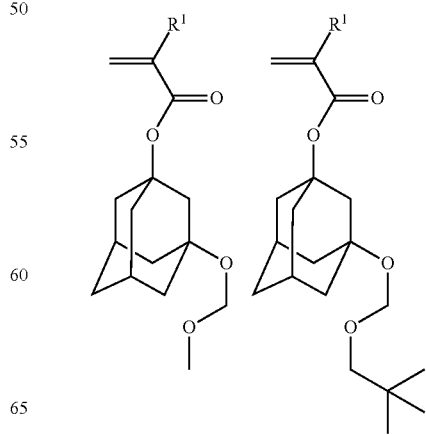

83
-continued
84
-continued
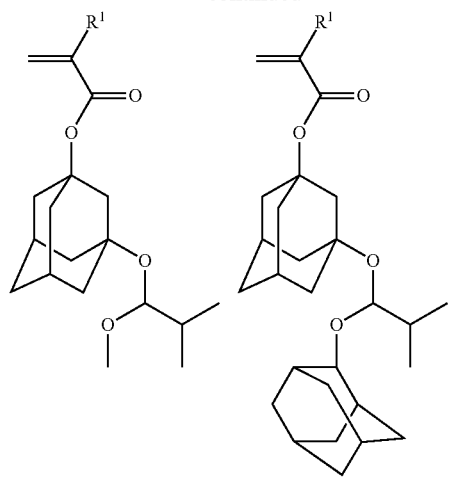
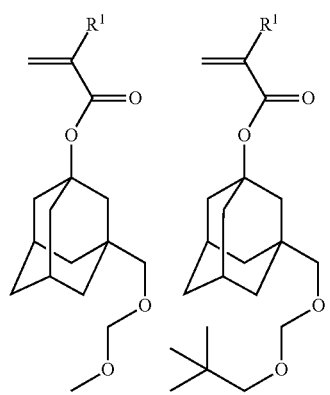
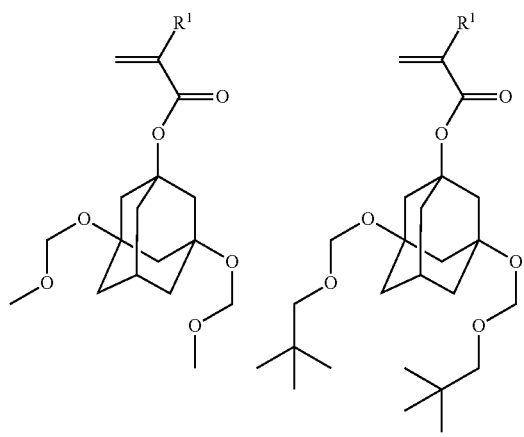
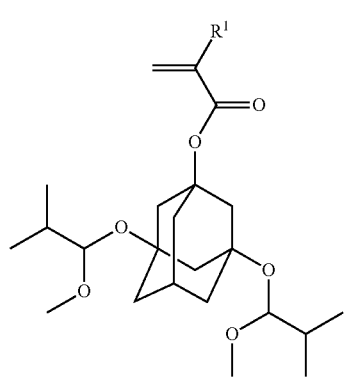
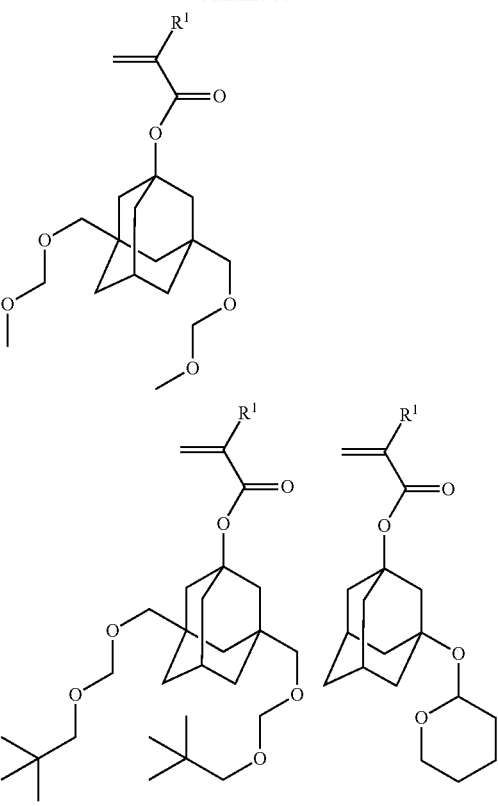
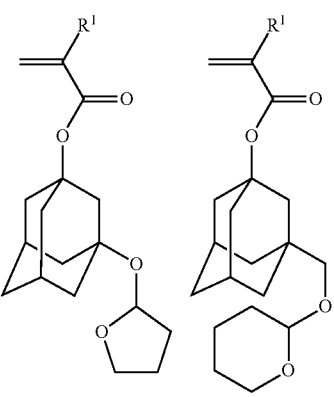
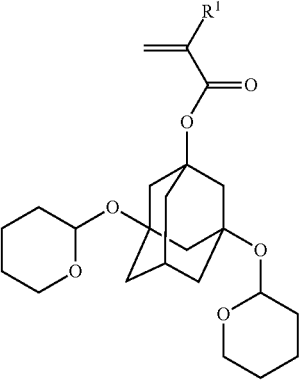

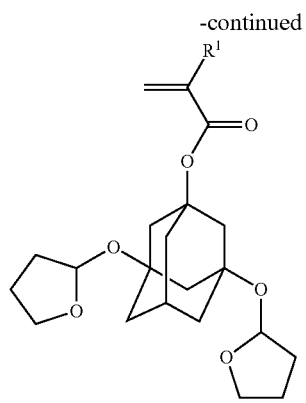
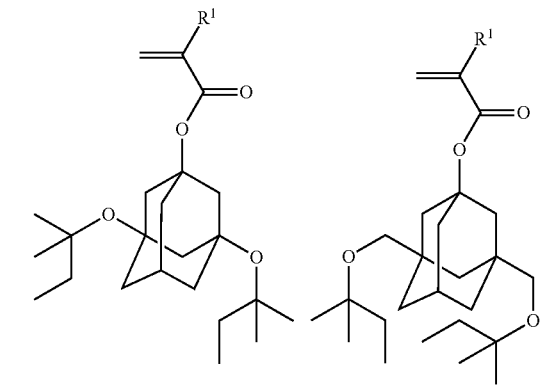
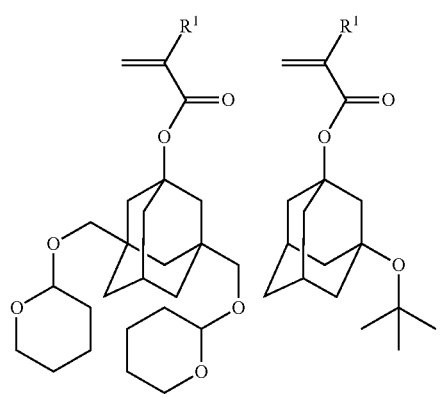
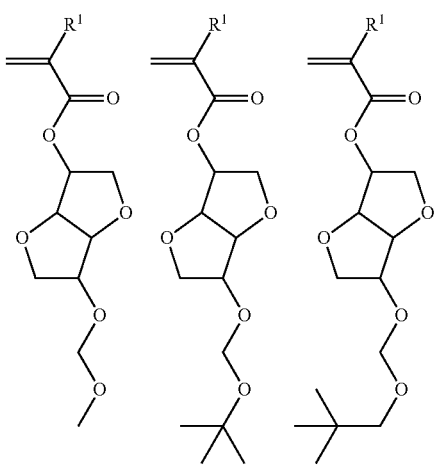
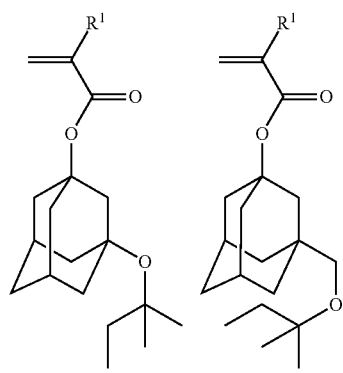
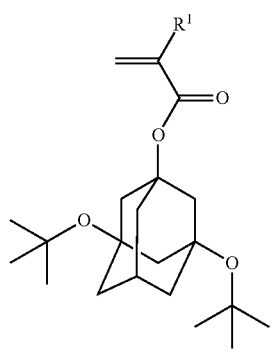
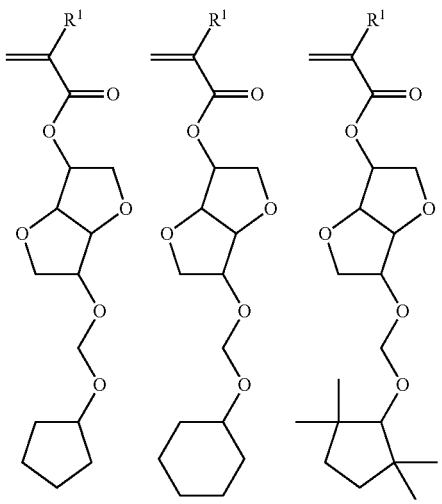

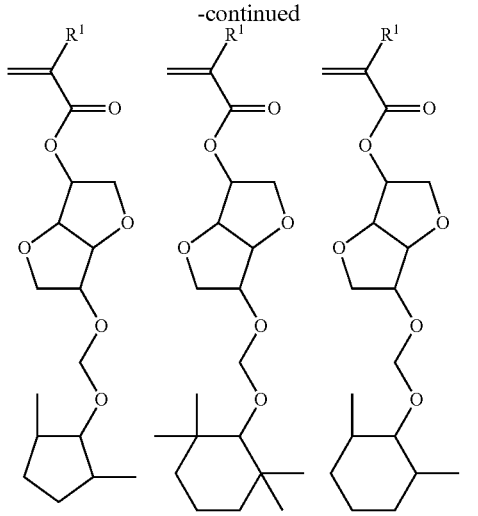
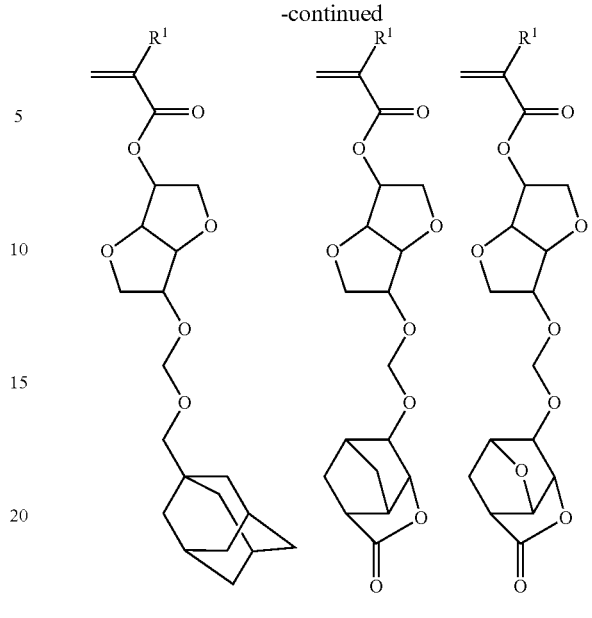
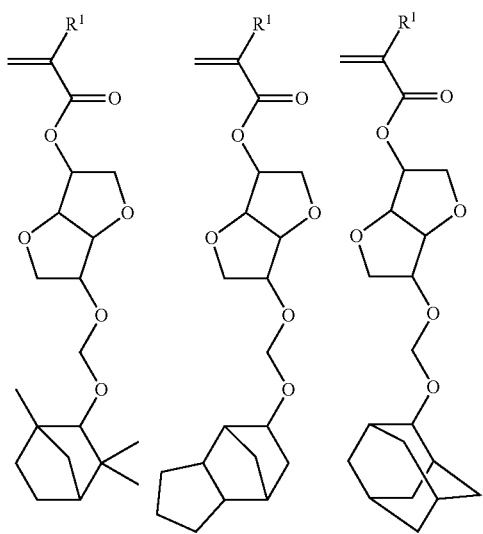
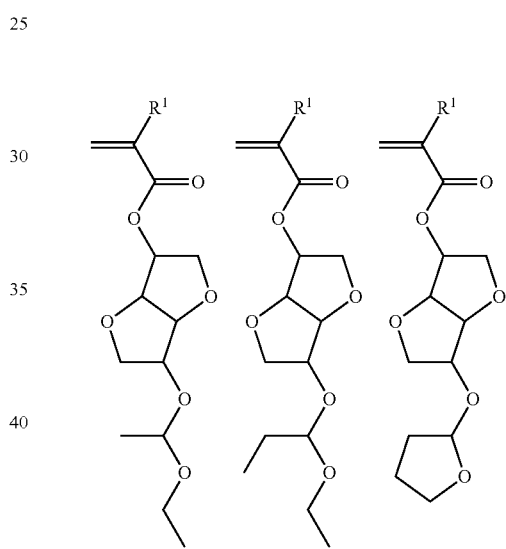
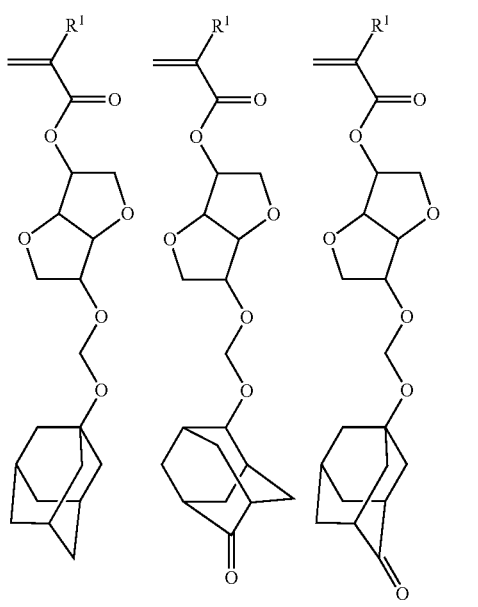
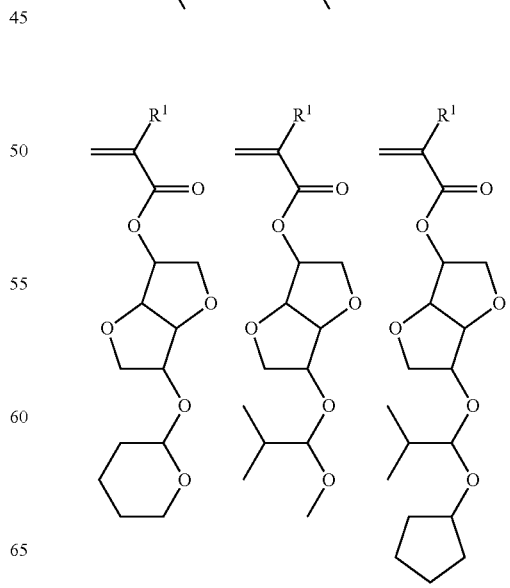

89
-continued
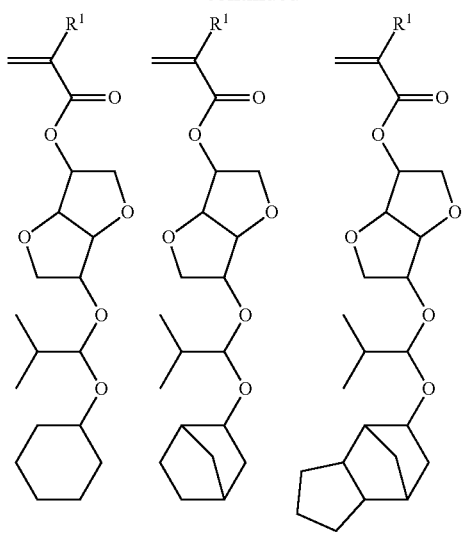
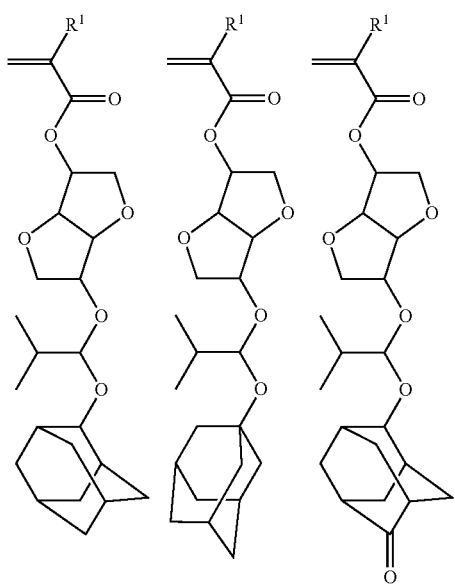
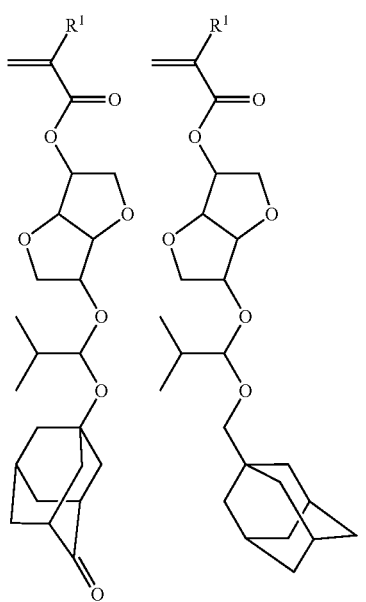
90
-continued
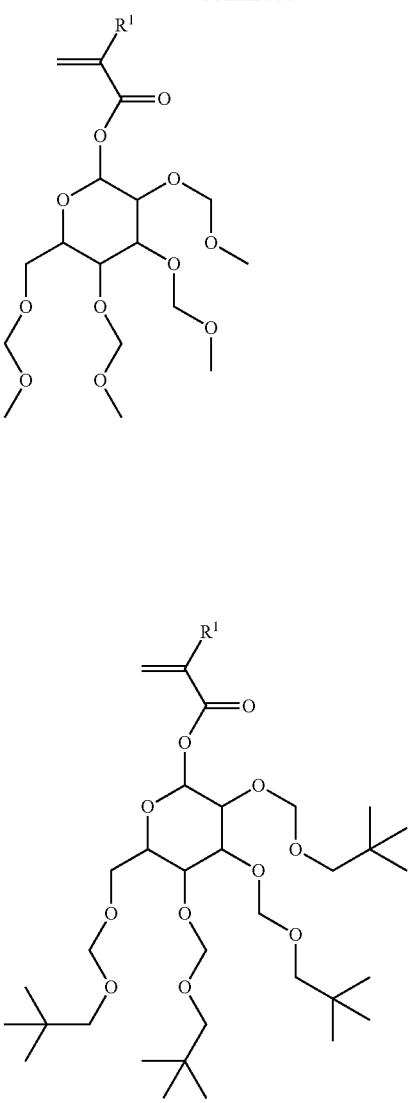
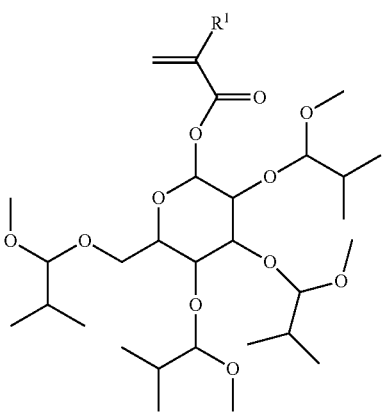

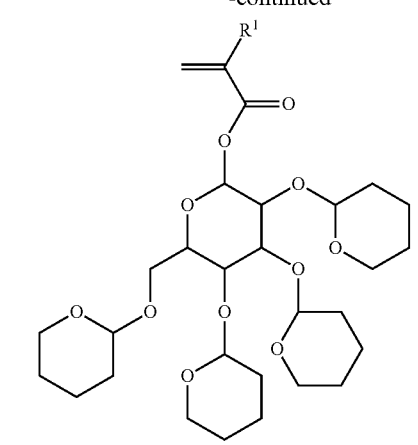
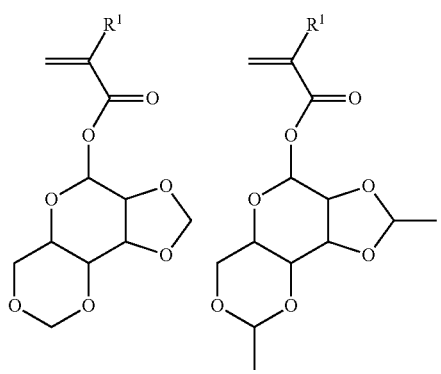
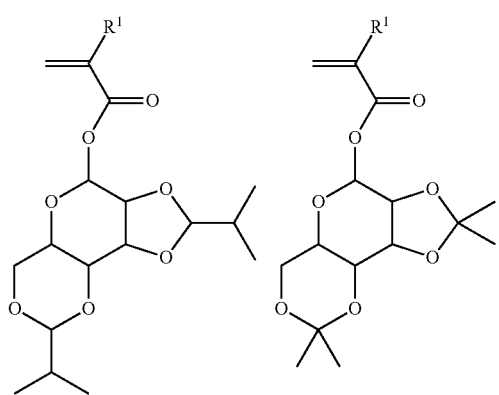
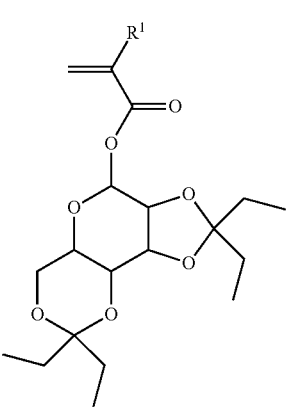
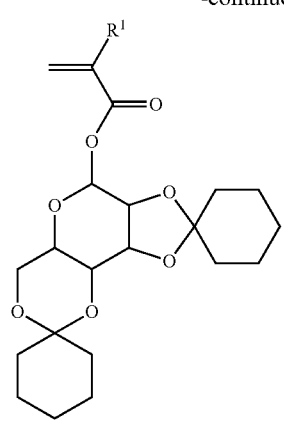
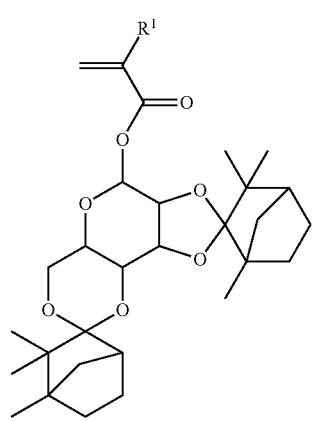
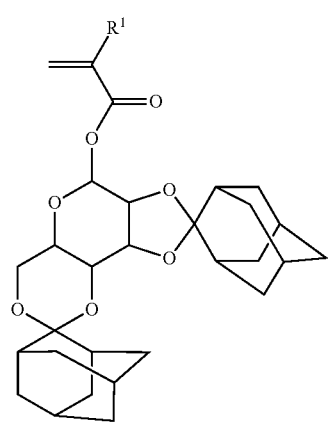
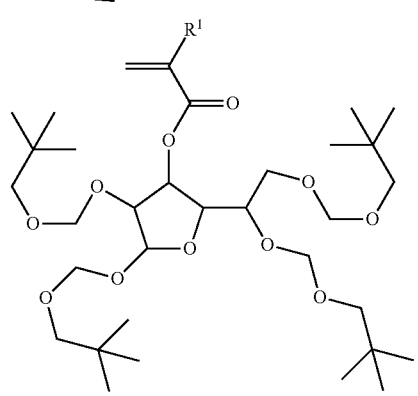

-continued

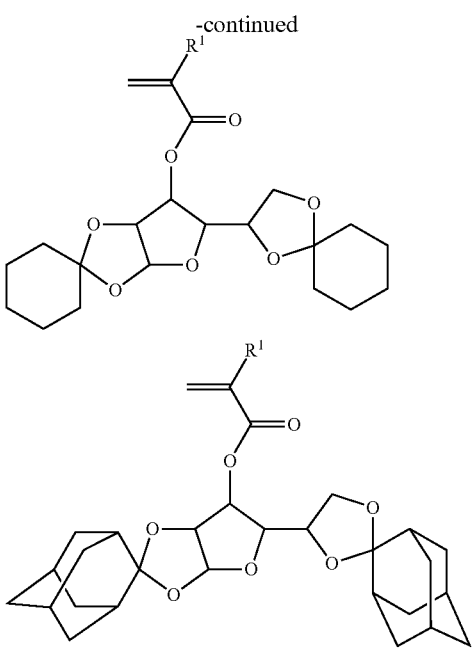

In a preferred embodiment, the polymer may have further copolymerized therein any of recurring units (d1) to (d3) of sulfonium salt represented by the following general formulae.

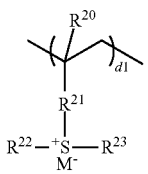 (d1)

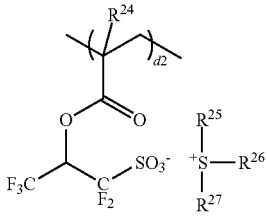 (d2)

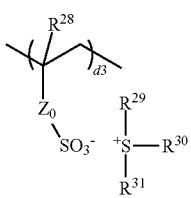 (d3)

Herein $R^{20}$, $R^{24}$ and $R^{28}$ each are hydrogen or methyl. $R^{21}$ is a single bond, phenylene, —O—$R^{33}$—, or —C(=O)—Y—$R^{33}$— wherein Y is oxygen or NH and $R^{33}$ is a straight, branched or cyclic $C_1$-$C_6$ alkylene group, alkenylene group or phenylene group, which may contain a carbonyl (—CO—), ester (—COO—), ether (—O—) or hydroxyl moiety. $R^{22}$, $R^{23}$, $R^{25}$, $R^{26}$, $R^{27}$, $R^{29}$, $R^{30}$, and $R^{31}$ are each independently a straight, branched or cyclic $C_1$-$C_{12}$ alkyl group which may contain a carbonyl, ester or ether moiety, or a $C_6$-$C_{12}$ aryl group, $C_7$-$C_{20}$ aralkyl group, or thiophenyl group. $Z_0$ is a single bond, methylene, ethylene, phenylene, fluorinated phenylene, —O—$R^{32}$—, or —C(=O)—$Z_1$—$R^{32}$— wherein $Z_1$ is oxygen or NH and $R^{32}$ is a straight, branched or cyclic $C_1$-$C_6$ alkylene group, alkenylene group or phenylene group, which may contain a carbonyl, ester, ether or hydroxyl moiety. M⁻ is a non-nucleophilic counter ion.

In addition to the foregoing units, the polymer may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo-[4.4.0.1$^{2,5}$.1$^{7,10}$]dodecene derivatives, unsaturated acid anhydrides such as itaconic anhydride, and other monomers.

The polymer should preferably have a weight average molecular weight (Mw) in the range of 1,000 to 500,000, and more preferably 3,000 to 100,000, as measured versus polystyrene standards by GPC using tetrahydrofuran solvent. Outside the range, there may result an extreme drop of etch resistance, and a drop of resolution due to difficulty to gain a dissolution rate difference before and after exposure.

In the polymer, the recurring units derived from the inventive monomer and other monomers are preferably incorporated in the following molar fractions (mol %):

(I) more than 0 mol % to 100 mol %, preferably 5 to 70 mol %, and more preferably 10 to 50 mol % of constituent units of at least one type selected from units (3a) and (3b) derived from monomers of formulae (1) and (2);

(II) 0 mol % to less than 100 mol %, preferably 30 to 95 mol %, and more preferably 50 to 90 mol % of constituent units of at least one type selected from units (4A) to (4E);

(III) 0 to 30 mol %, preferably 0 to 20 mol %, and more preferably 0 to 10 mol % of constituent units of at least one type selected from units (d1) to (d3);

(IV) 0 to 80 mol %, preferably 0 to 70 mol %, and more preferably 0 to 50 mol % of constituent units derived from one or more other monomers.

It is noted that when constituent units of at least one type selected from units (d1) to (d3) are incorporated, their fraction is more than 0 mol %, and the upper limit fraction of constituent units of at least one type selected from units (4A) to (4E) is less than 100 mol %, preferably less than 95 mol %, and more preferably less than 90 mol %.

The inventive polymer may be prepared by copolymerization reaction using the compound of formula (1) and/or (2) as a first monomer and polymerizable double bond-bearing compounds as second and subsequent monomers. The copolymerization reaction to produce the inventive polymer may be performed in various modes, preferably radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyl lithium and sec-butyl lithium, ketyl, and Grignard reagents, (c) a temperature of about −78° C. to about 0° C., (d) a time of about 0.5 hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 hour to about 48 hours. Reaction conditions outside the described range may be employed if desired.

Resist Composition

The polymer is useful as a base resin in a resist composition, especially chemically amplified positive resist composition. A further embodiment of the invention is a resist composition, especially chemically amplified positive resist composition comprising the polymer. Preferably the resist composition comprises the following components:

(A) the inventive polymer as base resin, (B) an acid generator, (C) an organic solvent, and optionally, (D) a nitrogen-containing organic compound and (E) a surfactant.

It is noted that the acid generator (B) may be omitted when the polymer has copolymerized therein recurring units (d1), (d2) or (d3).

In some embodiments, the base resin may be a blend of the inventive polymer with another polymer capable of increasing its dissolution rate in alkaline developer under the action of acid. Suitable other polymers include, but are not limited to, (i) poly(meth)acrylate derivatives, (ii) norbornene derivative-maleic anhydride copolymers, (iii) hydrogenated products of ring-opening metathesis polymerization (ROMP) polymers, and (iv) vinyl ether-maleic anhydride-(meth)acrylate derivative copolymers.

With respect to the synthesis of hydrogenated ROMP polymers, reference should be made to Examples in JP-A 2003-066612. Examples of the hydrogenated ROMP polymers are shown below, but not limited thereto.

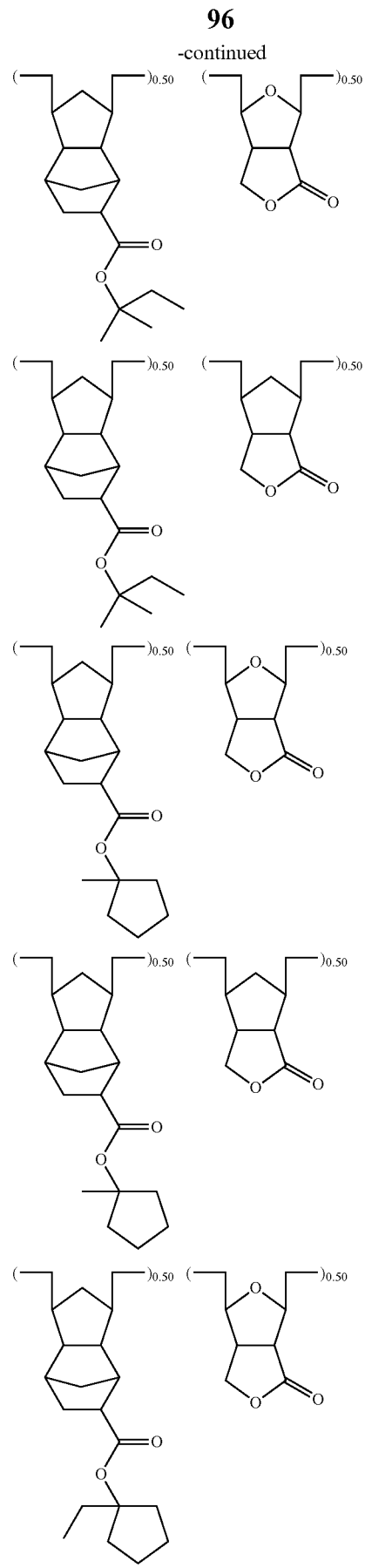

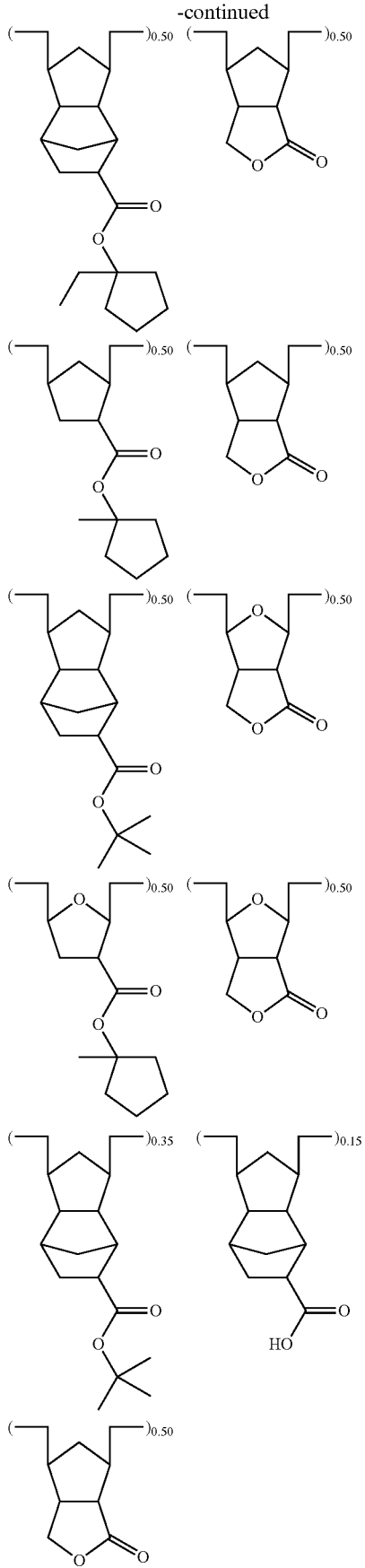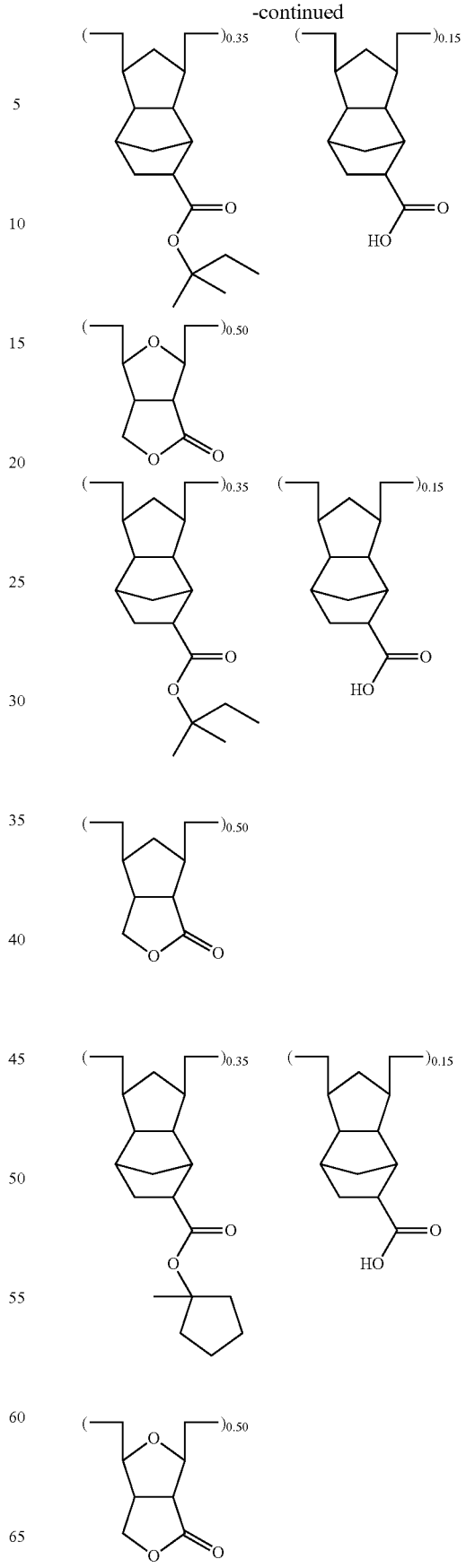

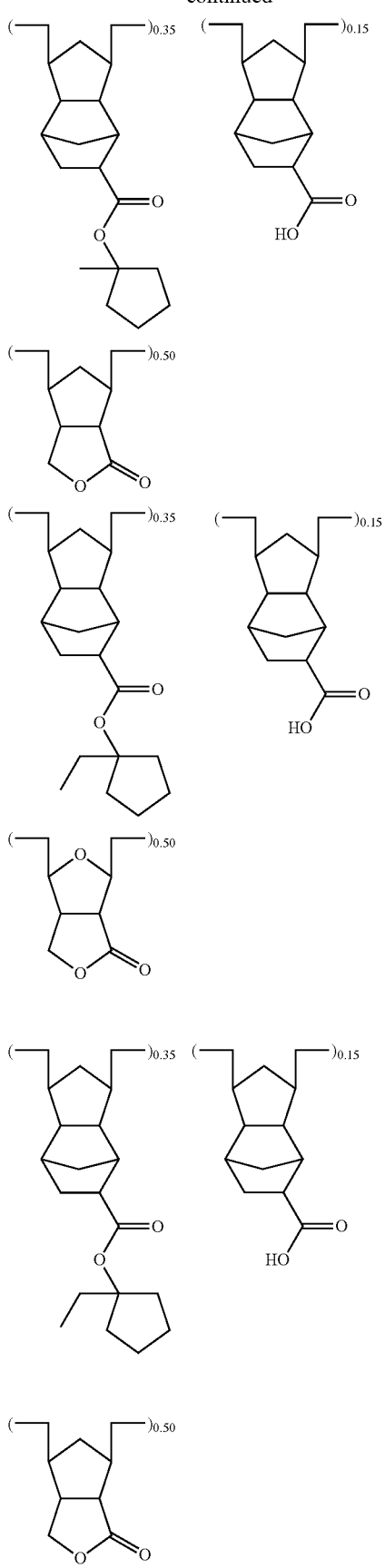
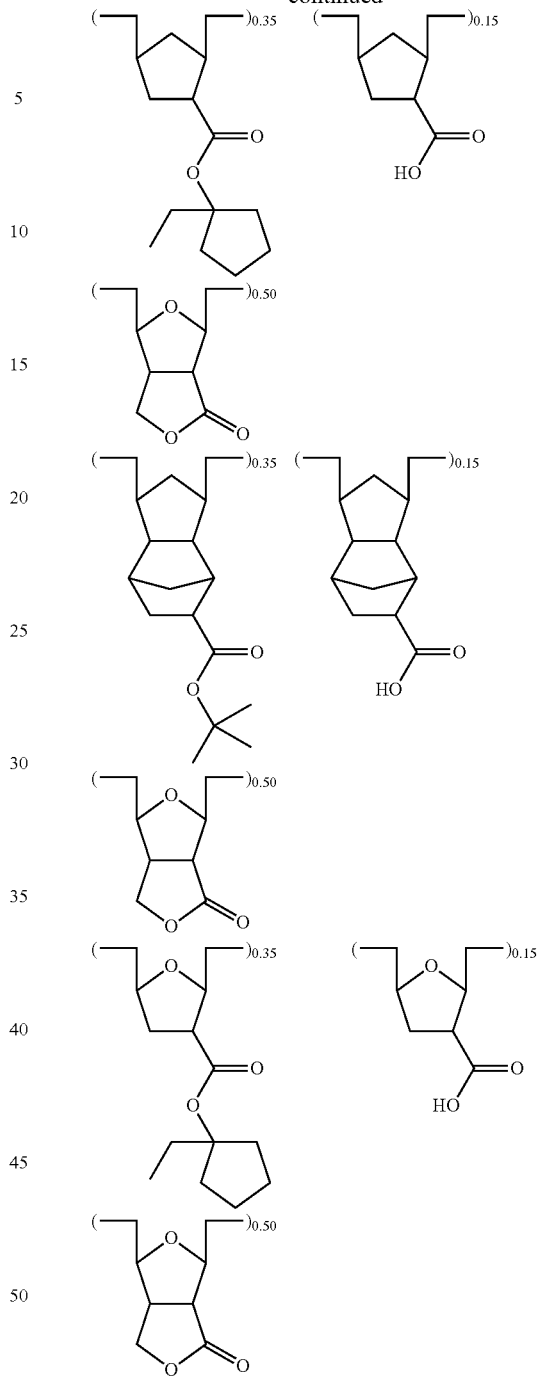

On use of the polymer blend, the inventive polymer and the other polymer are preferably blended in a weight ratio between 100:0 and 10:90, more preferably between 100:0 and 20:80. If the ratio of the inventive polymer is less than the range, the resist composition may fail to exert the desired characteristics. The characteristics of the resist composition may be adjusted by changing the blending ratio.

It is also acceptable to use a blend of two or more inventive polymers. The characteristics of the resist composition may be adjusted by using a plurality of inventive polymers.

Typical of the acid generator used herein is a photoacid generator (PAG). The PAG is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. Examples of these PAGs are described in JP-A 2009-269953, paragraphs [0151] to [156] (U.S. Pat. No. 8,114,571).

It is noted that an acid diffusion controlling function may be provided when two or more PAGs are used in admixture provided that one PAG is an onium salt capable of generating a weak acid. Specifically, in a system using a mixture of a PAG capable of generating a strong acid (e.g., fluorinated sulfonic acid) and an onium salt capable of generating a weak acid (e.g., non-fluorinated sulfonic acid or carboxylic acid), if the strong acid generated by the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If the PAG capable of generating a strong acid is also an onium salt, an exchange from the strong acid (generated upon exposure to high-energy radiation) to a weak acid as above can take place, but it never happens that the weak acid (generated upon exposure to high-energy radiation) collides with the unreacted onium salt capable of generating a strong acid to induce a salt exchange. This is because of a likelihood of an onium cation forming an ion pair with a stronger acid anion.

An appropriate amount of PAG added is 0.1 to 40 parts, and more preferably 0.1 to 20 parts by weight per 100 parts by weight of the base resin (A) in the resist composition. As long as PAG is up to 40 phr, the resulting resist film has a fully high transmittance and a minimal likelihood of degraded resolution. The PAG may be used alone or in admixture of two or more. The transmittance of the resist film can be controlled by using a PAG having a low transmittance at the exposure wavelength and adjusting the amount of the PAG added.

To the resist composition, a compound which is decomposed with an acid to generate another acid, that is, acid amplifier compound may be added. For these compounds, reference should be made to J. Photopolym. Sci. and Tech., 8, 43-44, 45-46 (1995), and ibid., 9, 29-30 (1996). Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known PAGs, many of those compounds having poor stability, especially poor thermal stability exhibit an acid amplifier-like behavior. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Component (C) used herein may be any organic solvent as long as the base resin, acid generator and other components are dissolvable therein. Exemplary organic solvents include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture. Of these, diethylene glycol dimethyl ether, 1-ethoxy-2-propanol, PGMEA and mixtures thereof are preferred because the acid generator is most soluble therein.

An appropriate amount of the organic solvent used is 200 to 1,000 parts, and especially 400 to 800 parts by weight per 100 parts by weight of the base resin.

As component (D), nitrogen-containing organic compounds may be used alone or in admixture. Those compounds capable of suppressing the rate of diffusion when the acid generated by the PAG diffuses within the resist film are useful. The inclusion of such quencher facilitates adjustment of resist sensitivity and holds down the rate of acid diffusion within the resist film, resulting in better resolution. In addition, it suppresses changes in sensitivity following exposure and mitigates substrate poisoning and environment dependence, as well as improving the exposure latitude and the pattern profile.

Suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide, imide and carbamate derivatives. Illustrative examples are described in JP-A 2009-269953, paragraphs [0122] to [0141].

The basic compound is preferably used in an amount of 0.001 to 8 parts, more preferably 0.01 to 4 parts by weight per 100 parts by weight of the base resin. Less than 0.001 phr fails to achieve the desired addition effect whereas more than 8 phr may lead to a lowering of sensitivity. The preferred nitrogen-containing organic compound is a compound capable of holding down the diffusion rate of acid when the acid generated by the acid generator diffuses in the resist film. The inclusion of the nitrogen-containing organic compound holds down the diffusion rate of acid in the resist film, which leads to many advantages including improved resolution, minimized sensitivity change following exposure, reduced substrate poisoning and environment dependency, and improved exposure latitude and pattern profile.

As component (E), nonionic surfactants are preferred. Suitable surfactants include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from DIC Corp., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

Optionally, a polymer may be added to the resist composition of the invention which will segregate at the top of a coating and functions to adjust a hydrophilic/hydrophobic balance at the surface, to enhance water repellency, or to prevent low-molecular-weight components from flowing into or out of the coating when the coating comes in contact with water or similar liquids. The amount of functional polymer added is as used in resist compositions of this type as long as it does not compromise the objects of the invention, and is preferably up to 15 parts, and more preferably up to 10 parts by weight per 100 parts by weight of the base resin.

Preferred examples of the functional polymer which will segregate at the coating top include polymers and copolymers comprising fluorinated units of one or more types, and copolymers comprising fluorinated units and other units. Illustrative examples of suitable fluorinated units and other units are shown below, but not limited thereto.

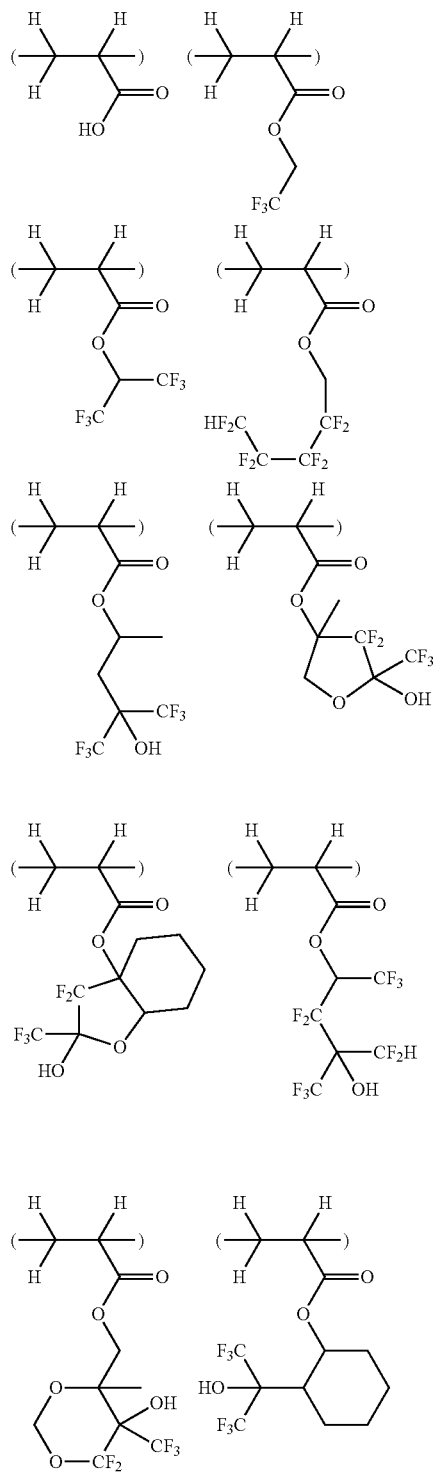

-continued

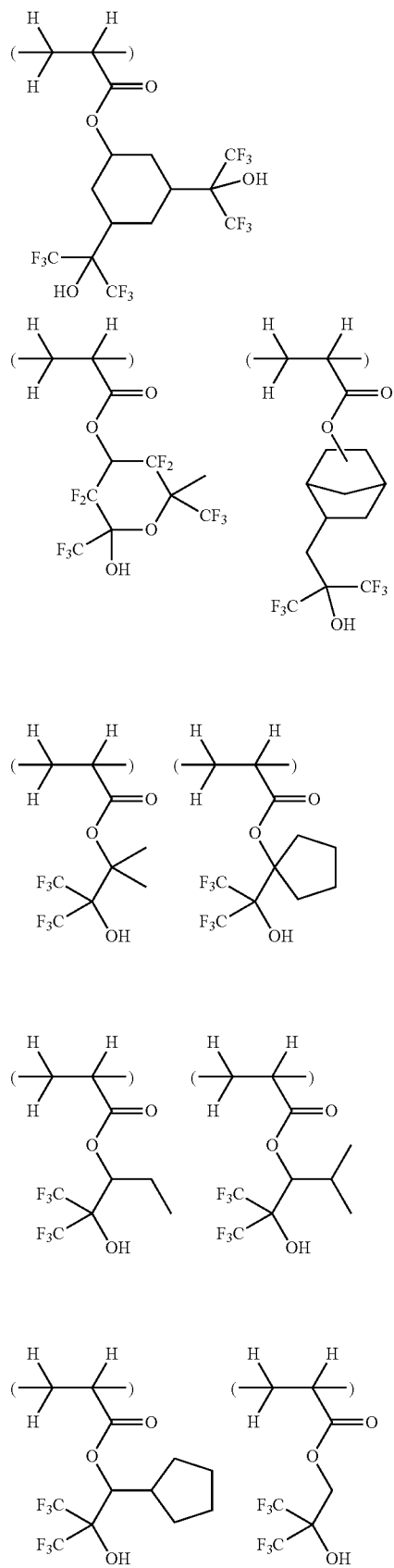

105
-continued
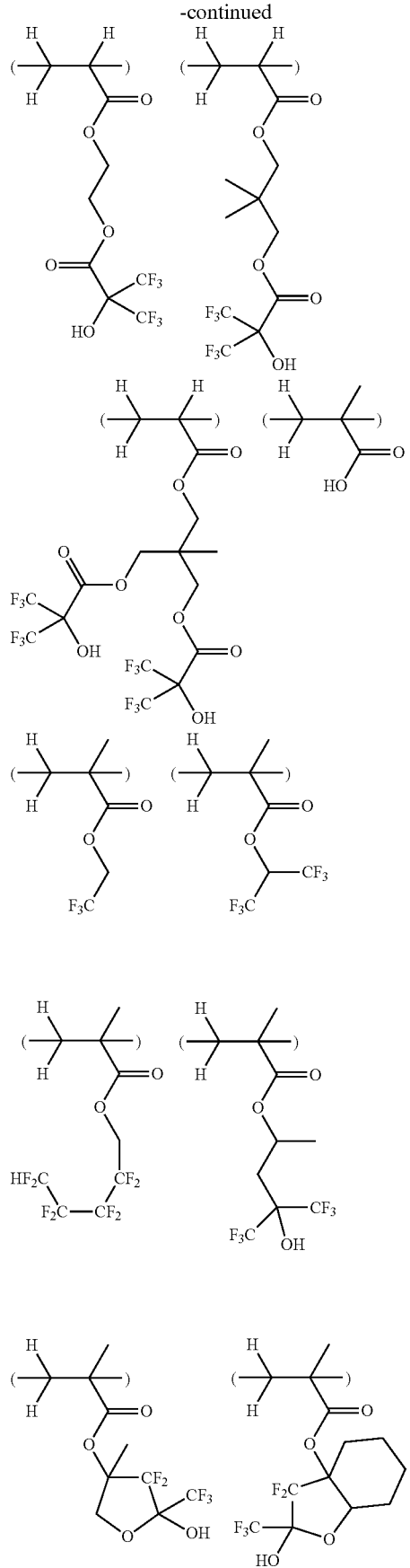
106
-continued
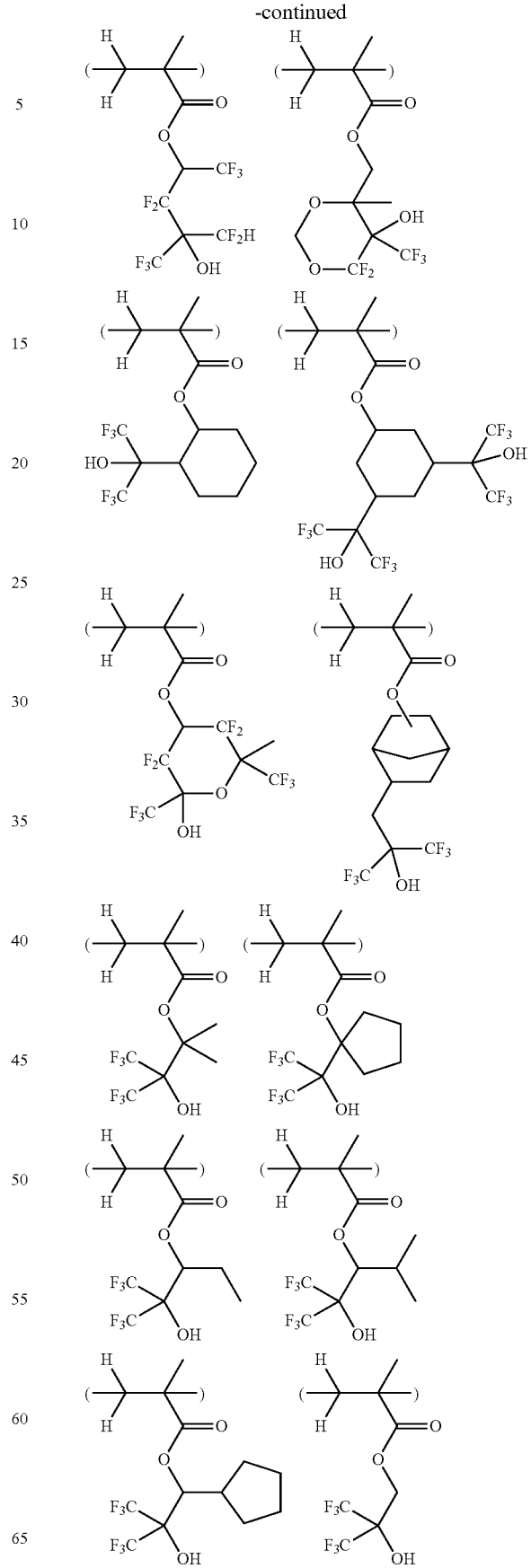

-continued

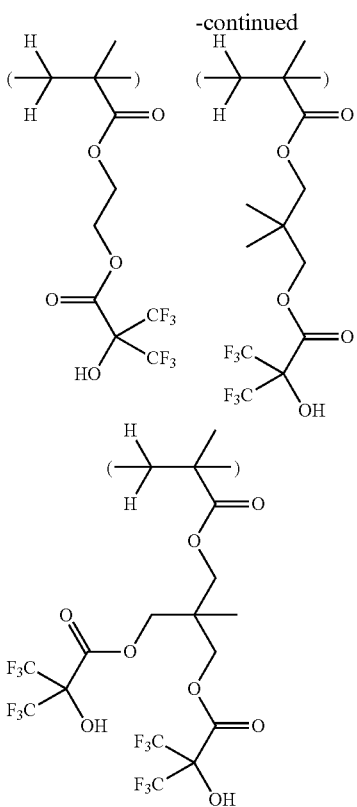

The functional polymer which will segregate at the coating top should preferably have a Mw of 1,000 to 50,000, more preferably 2,000 to 20,000, as measured by GPC versus polystyrene standards. Outside the range, the polymer may have insufficient surface-modifying effect or cause development defects.

While the resist composition of the invention typically comprises a polymer, acid generator, organic solvent and organic nitrogen-containing compound as described above, there may be added optional other ingredients such as dissolution inhibitors, acidic compounds, stabilizers, and dyes. Optional ingredients may be added in conventional amounts so long as this does not compromise the objects of the invention.

Process

Pattern formation using the resist composition of the invention may be performed by well-known lithography processes. The process generally involves coating, heat treatment (or prebake), exposure, heat treatment (PEB), and development. If necessary, any additional steps may be added.

The process of forming a positive pattern using an aqueous alkaline solution as developer is well known in the art, for example, from JP-A 2011-231312, paragraphs [0138] to [0146].

The process of forming a negative pattern using an organic solvent as developer is illustrated in FIG. 1. First, the resist composition is coated on a substrate to form a resist film thereon. Specifically, a resist film 40 of a resist composition is formed on a processable substrate 20 disposed on a substrate 10 directly or via an intermediate intervening layer 30 as shown in FIG. 1A. The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 300 seconds, especially 15 to 200 seconds.

The substrate 10 used herein is generally a silicon substrate. The processable substrate (or target film) 20 used herein includes $SiO_2$, SiN, SiON, SiOC, p-Si, α-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Figure 1B:
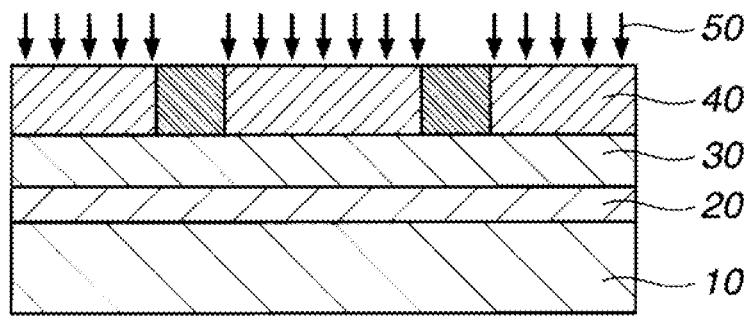
FIGS. 1 (A)-1 (C) schematically illustrate in cross-sectional views the pattern forming process of the invention.
FIG. 1C shows the photoresist film being developed in organic solvent.

Next comes exposure depicted at 50 in FIG. 1B. For the exposure, preference is given to high-energy radiation having a wavelength of 140 to 250 nm, EUV having a wavelength of 13.5 nm, EB, and especially ArF excimer laser radiation of 193 nm. The exposure may be done either in a dry atmosphere such as air or nitrogen stream or by immersion lithography in water. The ArF immersion lithography uses deionized water or liquids having a refractive index of at least 1 and highly transparent to the exposure wavelength such as alkanes as the immersion solvent. The immersion lithography involves prebaking a resist film and exposing the resist film to light through a projection lens, with water introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing (or post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer having 1,1,1,3,3,3-hexafluoro-2-propanol residues which is insoluble in water, but soluble in an alkaline developer liquid, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue. While the protective film must dissolve in the organic solvent developer, the polymer comprising recurring units derived from a monomer having a 1,1,1,3,3,3-hexafluoro-2-propanol residue dissolves in organic solvent developers. In particular, protective film-forming materials having 1,1,1,3,3,3-hexafluoro-2-propanol residues as described in JP-A 2007-025634, 2008-003569, 2008-81716, and 2008-111089 readily dissolve in organic solvent developers.

In the protective film-forming composition, an amine compound or amine salt or a polymer having copolymerized therein recurring units containing an amine group or amine salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful protective film materials having an amino group or amine salt copolymerized are described in JP-A 2007-316448. The amine compound or amine salt may be selected from the compounds enumerated as the basic compound to be added to the resist composition. An appropriate amount of the amine compound or amine salt added is 0.01 to 10 parts, preferably 0.02 to 8 parts by weight per 100 parts by weight of the base resin.

After formation of the photoresist film, deionized water rinsing (or post-soaking) may be carried out for extracting the acid generator and the like from the film surface or washing away particles, or after exposure, rinsing (or post-soaking)

may be carried out for removing water droplets left on the resist film. If the acid evaporating from the exposed region during PEB deposits on the unexposed region to deprotect the protective group on the surface of the unexposed region, there is a possibility that the surface edges of holes after development are bridged to close the holes. Particularly in the case of negative development, regions surrounding the holes receive light so that acid is generated therein. There is a possibility that the holes are not opened if the acid outside the holes evaporates and deposits inside the holes during PEB. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfo group is undesirable because of a potential hole opening failure.

A further embodiment of the invention is a process for forming a pattern by applying a resist composition comprising a polymer comprising recurring units having formula (3a) or (3b), an acid generator, and an organic solvent onto a substrate, baking the composition to form a resist film, forming a protective film on the resist film, exposing the resist film to high-energy radiation to define exposed and unexposed regions, baking, and applying a developer to the coated substrate to form a negative pattern wherein the unexposed region of resist film and the protective film are dissolved and the exposed region of resist film is not dissolved. The protective film is preferably formed from a composition comprising a polymer bearing a 1,1,1,3,3,3-hexafluoro-2-propanol residue and an amino group or amine salt-containing compound, or a composition comprising a polymer bearing a 1,1,1,3,3,3-hexafluoro-2-propanol residue and having amino group or amine salt-containing recurring units copolymerized, the composition further comprising an alcohol solvent of at least 4 carbon atoms, an ether solvent of 8 to 12 carbon atoms, or a mixture thereof.

With respect to the recurring units having a 1,1,1,3,3,3-hexafluoro-2-propanol residue, those monomers having a —C(CF$_3$)(OH) group, i.e., a carbon atom having CF$_3$ and OH radicals bonded thereto are preferably selected among the exemplary monomers listed for the recurring unit (4D) (some monomers on pages 48 and 49). The amino group-containing compound may be selected from the exemplary amine compounds (to be added to photoresist compositions) described in JP-A 2008-111103, paragraphs [0146] to [0164]. As the amine salt-containing compound, salts of the foregoing amine compounds with carboxylic acid or sulfonic acid may be used.

Suitable alcohols of at least 4 carbon atoms include 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-sec-butyl ether, di-n-pentyl ether, diisopentyl ether, di-sec-pentyl ether, di-t-amyl ether, and di-n-hexyl ether.

Exposure is preferably performed in an exposure dose of about 1 to 200 mJ/cm$^2$, more preferably about 10 to 100 mJ/cm$^2$. This is followed by baking (PEB) on a hot plate at 60 to 150° C. for 1 to 5 minutes, preferably at 80 to 120° C. for 1 to 3 minutes.

Figure 1C:
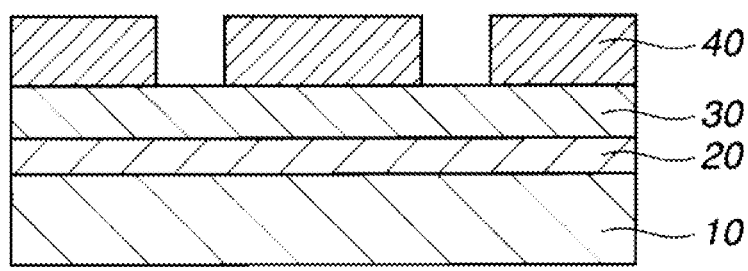

Thereafter the exposed resist film is developed in a developer consisting of an organic solvent for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1C. The developer used herein is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. Suitable aromatic solvents include toluene, xylene, ethylbenzene, isopropylbenzene, tert-butylbenzene, and mesitylene. The solvents may be used alone or in admixture.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

EXAMPLE

Synthesis Examples and Examples of the invention are given below by way of illustration and not by way of limitation. The abbreviation "pbw" is parts by weight. Me stands for methyl. For all polymers, Mw and Mn are determined versus polystyrene standards by GPC.

Synthesis Example 1

Polymerizable ester compounds within the scope of the invention were synthesized in accordance with the formulation shown below.

Synthesis Example 1-1

Synthesis of Monomer 1

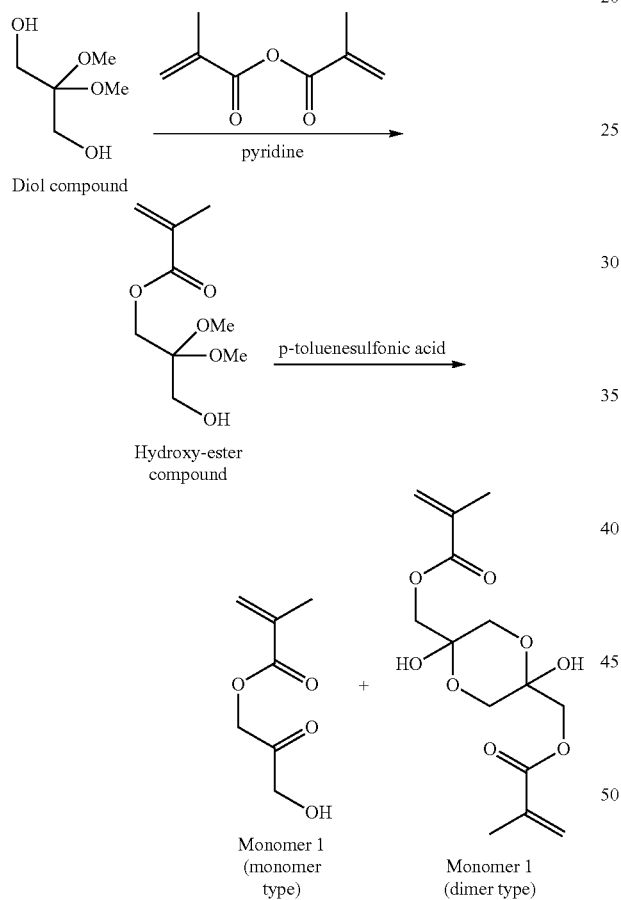

Synthesis Example 1-1-1

Synthesis of Hydroxy-Ester Compound

A mixture was obtained by combining 500 g of the diol compound, 290 g of pyridine and 1,000 ml of acetonitrile. While the mixture was kept at about 40° C., 377 g of methacrylic anhydride was added dropwise to the mixture, which was stirred at 40° C. for 20 hours. The reaction solution was ice cooled whereupon an aqueous solution of sodium hydrogencarbonate was added to quench the reaction. This was followed by standard aqueous workup. After the solvent was distilled off, the product was purified by distillation, obtaining 360 g (yield 72%) of a hydroxy-ester compound.

b.p.: 73° C./14 Pa

IR (D-ATR): ν=3488, 2961, 2837, 1722, 1638, 1456, 1404, 1377, 1326, 1304, 1258, 1149, 1084, 943, 858, 814, 769, 658, 617, 588=$^{-1}$ $^1$H-NMR (600 MHz in DMSO-$d_6$): δ=6.03 (1H, s), 5.69 (1H, m), 4.88 (1H, t), 4.08 (2H, s), 3.39 (2H, d), 3.14 (6H, s), 1.88 (3H, m) ppm

Synthesis Example 1-1-2

Synthesis of Monomer 1

The resulting hydroxy-ester compound, 360 g, was dissolved in 600 ml of water, to which 16 g of p-toluenesulfonic acid monohydrate was added. The solution was stirred at 40° C. for 4 hours. The reaction solution was ice cooled whereupon 8 g of sodium hydrogencarbonate was added to quench the reaction. This was followed by standard aqueous workup. The solvent was distilled off, obtaining 279 g of Monomer 1. Monomer 1 was obtained quantitatively and had a high purity sufficient to eliminate further purification. As seen from the above formula, Monomer 1 was an equilibrium mixture of monomer and dimer (white solid).

IR (D-ATR, equilibrium mixture of monomer and dimer): ν=3327, 2948, 1716, 1636, 1451, 1411, 1386, 1327, 1295, 1239, 1170, 1157, 1112, 1097, 1075, 1024, 951, 930, 916, 873, 812, 717, 654, 597=$^{-1}$ $^1$H-NMR (600 MHz in DMSO-$d_6$, only chemical shifts of monomer are shown because complex peaks appear from an equilibrium mixture of monomer and dimer): δ=6.09 (1H, s), 5.74 (1H, m), 5.37 (1H, t), 4.96 (2H, s), 4.14 (2H, d), 1.90 (3H, s) ppm

Synthesis Example 1-2

Synthesis of Monomer 2

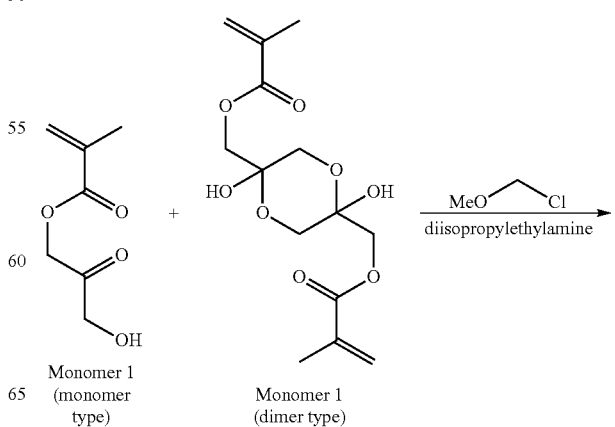

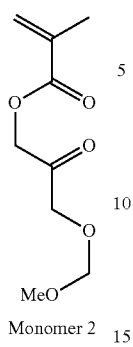

Monomer 2

In 150 ml of acetonitrile were dissolved 100 g of Monomer 1 (equilibrium mixture of monomer and dimer) and 66 g of methoxymethyl chloride. To the solution kept at about 40° C., 106 g of N,N-diisopropylethylamine in 100 ml of acetonitrile was added dropwise. The solution was stirred at 40° C. for 12 hours. The reaction solution was ice cooled whereupon an aqueous solution of sodium hydrogencarbonate was added dropwise to quench the reaction. This was followed by standard aqueous workup. The solvent was distilled off. The product was purified by distillation, obtaining 128 g (yield 84%) of Monomer 2.

b.p.: 76° C./12 Pa

IR (D-ATR): ν=2934, 2893, 2828, 1745, 1722, 1637, 1454, 1411, 1371, 1324, 1300, 1153, 1114, 1065, 1034, 945, 813, 653, 581, 560=$^{-1}$ $^1$H-NMR (600 MHz in DMSO-$d_6$): δ=6.10 (1H, m), 5.75 (1H, m), 4.95 (2H, s), 4.61 (2H, s), 4.28 (2H, s), 3.28 (3H, s), 1.90 (3H, s) ppm

Synthesis Example 1-3

Synthesis of Monomer 3

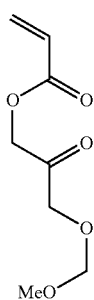

Monomer 3

Monomer 3 was synthesized by the same procedure as Synthesis Examples 1-1 and 1-2 aside from using acrylic anhydride instead of methacrylic anhydride. Three-step yield 63%.

Synthesis Example 1-4

Synthesis of Monomer 4

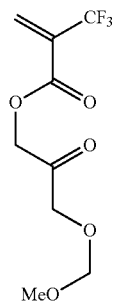

Monomer 4

Monomer 4 was synthesized by the same procedure as Synthesis Examples 1-1 and 1-2 aside from using α-trifluoromethylacrylic anhydride instead of methacrylic anhydride. Three-step yield 59%.

Synthesis Example 1-5

Synthesis of Monomer 5

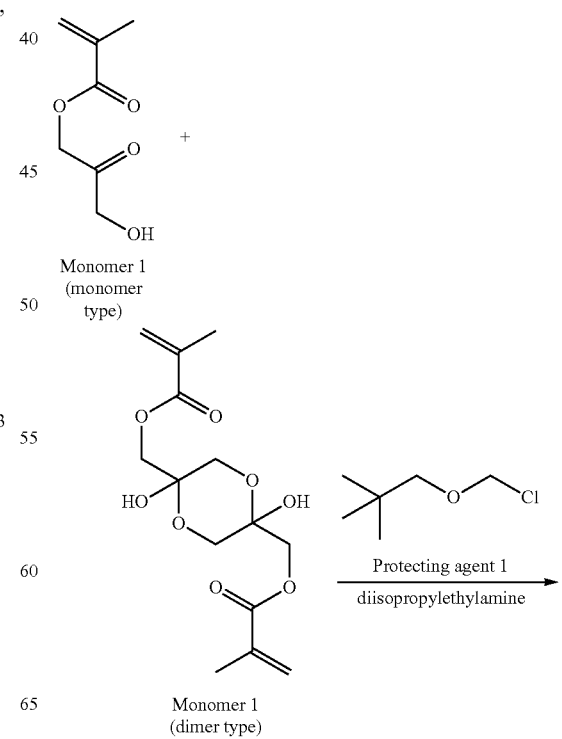

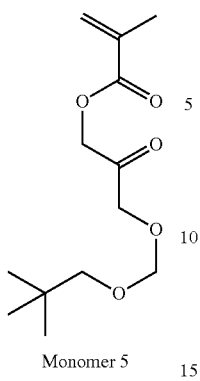

Monomer 5

Monomer 5 was synthesized by the same procedure as Synthesis Example 1-2 aside from using Protecting agent 1 instead of methoxymethyl chloride. Yield 83%.

b.p.: 95° C./13 Pa

IR (D-ATR): ν=2956, 2900, 2870, 1747, 1724, 1638, 1481, 1459, 1411, 1364, 1323, 1299, 1168, 1151, 1120, 1069, 1042, 1031, 972, 939, 811 cm$^{-1}$ $^1$H-NMR (600 MHz in DMSO-d$_6$): δ=6.09 (1H, s), 5.75 (1H, m), 4.94 (2H, s), 4.68 (2H, s), 4.27 (2H, s), 3.17 (2H, s), 1.90 (3H, s), 0.87 (9H, s) ppm Synthesis Example 1-6

Synthesis of Monomer 6

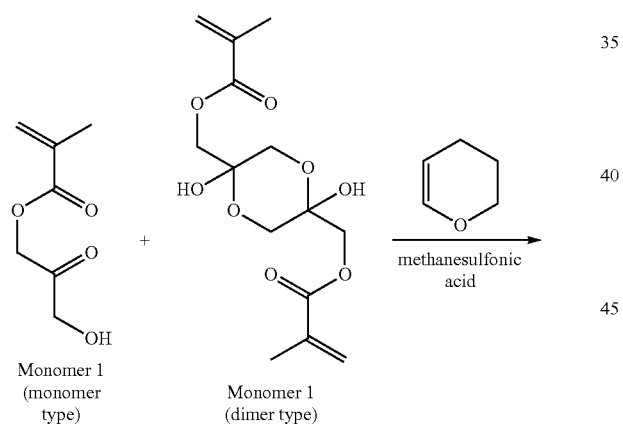

Monomer 1 (monomer type)   Monomer 1 (dimer type)

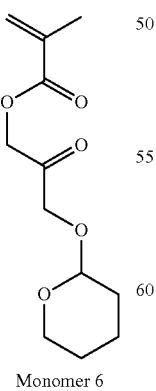

Monomer 6

In 100 ml of acetonitrile were dissolved 50 g of Monomer 1 (equilibrium mixture of monomer and dimer) and 54 g of 3,4-dihydro-2H-pyran. The solution was ice cooled, whereupon 0.60 g of methanesulfonic acid was added. The solution was allowed to warm up from ice cooled temperature to room temperature over 12 hours. An aqueous solution of sodium hydrogencarbonate was added thereto to quench the reaction. This was followed by standard aqueous workup. The solvent was distilled off. The product was purified by distillation, obtaining 71 g (yield 93%) of Monomer 6.

b.p.: 98° C./20 Pa $^1$H-NMR (600 MHz in DMSO-d$_6$): δ=6.09 (1H, s), 5.75 (1H, m), 4.96 (2H, m), 4.62 (1H, m), 4.28 (1H, m), 3.74 (1H, m), 3.44 (1H, m), 1.90 (3H, s), 1.73 (1H, m), 1.66 (1H, m), 1.40-1.57 (4H) ppm Synthesis Example 1-7

Synthesis of Monomer 7

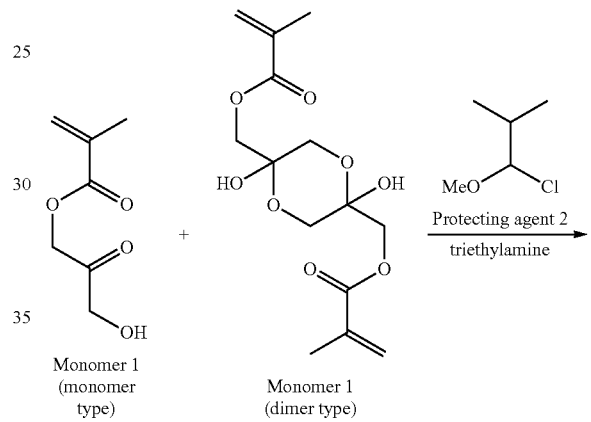

Monomer 1 (monomer type)   Monomer 1 (dimer type)

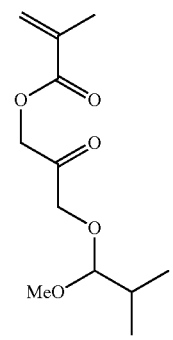

Monomer 7

Monomer 7 was synthesized by the same procedure as Synthesis Example 1-2 aside from using Protecting agent 2 instead of methoxymethyl chloride and triethylamine instead of N,N-diisopropylamine. Yield 83%.

Synthesis Example 1-8

Synthesis of Monomer 8

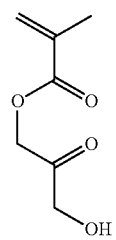

Monomer 1
(monomer type)

+

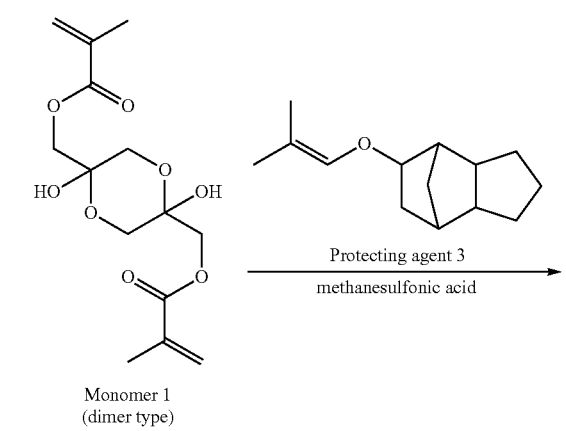

Monomer 1
(dimer type)

Monomer 8 was synthesized by the same procedure as Synthesis Example 1-6 aside from using Protecting agent 3 instead of 3,4-dihydro-2H-pyran. Yield 81%.

Synthesis Example 1-9

Synthesis of Monomer 9

Monomer 1
(monomer type)

+

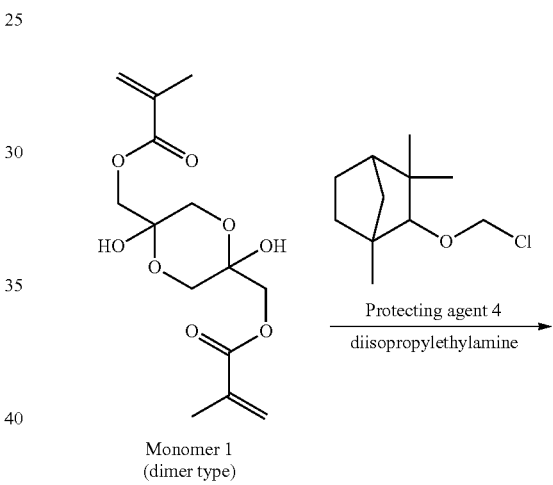

Monomer 1
(dimer type)

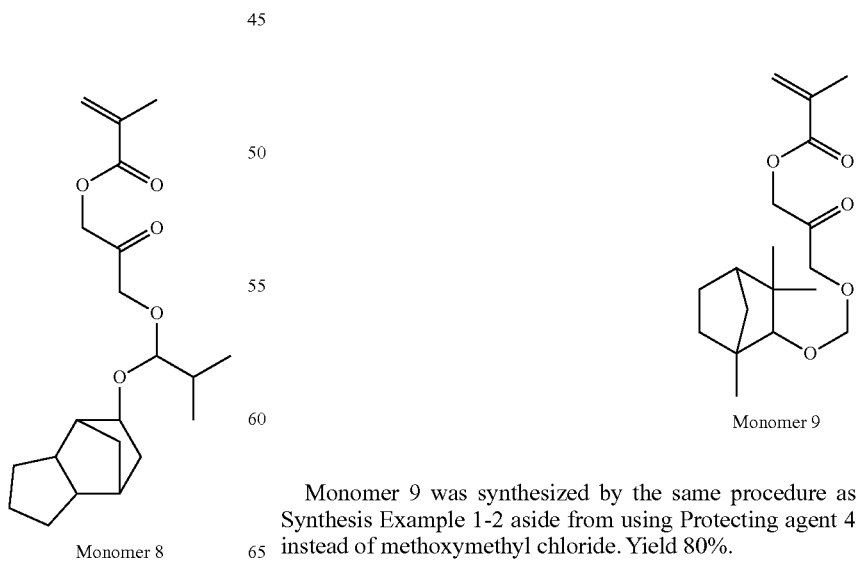

Monomer 8

Monomer 9

Monomer 9 was synthesized by the same procedure as Synthesis Example 1-2 aside from using Protecting agent 4 instead of methoxymethyl chloride. Yield 80%.

Monomers 1 to 9 obtained in Synthesis Example 1 have the structural formulae shown below.

Monomer 1
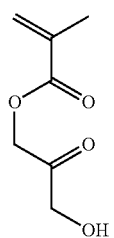
Monomer 2
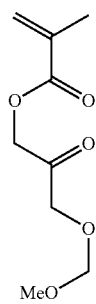
Monomer 3
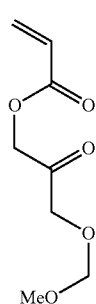
Monomer 4
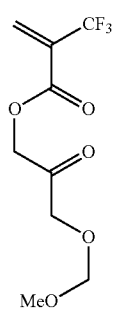
Monomer 5
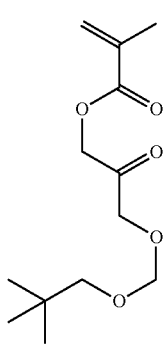
Monomer 6
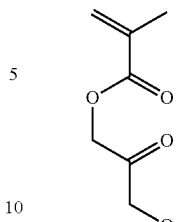
Monomer 7
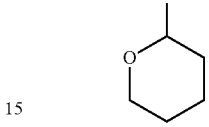
Monomer 8
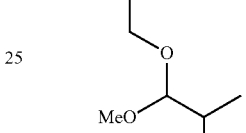
Monomer 9
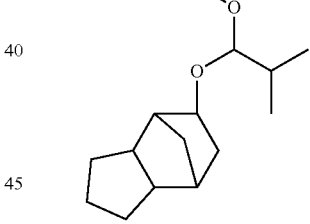
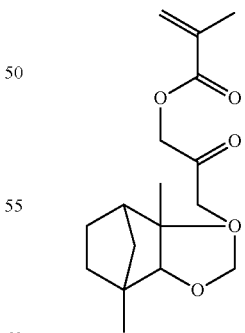
Synthesis Example 2
Polymers within the scope of the invention were synthesized in accordance with the formulation shown below.

Synthesis Example 2-1

Synthesis of Polymer 1

In a nitrogen atmosphere, 37.7 g of Monomer 2, 33.5 g of 4,8-dioxatricyclo[4.2.1.0$^{3,7}$]nonan-5-on-2-yl methacrylate, 8.8 g of 3-hydroxyadamantyl methacrylate, and 4.3 g of dimethyl 2,2'-azobisisobutyrate were dissolved in 111 g of methyl ethyl ketone. With stirring under a nitrogen atmosphere, the solution was added dropwise to 37 g of methyl ethyl ketone at 80° C. over 4 hours. After the completion of dropwise addition, the reaction solution was stirred at 80° C. for 2 hours. The polymerization solution was cooled to room temperature, whereupon it was added dropwise to 800 g of hexane. The thus precipitated solids were filtered and dried in vacuum at 50° C. for 20 hours, obtaining a polymer in white powder solid form, designated Polymer 1. Amount 73.6 g, yield 92%.

Polymer 1

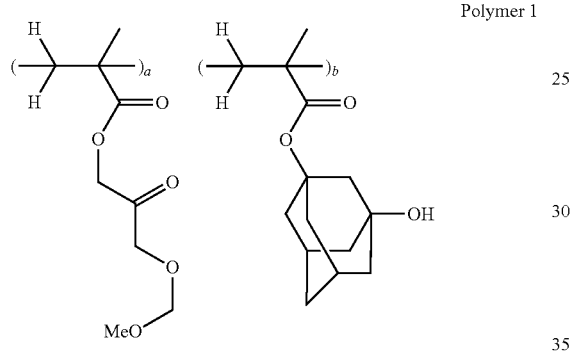

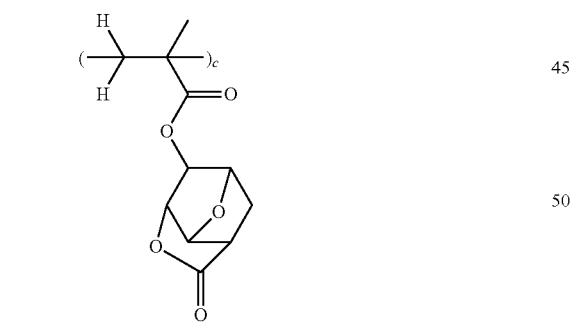

(a = 0.50, b = 0.10, c = 0.40, Mw - 7,400)

Synthesis Examples 2-2 to 2-12 and Comparative Synthesis Examples 1-1 to 1-6

Polymers 2 to 12 and Reference Polymers 1 to 6 were synthesized by the same procedure as Synthesis Example 2-1 except that the type and proportion of monomers were changed. The structure of these polymers is identified below. Fractions of units incorporated are expressed in molar ratio.

Polymer 2

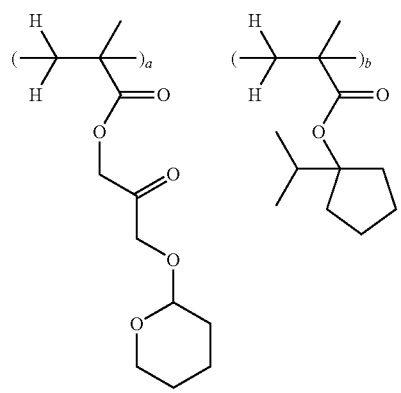

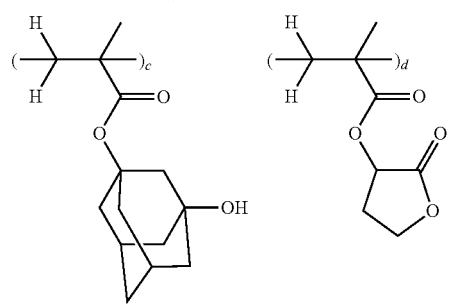

(a = 0.25, b = 0.25, c = 0.10, d = 0.40, Mw = 7,200)

Polymer 3

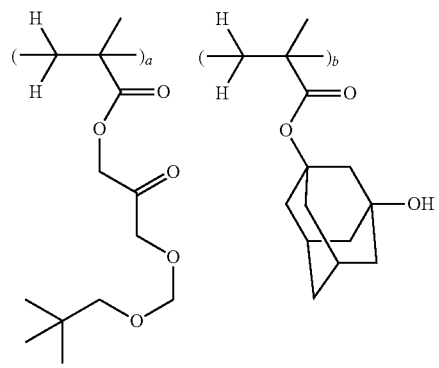

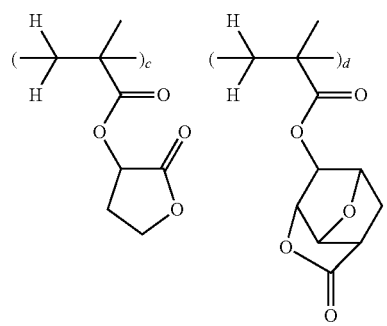

(a = 0.50, b = 0.10, c = 0.20, d = 0.20, Mw = 7,300)

Polymer 4
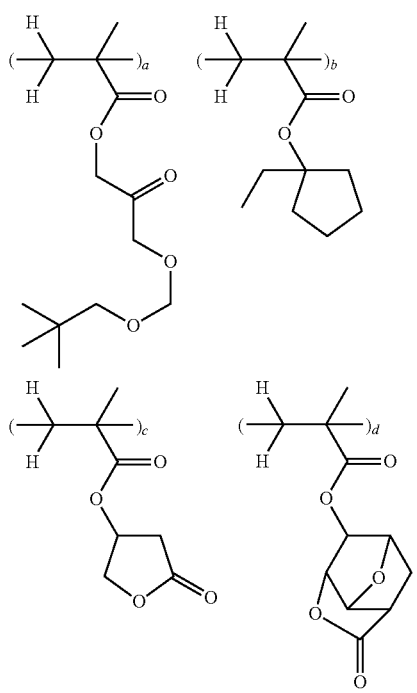
(a = 0.25, b = 0.25, c = 0.30, d = 0.20, Mw = 7,200)
Polymer 6
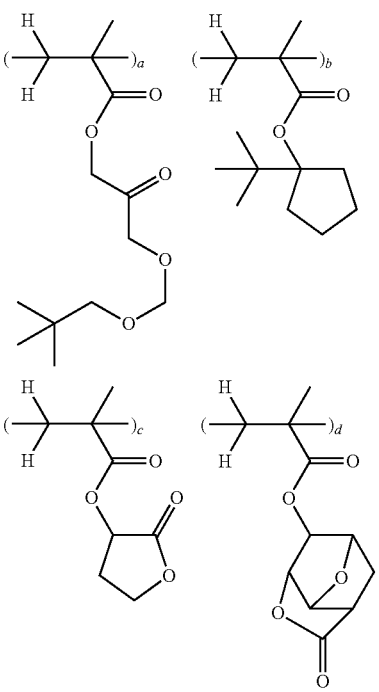
(a = 0.30, b = 0.20, c = 0.30, d = 0.20, Mw = 7,200)
Polymer 5
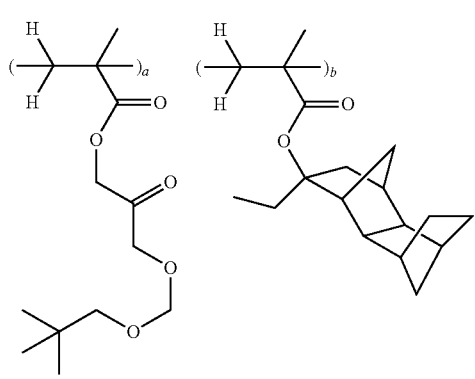
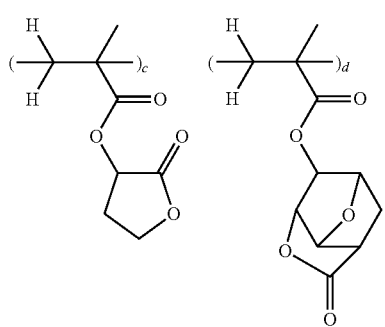
(a = 0.25, b = 0.25, c = 0.30, d = 0.20, Mw = 7,200)
Polymer 7
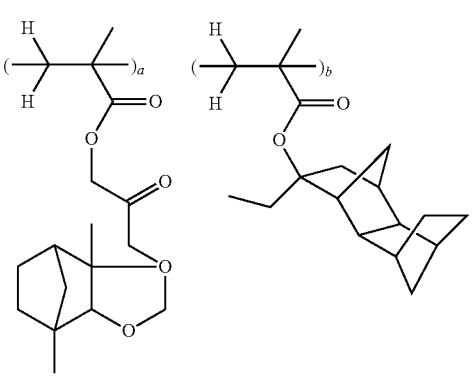
(a = 0.25, b = 0.25, c = 0.30, d = 0.20, Mw = 7,300)

Polymer 8
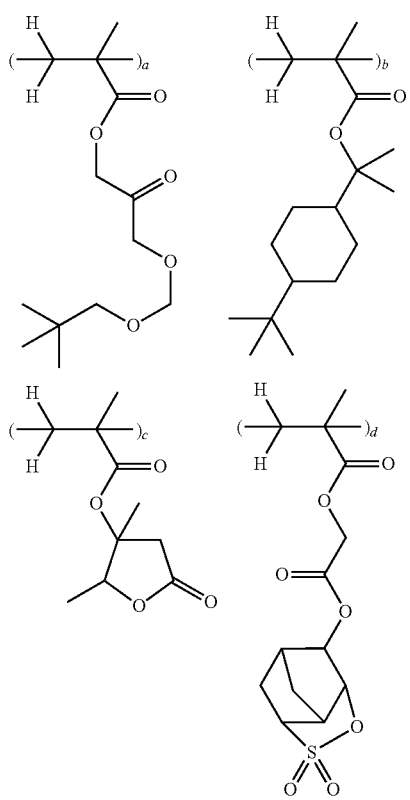
(a = 0.25, b = 0.30, c = 0.25, d = 0.20, Mw = 7,300)
Polymer 9
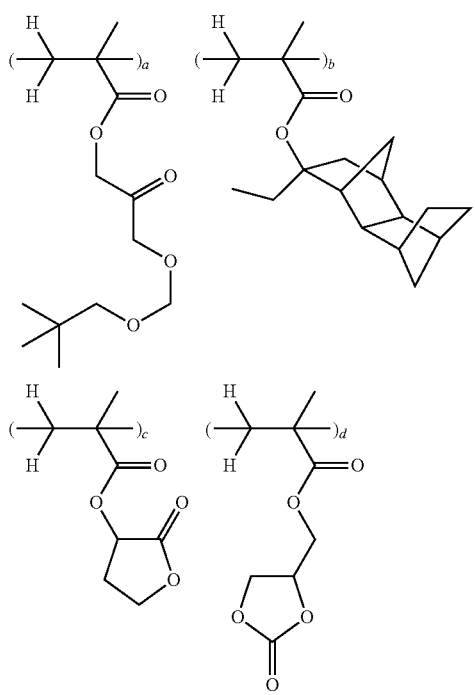
(a = 0.30, b = 0.20, c = 0.30, d = 0.20, Mw = 7,400)
Polymer 10
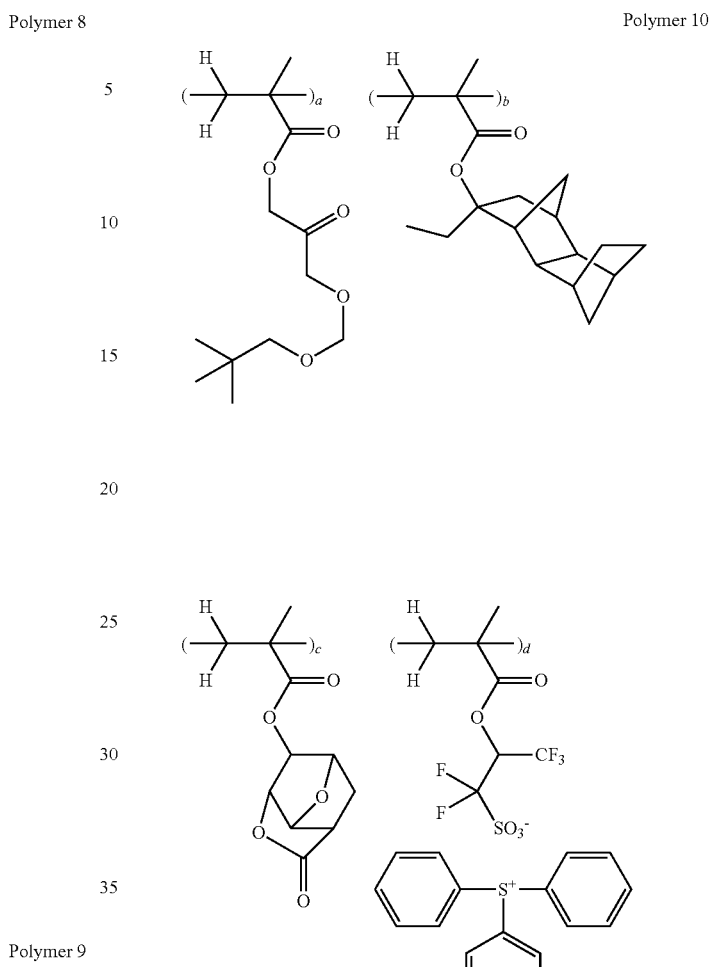
(a = 0.25, b = 0.35, c = 0.35, d = 0.05, Mw = 7,100)
Polymer 11
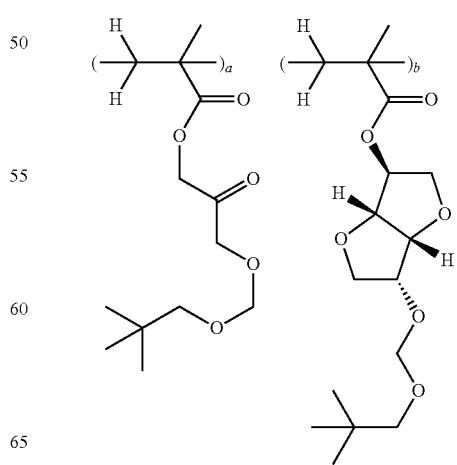

-continued
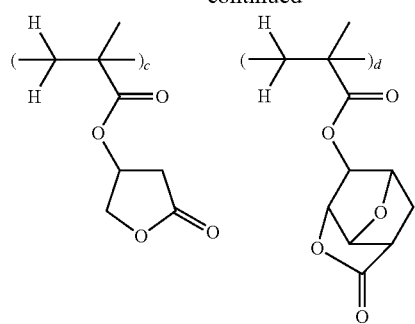
(a = 0.25, b = 0.25, c = 0.30, d = 0.20, Mw = 7,300)
Polymer 12
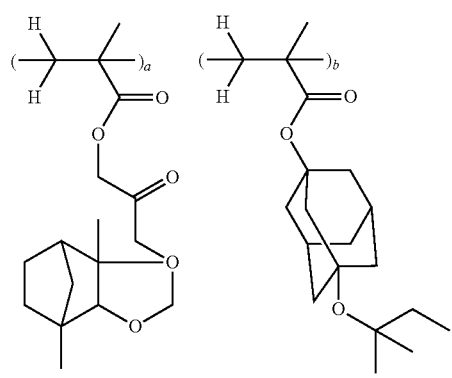
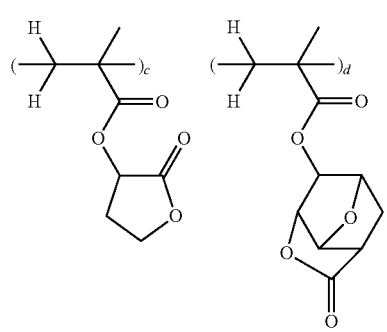
(a = 0.25, b = 0.25, c = 0.30, d = 0.20, Mw = 7,400)
Reference Polymer 1
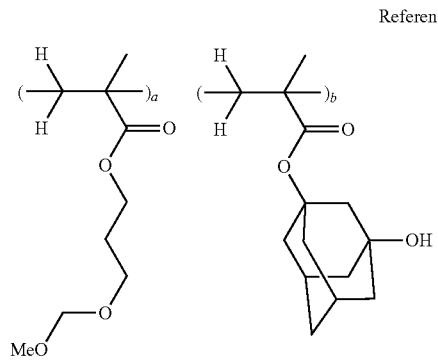
-continued
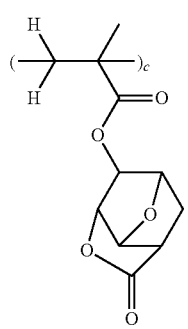
(a = 0.50, b = 0.10, c = 0.40, Mw = 7,400)
Reference Polymer 2
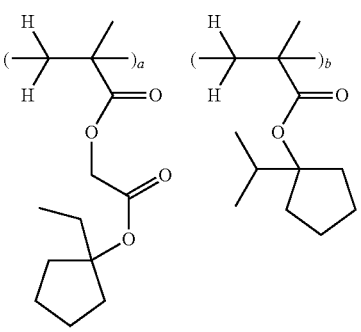
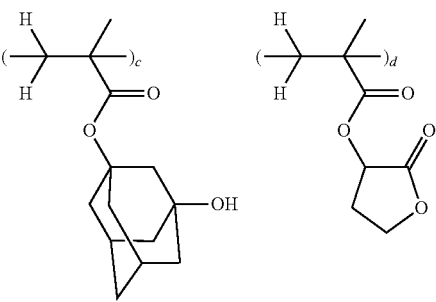
(a = 0.25, b = 0.25, c = 0.10, d = 0.40, Mw = 7,200)
Reference Polymer 3
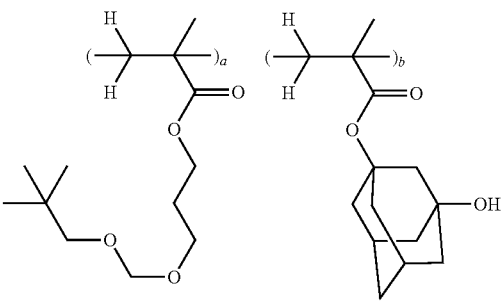

-continued

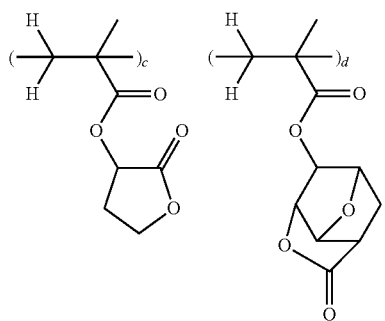

(a = 0.50, b = 0.10, c = 0.20, d = 0.20, Mw = 7,300)

-continued

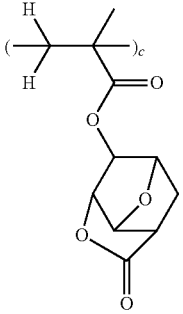

(a = 0.50, b = 0.25, c = 0.25, Mw = 7,300)

Reference Polymer 4

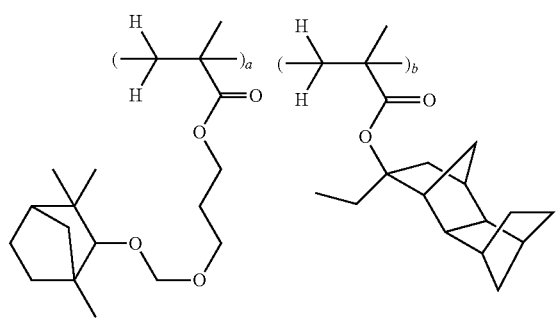

(a = 0.25, b = 0.25, c = 0.30, d = 0.20, Mw = 7,300)

Reference Polymer 6

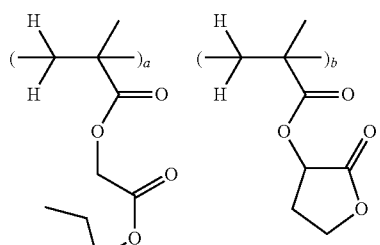

(a = 0.50, b = 0.25, c = 0.25, Mw = 7,300)

Examples 1-1 to 1-12 and Comparative Examples 1-1 to 1-6

Preparation of Resist Composition

Resist compositions R-1 to R-12 and Comparative Resist compositions R-13 to R-19 in solution form were prepared by dissolving a polymer (Polymers 1 to 12 or Reference Polymers 1 to 6) as base resin, acid generator, basic compound, and water-repellent polymer in a solvent in accordance with the formulation of Table 1 and filtering through a Teflon® filter with a pore size of 0.2 µm. The solvent contained 0.01 wt % of surfactant KH-20 (Asahi Glass Co., Ltd.). The photoacid generator (PAG-1, PAG-2), quencher (Base-1), solvent, and water-repellent polymer (SF-1, 2) used herein are identified below.

PAG-1: triphenylsulfonium 2-(adamantane-1-carbonyloxy)-1,1,3,3,3-pentafluoropropanesulfonate PAG-2: 4-tert-butylphenyldiphenylsulfonium 2-(adamantane-1-carbonyloxy)-1,1,3,3,3-pentafluoropropanesulfonate Reference Polymer 5

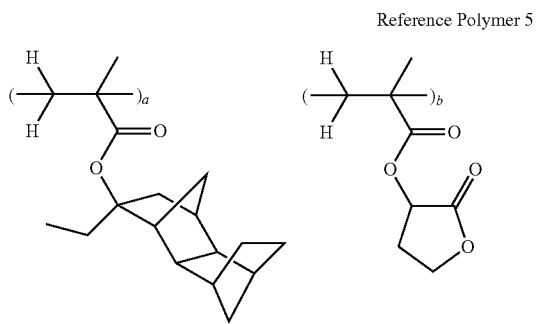

Base-1: 2-morpholinoethyl octadecanoate
PGMEA: 1-methyl-2-methoxyethyl acetate
CyH: cyclohexanone
Water-repellent polymer SF-1:

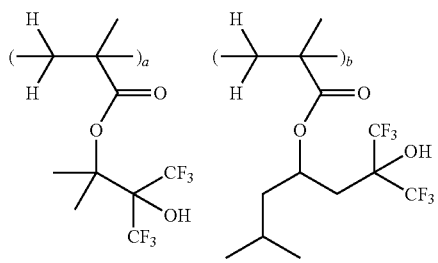

(a = 0.50, b = 0.50, Mw = 8,900)

Water-repellent polymer SF-2:

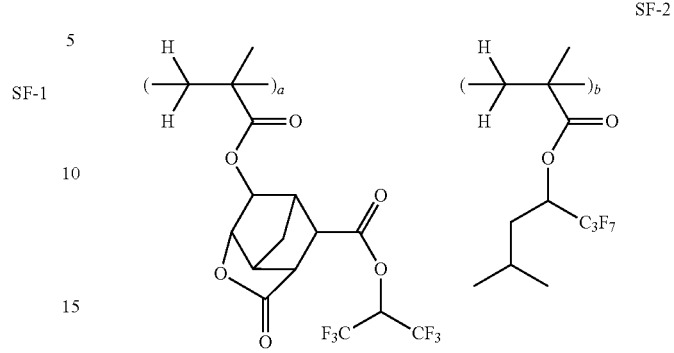

(a = 0.50, b = 0.50, Mw = 7,500)

TABLE 1

|  |  | Resist | Resin (pbw) | PAG (pbw) | Quencher (pbw) | Water-repellent polymer (pbw) | Solvent 1 (pbw) | Solvent 2 (pbw) |
|---|---|---|---|---|---|---|---|---|
| Example | 1-1 | R-1 | Polymer 1 (100) | PAG-1 (12.5) | Base-1 (1.5) | SF-1 (6.0) | PGMEA (2,000) | CyH (500) |
|  | 1-2 | R-2 | Polymer 2 (100) | PAG-2 (12.5) | Base-1 (1.5) | SF-1 (6.0) | PGMEA (2,000) | CyH (500) |
|  | 1-3 | R-3 | Polymer 3 (100) | PAG-1 (12.5) | Base-1 (1.5) | SF-2 (6.0) | PGMEA (2,000) | CyH (500) |
|  | 1-4 | R-4 | Polymer 4 (100) | PAG-1 (12.5) | Base-1 (1.5) | SF-2 (6.0) | PGMEA (2,000) | CyH (500) |
|  | 1-5 | R-5 | Polymer 5 (100) | PAG-1 (12.5) | Base-1 (1.5) | SF-2 (6.0) | PGMEA (2,000) | CyH (500) |
|  | 1-6 | R-6 | Polymer 6 (100) | PAG-2 (12.5) | Base-1 (1.5) | SF-2 (6.0) | PGMEA (2,000) | CyH (500) |
|  | 1-7 | R-7 | Polymer 7 (100) | PAG-1 (12.5) | Base-1 (1.5) | SF-2 (6.0) | PGMEA (2,000) | CyH (500) |
|  | 1-8 | R-8 | Polymer 8 (100) | PAG-1 (12.5) | Base-1 (1.5) | SF-2 (6.0) | PGMEA (2,000) | CyH (500) |
|  | 1-9 | R-9 | Polymer 9 (100) | PAG-1 (12.5) | Base-1 (1.5) | SF-2 (6.0) | PGMEA (2,000) | CyH (500) |
|  | 1-10 | R-10 | Polymer 10 (100) | — | Base-1 (1.5) | SF-2 (6.0) | PGMEA (2,000) | CyH (500) |
|  | 1-11 | R-11 | Polymer 11 (100) | PAG-1 (12.5) | Base-1 (1.5) | SF-2 (6.0) | PGMEA (2,000) | CyH (500) |
|  | 1-12 | R-12 | Polymer 12 (100) | PAG-1 (12.5) | Base-1 (1.5) | SF-2 (6.0) | PGMEA (2,000) | CyH (500) |
| Comparative Example | 1-1 | R-13 | Reference Polymer 1 (100) | PAG-1 (12.5) | Base-1 (1.5) | SF-1 (6.0) | PGMEA (2,000) | CyH (500) |
|  | 1-2 | R-14 | Reference Polymer 2 (100) | PAG-2 (12.5) | Base-1 (1.5) | SF-1 (6.0) | PGMEA (2,000) | CyH (500) |
|  | 1-3 | R-15 | Reference Polymer 3 (100) | PAG-1 (12.5) | Base-1 (1.5) | SF-2 (6.0) | PGMEA (2,000) | CyH (500) |
|  | 1-4 | R-16 | Reference Polymer 4 (100) | PAG-1 (12.5) | Base-1 (1.5) | SF-2 (6.0) | PGMEA (2,000) | CyH (500) |
|  | 1-5 | R-17 | Reference Polymer 5 (100) | PAG-1 (12.5) | Base-1 (1.5) | SF-2 (6.0) | PGMEA (2,000) | CyH (500) |
|  | 1-6 | R-18 | Reference Polymer 6 (100) | PAG-1 (12.5) | Base-1 (1.5) | SF-2 (6.0) | PGMEA (2,000) | CyH (500) |

Examples 2-1, 2-2 and Comparative Examples 2-1, 2-2

ArF Lithography Patterning Test 1

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-1, R-2, R-13 or R-14) shown in Table 1 was spin coated, then baked on a hot plate at 100° C. for 60 seconds to form a resist film of 80 nm thick.

Using an ArF excimer laser immersion lithography stepper NSR-610C (Nikon Corp., NA 1.30, σ 6 0.98/0.78, dipole opening 20 deg., azimuthally polarized illumination), exposure was performed through a 6% halftone phase shift mask bearing a line pattern with a pitch of 80 nm and a line width of 40 nm (on-wafer size) by dipole illumination. After the exposure, the wafer was baked (PEB) at the temperature shown in Table 2 for 60 seconds and puddle developed in an aqueous solution of 2.38 wt % tetramethylammonium hydroxide (TMAH) for 30 seconds. The wafer was rinsed with deionized water and spin dried, forming a line-and-space pattern.

A variation in line width of the line-and-space pattern was measured under TDSEM S-9380 (Hitachi Hitechnologies, Ltd.) and reported as line width roughness (LWR). A smaller value of LWR is better because it indicates minimized fluctuation of a line pattern. The results are shown in Table 2.

TABLE 2

|  | Resist | PEB temperature (° C.) | Dose (mJ/cm$^2$) | LWR (nm) |
|---|---|---|---|---|
| Example |  |  |  |  |
| 2-1 | R-1 | 90 | 49 | 3.3 |
| 2-2 | R-2 | 85 | 47 | 3.4 |
| Comparative Example |  |  |  |  |
| 2-1 | R-13 | 90 | 48 | 5.6 |
| 2-2 | R-14 | 85 | 46 | 5.7 |

Examples 3-1 to 3-10 and Comparative Examples 3-1 to 3-4

ArF Lithography Patterning Test 2

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition (R-3 to R-12, R-15 to R-18) shown in Table 1 was spin coated, then baked on a hot plate at 100° C. for 60 seconds to form a resist film of 100 nm thick.

Using an ArF excimer laser immersion lithography stepper NSR-610C (Nikon Corp., NA 1.30, σ 0.98/0.78, dipole opening 20 deg., azimuthally polarized illumination, dipole illumination), first exposure was performed through a 6% halftone phase shift mask bearing a X-direction line pattern with a pitch of 80 nm and a line width of 40 nm. Second exposure was then performed through a 6% halftone phase shift mask bearing a Y-direction line pattern with a pitch of 80 nm and a line width of 40 nm. After the exposure, the wafer was baked (PEB) at the temperature shown in Table 3 for 60 seconds and developed. Specifically, butyl acetate was injected from a development nozzle while the wafer was spun at 30 rpm for 3 seconds, which was followed by stationary puddle development for 27 seconds. The wafer was rinsed with 4-methyl-2-pentanol, spin dried, and baked at 100° C. for 20 seconds to evaporate off the rinse liquid.

A hole pattern resulted from image reversal by solvent development. By observation under TDSEM S-9380 (Hitachi Hitechnologies, Ltd.), the size of 50 holes was measured, from which a size variation 3σ was determined. A smaller value of 3σ is better because it indicates a minimized variation of hole size. The results are shown in Table 3.

TABLE 3

|  | Resist | PEB temperature (° C.) | Dose (mJ/cm$^2$) | Hole size variation 3σ (nm) |
|---|---|---|---|---|
| Example |  |  |  |  |
| 3-1 | R-3 | 90 | 37 | 1.5 |
| 3-2 | R-4 | 85 | 35 | 1.6 |
| 3-3 | R-5 | 90 | 36 | 1.4 |
| 3-4 | R-6 | 85 | 36 | 1.4 |
| 3-5 | R-7 | 90 | 35 | 1.3 |
| 3-6 | R-8 | 90 | 38 | 1.5 |
| 3-7 | R-9 | 90 | 37 | 1.4 |
| 3-8 | R-10 | 85 | 35 | 1.6 |
| 3-9 | R-11 | 90 | 37 | 1.5 |
| 3-10 | R-12 | 90 | 37 | 1.6 |
| Comparative Example |  |  |  |  |
| 3-1 | R-15 | 90 | 36 | 3.7 |
| 3-2 | R-16 | 85 | 35 | 3.9 |
| 3-3 | R-17 | 95 | 40 | 2.5 |
| 3-4 | R-18 | 90 | 38 | 2.6 |

As seen from the results of Tables 2 and 3, the resist compositions within the scope of the invention are not only effective for forming positive patterns using conventional alkaline developers, i.e., forming line patterns with improved LWR, but also effective for forming negative patterns by organic solvent development, i.e., forming hole patterns with hole size uniformity. The resist compositions are broadly applicable to both the alkaline development and organic solvent development processes.

Japanese Patent Application No. 2013-004273 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the general formula (1):

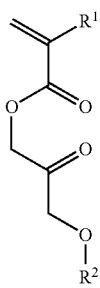
(1)

wherein $R^1$ is hydrogen, methyl or trifluoromethyl and $R^2$ is hydrogen or an acid labile group.

2. The monomer of claim 1 wherein $R^2$ is an acid labile group.

3. A monomer having the general formula (2):

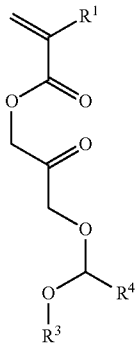
(2)

wherein $R^1$ is hydrogen, methyl or trifluoromethyl, $R^3$ is a straight, branched or cyclic, monovalent hydrocarbon group of 1 to 20 carbon atoms in which a constituent —$CH_2$— may be substituted by —O— or —C(=O)—, $R^4$ is hydrogen or a straight, branched or cyclic, monovalent hydrocarbon group of 1 to 20 carbon atoms, $R^3$ and $R^4$ may bond together to form a 5 or 6-membered ring with the carbon and oxygen atoms to which they are attached.

4. A polymer comprising recurring units having the general formula (3a) or (3b):

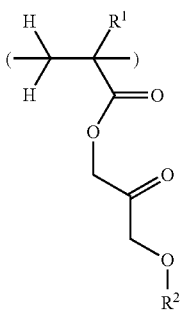
(3a)

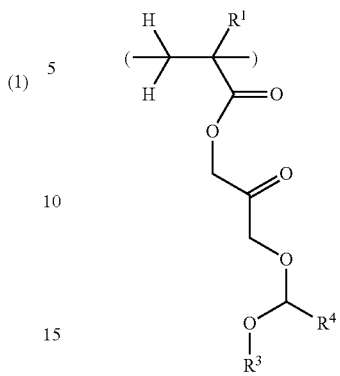
(3b)

wherein $R^1$ is hydrogen, methyl or trifluoromethyl, $R^2$ is hydrogen or an acid labile group, $R^3$ is a straight, branched or cyclic, monovalent hydrocarbon group of 1 to 20 carbon atoms in which a constituent —$CH_2$— may be substituted by —O— or —C(=O)—, $R^4$ is hydrogen or a straight, branched or cyclic, monovalent hydrocarbon group of 1 to 20 carbon atoms, $R^3$ and $R^4$ may bond together to form a 5 or 6-membered ring with the carbon and oxygen atoms to which they are attached.

5. The polymer of claim 4 wherein $R^2$ is an acid labile group.

6. The polymer of claim 4, further comprising recurring units of at least one type selected from recurring units having the general formulae (4A) to (4E):

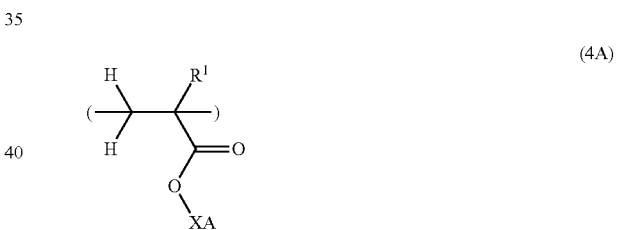
(4A)

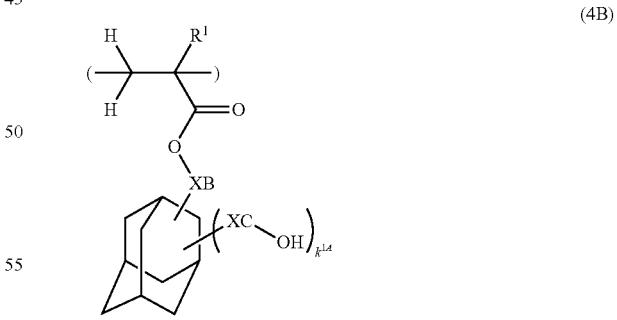
(4B)

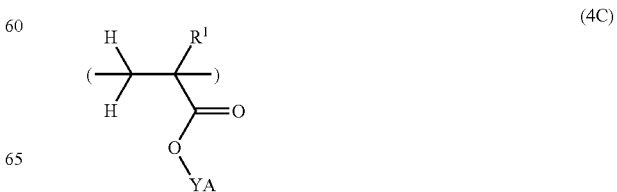
(4C)

-continued

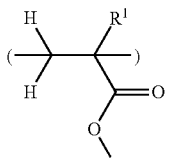
(4D)

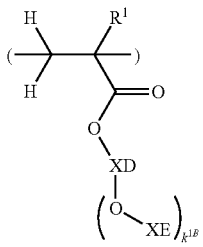
(4E)

wherein $R^1$ is as defined above, XA is an acid labile group, XB and XC are each independently a single bond or a straight or branched, divalent hydrocarbon group of 1 to 4 carbon atoms, XD is a straight, branched or cyclic, di- to pentavalent aliphatic hydrocarbon group of 1 to 16 carbon atoms in which a constituent —CH$_2$— may be substituted by —O— or —C(=O)—, XE is an acid labile group, YA is a substituent group of lactone, sultone or carbonate structure, ZA is hydrogen, a fluoroalkyl group of 1 to 15 carbon atoms or a fluoroalcohol-containing group of 1 to 15 carbon atoms, $k^{1A}$ is an integer of 1 to 3, and $k^{1B}$ is an integer of 1 to 4.

7. The polymer of claim 4, further comprising recurring units of at least one type selected from sulfonium salt units (d1) to (d3) represented by the following general formula:

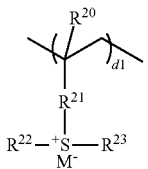
(d1)

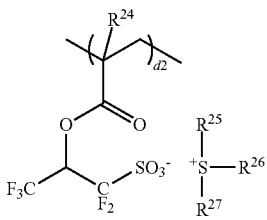
(d2)

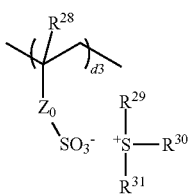
(d3)

wherein $R^{20}$, $R^{24}$, and $R^{28}$ each are hydrogen or methyl; R21 is a single bond, phenylene, —O—$R^{33}$—, or —C(=O)—Y—$R^{33}$—, wherein Y is oxygen or NH and $R^{33}$ is a straight, branched or cyclic $C_1$-$C_6$ alkylene group, alkenylene group or phenylene group, which may contain a carbonyl (—CO—), ester (—COO—), ether (—O—), or hydroxyl moiety; $R^{22}$, $R^{23}$, $R^{25}$, $R^{26}$, $R^{27}$, $R^{29}$, $R^{30}$ and $R^{31}$ are each independently a straight, branched or cyclic $C_1$-$C_{12}$ alkyl group which may contain a carbonyl, ester or ether moiety, a $C_6$-$C_{12}$ aryl group, a $C_7$-$C_{20}$ aralkyl group, or a thiophenyl group; $Z_0$ is a single bond, methylene, ethylene, phenylene, fluorinated phenylene, —O—$R^{32}$—, or —C(=O)—$Z_1$-$R^{32}$—, wherein $Z_1$ is oxygen or NH, and $R^{32}$ is a straight, branched or cyclic $C_1$-$C_6$ alkylene group, alkenylene group or phenylene group, which may contain a carbonyl, ester, ether or hydroxyl moiety; and M⁻ is a non-nucleophilic counter ion.

8. A resist composition comprising a base resin containing the polymer of claim 4, an acid generator, and an organic solvent.

9. A resist composition comprising a base resin containing the polymer of claim 7, and an organic solvent.

10. A pattern forming process comprising the steps of applying the resist composition of claim 8 onto a substrate, prebaking to form a resist film, exposing the resist film to high-energy radiation, baking, and developing the exposed resist film in a developer.

11. The process of claim 10 wherein an aqueous alkaline solution is used as the developer in the developing step to form a positive pattern wherein the exposed region of resist film is dissolved away and the unexposed region of resist film is not dissolved.

12. The process of claim 10 wherein an organic solvent is used as the developer in the developing step to form a negative pattern wherein the unexposed region of resist film is dissolved away and the exposed region of resist film is not dissolved.

13. The process of claim 10 wherein the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

14. The process of claim 10 wherein the step of exposing the resist film to high-energy radiation includes KrF excimer laser lithography of wavelength 248 nm, ArF excimer laser lithography of wavelength 193 nm, EUV lithography of wavelength 13.5 nm or EB lithography.

* * * * *